United States Patent
Kjellman et al.

(10) Patent No.: US 12,359,183 B2
(45) Date of Patent: Jul. 15, 2025

(54) CYSTEINE PROTEASE

(71) Applicant: Hansa Biopharma AB, Lund (SE)

(72) Inventors: Christian Kjellman, Lund (SE); Sofia Jarnum, Lund (SE); Emma Andersson Nordahl, Lund (SE)

(73) Assignee: Hansa Biopharma AB, Lund (SE)

( * ) Notice: Subject to any disclaimer, the term of this patent is extended or adjusted under 35 U.S.C. 154(b) by 0 days.

(21) Appl. No.: 18/318,455

(22) Filed: May 16, 2023

(65) Prior Publication Data

US 2023/0357741 A1    Nov. 9, 2023

Related U.S. Application Data

(63) Continuation of application No. 17/644,315, filed on Dec. 14, 2021, now Pat. No. 11,667,905, which is a continuation of application No. 16/879,324, filed on May 20, 2020, now Pat. No. 11,214,784, which is a continuation of application No. 15/550,309, filed as application No. PCT/EP2016/053052 on Feb. 12, 2016, now Pat. No. 10,696,959.

(30) Foreign Application Priority Data

Feb. 12, 2015   (GB) ..................... 1502306

(51) Int. Cl.
| C12N 9/54 | (2006.01) |
| A61K 38/48 | (2006.01) |
| C12N 9/52 | (2006.01) |
| A61K 38/00 | (2006.01) |

(52) U.S. Cl.
CPC ............ *C12N 9/54* (2013.01); *A61K 38/48* (2013.01); *C12N 9/52* (2013.01); *A61K 38/00* (2013.01); *Y02A 50/30* (2018.01)

(58) Field of Classification Search
CPC .................................................. C12N 9/54
See application file for complete search history.

(56) References Cited

U.S. PATENT DOCUMENTS

| 10,696,959 | B2* | 6/2020 | Kjellman | A61P 37/06 |
| 11,214,784 | B2* | 1/2022 | Kjellman | A61P 3/10 |
| 11,667,905 | B2* | 6/2023 | Kjellman | A61P 31/14 |
| | | | | 435/220 |
| 2018/0023070 | A1 | 1/2018 | Kjellman et al. | |
| 2018/0037962 | A1 | 2/2018 | Kjellman et al. | |
| 2022/0170004 | A1 | 6/2022 | Kjellman et al. | |

FOREIGN PATENT DOCUMENTS

| WO | 0250107 | | 6/2002 |
| WO | 03051914 | A2 | 6/2003 |
| WO | 2006131347 | A2 | 12/2006 |
| WO | 2009033670 | A2 | 3/2009 |
| WO | 2009075646 | A1 | 6/2009 |
| WO | 2009080278 | A1 | 7/2009 |
| WO | 2010089126 | A2 | 8/2010 |
| WO | 2011149419 | A1 | 12/2011 |
| WO | 2013037824 | A1 | 3/2013 |
| WO | 2015040125 | A1 | 3/2015 |
| WO | 2016012285 | A3 | 4/2016 |
| WO | 2016128559 | A1 | 8/2016 |

OTHER PUBLICATIONS

Agniswamy et al., "Crystal Structure of group A *Streptococcus* MAC-1 orthorhombic form" Feb. 28, 2006, Database PDBe accession No. 2aul.
Akesson et al., "IdeS, a Highly Specific Immunoglobulin G (IgG)-Cleaving Enzyme from *Streptococcus pyogenes*, Is Inhibited by Specific IgG Antibodies Generated during Infection" (2006) Infect. Immun. 74:497-503.
European Search Report mailed Oct. 28, 2022 during examination of related European Patent Application No. 22174919.5-1118.
Fan Xuejun et al: "A Novel Therapeutic Strategy to Rescue the Immune Effector Function of Proteolytically Inactivated Cancer Therapeutic Antibodies", Molecular Cancer Therapeutics, vol. 14, No. 3, Oct. 11, 2022 (Oct. 11, 2022), pp. 681-691.
GenBankAccession No. PDB: 2AU1_A, published Dec. 27, 2012 (Year: 2012).
Jarnum Sofia et al: "Enzymatic Inactivation of Endogenous IgG by IdeS Enhances Therapeutic Antibody Efficacy", Molecular Cancer Therapeutics, vol. 16, No. 9, Sep. 1, 2017 (Sep. 1, 2017), pp. 1887-1897.
Nandakumar et al., "Therapeutic cleavage of IgG: new avenues for treating inflammation" Trends in immunology 29 (4):173-178.
Office Action issued on Chilean Application 201702065; application date: Nov. 2, 2017.
Persson et al., "Proteolytic processing of the streptococcal IgG endopeptidase IdeS modulates the functional properties of the enzyme and results in reduced immunorecognition" Mol. Immunol. (2015) 68(2):176-184.
Wenig et al., "Structure of the streptococcal endopeptidase IdeS, a cysteine proteinase with strict specificity for IgG" (2004) Proc. Natl. Acad. Sci. USA. 101:17371-17376.
IgG-degrading enzyme/Mac-1 IdeZ [*Streptococcus pyogenes*], GenBank Database, Accession No. WP_038434019.1, (2014); https://www.ncbi.nlm.nih.gov/protein/740648572?sat=48$satkey=106666213 [accessed Jul. 17, 2023].

* cited by examiner

*Primary Examiner* — Tekchand Saidha
(74) *Attorney, Agent, or Firm* — Norton Rose Fulbright US LLP

(57) ABSTRACT

The present invention relates to a novel polypeptide which displays IgG cysteine protease activity, and in vivo and ex vivo uses thereof. Uses of the polypeptide include methods for the prevention or treatment of diseases and conditions mediated by IgG, and methods for the analysis of IgG.

5 Claims, 13 Drawing Sheets

Specification includes a Sequence Listing.

A

B

A

B

SEQUENCE LISTING

```
Sequence total quantity: 37
SEQ ID NO: 1            moltype = AA  length = 339
FEATURE                 Location/Qualifiers
source                  1..339
                        mol_type = protein
                        organism = Streptococcus pyogenes
SEQUENCE: 1
MRKRCYSTSA AVLAAVTLFV LSVDRGVIAD SFSANQEIRY SEVTPYHVTS VWTKGVTPPA    60
NFTQGEDVFH APYVANQGWY DITKTFNGKD DLLCGAATAG NMLHWWFDQN KDQIKRYLEE   120
HPEKQKINFN GEQMFDVKEA IDTKNHQLDS KLFEYFKEKA FPYLSTKHLG VFPDHVIDMF   180
INGYRLSLTN HGPTPVKEGS KDPRGGIFDA VFTRGDQSKL LTSRHDFKEK NLKEISDLIK   240
KELTEGKALG LSHTYANVRI NHVINLWGAD FDSNGNLKAI YVTDSDSNAS IGMKKYFVGV   300
NSAGKVAISA KEIKEDNIGA QVLGLFTLST GQDSWNQTN                         339

SEQ ID NO: 2            moltype = AA  length = 310
FEATURE                 Location/Qualifiers
source                  1..310
                        mol_type = protein
```

```
                           organism = Streptococcus pyogenes
SEQUENCE: 2
DSFSANQEIR YSEVTPYHVT SVWTKGVTPP ANFTQGEDVF HAPYVANQGW YDITKTFNGK    60
DDLLCGAATA GNMLHWWFDQ NKDQIKRYLE EHPEKQKINF NGEQMFDVKE AIDTKNHQLD   120
SKLFEYFKEK AFPYLSTKHL GVFPDHVIDM FINGYRLSLT NHGPTPVKEG SKDPRGGIFD   180
AVFTRGDQSK LLTSRHDFKE KNLKEISDLI KKELTEGKAL GLSHTYANVR INHVINLWGA   240
DFDSNGNLKA IYVTDSDSNA SIGMKKYFVG VNSAGKVAIS AKEIKEDNIG AQVLGLFTLS   300
TGQDSWNQTN                                                          310

SEQ ID NO: 3              moltype = AA  length = 310
FEATURE                   Location/Qualifiers
source                    1..310
                          mol_type = protein
                          organism = Streptococcus pyogenes
SEQUENCE: 3
DSFSANQEIR YSEVTPYHVT SVWTKGVTPP ANFTQGEDVF HAPYVANQGW YDITKTFNGK    60
DDLLCGAATA GNMLHWWFDQ NKDQIKRYLE EHPEKQKINF RGEQMFDVKE AIDTKNHQLD   120
SKLFEYFKEK AFPYLSTKHL GVFPDHVIDM FINGYRLSLT NHGPTPVKEG SKDPRGGIFD   180
AVFTRGDQSK LLTSRHDFKE KNLKEISDLI KKELTEGKAL GLSHTYANVR INHVINLWGA   240
DFDSNGNLKA IYVTDSDSNA SIGMKKYFVG VNSAGKVAIS AKEIKEDNIG AQVLGLFTLS   300
TGQDSWNQTN                                                          310

SEQ ID NO: 4              moltype = AA  length = 310
FEATURE                   Location/Qualifiers
source                    1..310
                          mol_type = protein
                          organism = Streptococcus pyogenes
SEQUENCE: 4
DSFSANQEIR YSEVTPYHVT SVWTKGVTPP ANFTQGEDVF HAPYVANQGW YDITKTFNGK    60
DDLLCGAATA GNMLHWWFDQ NKDQIKRYLE EHPEKQKINF KGEQMFDVKE AIDTKNHQLD   120
SKLFEYFKEK AFPYLSTKHL GVFPDHVIDM FINGYRLSLT NHGPTPVKRG SKDPRGGIFD   180
AVFTRGNQSK LLTSRHDFKE KNLKEISDLI KKELTEGKAL GLSHTYANVR INHVINLWGA   240
DFDSNGNLKA IYVTDSDSNA SIGMKKYFVG VNSAGKVAIS AKEIKEDNIG AQVLGLFTLS   300
TGQDSWNQTN                                                          310

SEQ ID NO: 5              moltype = AA  length = 310
FEATURE                   Location/Qualifiers
source                    1..310
                          mol_type = protein
                          organism = Streptococcus pyogenes
SEQUENCE: 5
DSFSANQEIR YSEVTPYHVT SVWTKGVTPP ANFTQGEDVF HAPYVANQGW YDITKTFNGK    60
DDLLCGAATA GNMLHWWFDQ NKDQIKRYLE EHPEKQKINF RGEQMFDVKE AIDTKNHQLD   120
SKLFEYFKEK AFPYLSTKHL GVFPDHVIDM FINGYRLSLT NHGPTPVKKG SKDPRGGIFD   180
AVFTRGNQSK LLTSRHDFKE KNLKEISDLI KKELTEGKAL GLSHTYANVR INHVINLWGA   240
DFDSNGNLKA IYVTDSDSNA SIGMKKYFVG VNKAGKVAIS AKEIKEDNIG AQVLGLFTLS   300
TGQDSWNQTN                                                          310

SEQ ID NO: 6              moltype = AA  length = 310
FEATURE                   Location/Qualifiers
source                    1..310
                          mol_type = protein
                          organism = Streptococcus pyogenes
SEQUENCE: 6
DSFSANQEIR YSEVTPYHVT SVWTKGVTPP ANFTQGEDVF HAPYVANQGW YDITKTFNGK    60
DDLLCGAATA GNMLHWWFDQ NKDQIKRYLR EHPEKQKINF NGEQMFDVKE AIDTKNHQLD   120
SKLFEYFKEK AFPYLSTKHL GVFPDHVIDM FINGYRLSLT NHGPTPVKEG SKDPRGGIFD   180
AVFTRGNQSK LLTSRHDFKE KNLKEISDLI KKELDEGKAL GLSHTYANVR INHVINLWGA   240
DFDSNGNLKA IYVTDSDSNA SIGMKKYFVG VNSAGKVAIS AKEIKEDNIG AQVLGLFTLS   300
TGQDSWNQTN                                                          310

SEQ ID NO: 7              moltype = AA  length = 310
FEATURE                   Location/Qualifiers
source                    1..310
                          mol_type = protein
                          organism = Streptococcus pyogenes
SEQUENCE: 7
DSFSANQEIR YSEVTPYHVT SVWTKGVTPP ANFTQGEDVF HAPYVANQGW YDITKTFNGK    60
DDLLCGAATA GNMLHWWFDQ NKDQIKRYLK EHPEKQKINF NGEQMFDVKE AIRTKNHQLD   120
SKLFEYFKEK AFPYLSTKHL GVFPDHVIDM FINGYRLSLT NHGPTPVKEG SKDPRGGIFD   180
AVFTRGNQSK LLTSRHDFKE KNLKEISDLI KKELEEGKAL GLSHTYANVR INHVINLWGA   240
DFDSNGNLKA IYVTDSDSNA SIGMKKYFVG VNKAGKVAIS AKEIKEDNIG AQVLGLFTLS   300
TGQDSWNQTN                                                          310

SEQ ID NO: 8              moltype = AA  length = 310
FEATURE                   Location/Qualifiers
source                    1..310
                          mol_type = protein
                          organism = Streptococcus pyogenes
```

```
SEQUENCE: 8
DSFSANQEIR YSEVTPYHVT SVWTKGVTPP ANFTQGEDVF HAPYVANQGW YDITKTFNGK    60
DDLLCGAATA GNMLHWWFDQ NKDQIERYLE EHPEKQKINF NGEQMFDVKE AIDTKNHQLD   120
SKLFEYFKEK AFPYLSTKHL GVFPDHVIDM FINGYRLSLT NHGPTPVKEG SKDPRGGIFD   180
AVFTRGNQSK LLTSRHDFKE KNLKEISDLI KEELTKGKAL GLSHTYANVR INHVINLWGA   240
DFDSNGNLKA IYVTDSDSNA SIGMKKYFVG VNSAGKVAIS AKEIKEKNIG AQVLGLFTLS   300
TGQKSWNQTN                                                          310

SEQ ID NO: 9            moltype = AA   length = 310
FEATURE                 Location/Qualifiers
source                  1..310
                        mol_type = protein
                        organism = Streptococcus pyogenes
SEQUENCE: 9
DSFSANQEIR YSEVTPYHVT SVWTKGVTPP ANFTQGEDVF HAPYVANQGW YDITKTFNGK    60
DDLLCGAATA GNMLHWWFDQ NKDQIKRYLK EHPEKQKINF RGEQMFDVKE AIRTKNHQLD   120
SKLFEYFKEK AFPYLSTKHL GVFPDHVIDM FINGYRLSLT NHGPTPVKEG SKDPRGGIFD   180
AVFTRGNQSK LLTSRHDFKE KNLKEISDLI KSELENGKAL GLSHTYANVR INHVINLWGA   240
DFDSNGNLKA IYVTDSDSNA SIGMKKYFVG VNKAGKVAIS AKEIKEDNIG AQVLGLFTLS   300
TGQDSWNQTN                                                          310

SEQ ID NO: 10           moltype = AA   length = 310
FEATURE                 Location/Qualifiers
source                  1..310
                        mol_type = protein
                        organism = Streptococcus pyogenes
SEQUENCE: 10
DSFSANQEIR YSEVTPYHVT SVWTKGVTPP ANFTQGEDVF HAPYVANQGW YDITKTFNGK    60
DDLLCGAATA GNMLHWWFDQ NKDQIKRYLK EHPEKQKINF RGEQMFDVKE AIRTKNHQLD   120
SKLFEYFKEK AFPYLSTKHL GVFPDHVIDM FINGYRLSLT NHGPTPVKKG SKDPRGGIFD   180
AVFTRGNQSK LLTSRHDFKE KNLKEISDLI KKELEEGKAL GLSHTYANVR INHVINLWGA   240
DFDSNGNLKA IYVTDSDSNA SIGMKKYFVG VNSAGKVAIS AKEIKEDNIG AQVLGLFTLS   300
TGQDSWNQTN                                                          310

SEQ ID NO: 11           moltype = AA   length = 310
FEATURE                 Location/Qualifiers
source                  1..310
                        mol_type = protein
                        organism = Streptococcus pyogenes
SEQUENCE: 11
DSFSANQEIR YSEVTPYHVT SVWTKGVTPP ANFTQGEDVF HAPYVANQGW YDITKTFNGK    60
DDLLCGAATA GNMLHWWFDQ NKDQIERYLE EHPEKQKINF RGEQMFDVKE AIDTKNHQLD   120
SKLFEYFKEK AFPYLSTKHL GVFPDHVIDM FINGYRLSLT NHGPTPVKEG SKDPRGGIFD   180
AVFTRGNQSK LLTSRHDFKE KNLKEISDLI KEELTKGKAL GLSHTYANVR INHVINLWGA   240
DFDSNGNLKA IYVTDSDSNA SIGMKKYFVG VNSAGKVAIS AKEIKEDNIG AQVLGLFTLS   300
TGQKSWNQTN                                                          310

SEQ ID NO: 12           moltype = AA   length = 306
FEATURE                 Location/Qualifiers
source                  1..306
                        mol_type = protein
                        organism = Streptococcus pyogenes
SEQUENCE: 12
DSFSANQEIR YSEVTPYHVT SVWTKGVTPP ANFTQGEDVF HAPYVANQGW YDITKTFNGK    60
DDLLCGAATA GNMLHWWFDQ NKDQIKRYLE EHPEKQKINF RGEQMFDVKE AIDTKNHQLD   120
SKLFEYFKEK AFPYLSTKHL GVFPDHVIDM FINGYRLSLT NHGPTPVKEG SKDPRGGIFD   180
AVFTRGDQSK LLTSRHDFKE KNLKEISDLI KKELTEGKAL GLSHTYANVR INHVINLWGA   240
DFDSNGNLKA IYVTDSDSNA SIGMKKYFVG VNSAGKVAIS AKEIKEDNIG AQVLGLFTLS   300
TGQDSW                                                              306

SEQ ID NO: 13           moltype = AA   length = 290
FEATURE                 Location/Qualifiers
source                  1..290
                        mol_type = protein
                        organism = Streptococcus pyogenes
SEQUENCE: 13
SVWTKGVTPP ANFTQGEDVF HAPYVANQGW YDITKTFNGK DDLLCGAATA GNMLHWWFDQ    60
NKDQIKRYLE EHPEKQKINF NGEQMFDVKE AIDTKNHQLD SKLFEYFKEK AFPYLSTKHL   120
GVFPDHVIDM FINGYRLSLT NHGPTPVKEG SKDPRGGIFD AVFTRGDQSK LLTSRHDFKE   180
KNLKEISDLI KKELTEGKAL GLSHTYANVR INHVINLWGA DFDSNGNLKA IYVTDSDSNA   240
SIGMKKYFVG VNSAGKVAIS AKEIKEDNIG AQVLGLFTLS TGQDSWNQTN              290

SEQ ID NO: 14           moltype = AA   length = 290
FEATURE                 Location/Qualifiers
source                  1..290
                        mol_type = protein
                        organism = Streptococcus pyogenes
SEQUENCE: 14
SVWTKGVTPP ANFTQGEDVF HAPYVANQGW YDITKTFNGK DDLLCGAATA GNMLHWWFDQ    60
```

```
NKDQIKRYLE EHPEKQKINF KGEQMFDVKE AIDTKNHQLD SKLFEYFKEK AFPYLSTKHL    120
GVFPDHVIDM FINGYRLSLT NHGPTPVKEG SKDPRGGIFD AVFTRGNQSK LLTSRHDFKE    180
KNLKEISDLI KKELTEGKAL GLSHTYANVR INHVINLWGA DFDSNGNLKA IYVTDSDSNA    240
SIGMKKYFVG VNSAGKVAIS AKEIKEDNIG AQVLGLFTLS TGQDSWNQTN               290

SEQ ID NO: 15           moltype = AA   length = 290
FEATURE                 Location/Qualifiers
source                  1..290
                        mol_type = protein
                        organism = Streptococcus pyogenes
SEQUENCE: 15
SVWTKGVTPP ANFTQGEDVF HAPYVANQGW YDITKTFNGK DDLLCGAATA GNMLHWWFDQ     60
NKDQIERYLE EHPEKQKINF KGEQMFDVKK AIDTKNHQLD SKLFEYFKEK AFPYLSTKHL    120
GVFPDHVIDM FINGYRLSLT NHGPTPVKEG SKDPRGGIFD AVFTRGNQSK LLTSRHDFKE    180
KNLKEISDLI KEELTKGKAL GLSHTYANVR INHVINLWGA DFDSNGNLKA IYVTDSDSNA    240
SIGMKKYFVG VNSAGKVAIS AKEIKEDNIG AQVLGLFTLS TGQKSWNQTN               290

SEQ ID NO: 16           moltype = AA   length = 319
FEATURE                 Location/Qualifiers
source                  1..319
                        mol_type = protein
                        organism = Streptococcus pyogenes
SEQUENCE: 16
DDYQRNATEA YAKEVPHQIT SVWTKGVTPP ANFTQGEDVF HAPYVANQGW YDITKTFNGK     60
DDLLCGAATA GNMLHWWFDQ NKDQIERYLE EHPEKQKINF KGEQMFDVKK AIDTKNHQLD    120
SKLFEYFKEK AFPYLSTKHL GVFPDHVIDM FINGYRLSLT NHGPTPVKEG SKDPRGGIFD    180
AVFTRGNQSK LLTSRHDFKE KNLKEISDLI KEELTKGKAL GLSHTYANVR INHVINLWGA    240
DFDSNGNLKA IYVTDSDSNA SIGMKKYFVG VNSAGKVAIS AKEIKEDNIG AQVLGLFTLS    300
TGQKSWNQTN GGGHHHHHH                                                 319

SEQ ID NO: 17           moltype = AA   length = 320
FEATURE                 Location/Qualifiers
source                  1..320
                        mol_type = protein
                        organism = Streptococcus pyogenes
SEQUENCE: 17
MDSFSANQEI RYSEVTPYHV TSVWTKGVTP PANFTQGEDV FHAPYVANQG WYDITKTFNG     60
KDDLLCGAAT AGNMLHWWFD QNKDQIKRYL EEHPEKQKIN FNGEQMFDVK EAIDTKNHQL    120
DSKLFEYFKE KAFPYLSTKH LGVFPDHVID MFINGYRLSL TNHGPTPVKE GSKDPRGGIF    180
DAVFTRGDQS KLLTSRHDFK EKNLKEISDL IKKELTEGKA LGLSHTYANV RINHVINLWG    240
ADFDSNGNLK AIYVTDSDSN ASIGMKKYFV GVNSAGKVAI SAKEIKEDNI GAQVLGLFTL    300
STGQDSWNQT NGGGHHHHHH                                                320

SEQ ID NO: 18           moltype = AA   length = 4
FEATURE                 Location/Qualifiers
source                  1..4
                        mol_type = protein
                        organism = Streptococcus pyogenes
SEQUENCE: 18
NQTN                                                                   4

SEQ ID NO: 19           moltype = AA   length = 20
FEATURE                 Location/Qualifiers
source                  1..20
                        mol_type = protein
                        organism = Streptococcus pyogenes
SEQUENCE: 19
DSFSANQEIR YSEVTPYHVT                                                 20

SEQ ID NO: 20           moltype = DNA   length = 963
FEATURE                 Location/Qualifiers
source                  1..963
                        mol_type = genomic DNA
                        organism = Streptococcus pyogenes
SEQUENCE: 20
atggatagtt tttctgctaa tcaagagatt agatattcgg aagtaacacc ttatcacgtt     60
acttccgttt ggaccaaagg agttactcct ccagcaaact tcactcaagg tgaagatgtt    120
tttcacgctc cttatgttgc taaccaagga tggtatgata ttaccaaaac attcaatgga    180
aaagacgatc ttctttgcgg ggctgccaca gcagggaata tgcttcactg gtggttcgat    240
caaaacaaag accaaattaa acgttatttg gaagagcatc cagaaaagca aaaaataaac    300
ttcaatggcg aacagatgtt tgacgtaaaa gaagctatcg acactaaaaa ccaccagcta    360
gatagtaaat tatttgaata ttttaagaa aaagctttcc cttatctatc tactaaacac    420
ctaggagttt ttcctgatca tgtaattgat atgttcatta cggctaccg ccttagtcta    480
actaaccacg gtccaacgcc agtaaaagaa ggtagtaaag atccccgagg tggtattttt    540
gacgccgtat ttacaagagg tgatcaaagt aagctattga caagtcgtca tgattttaaa    600
gaaaaaaatc tcaagaaaat cagtgatctt attaagaaag agttaaccga aggcaaggct    660
ctaggcctat cacacaccta cgctaacgta cgcatcaacc atgttataaa cctgtgggga    720
gctgactttg attctaacgg gaaccttaaa gctatttatg taacagactc tgatagtaat    780
gcatctattg gtatgaagaa atactttgtt ggtgttaatt ccgctggaaa agtagctatt    840
```

```
tctgctaaag aaataaaaga agataatata ggtgctcaag tactagggtt atttacactt    900
tcaacagggc aagatagttg gaatcagacc aatggcggtg gccatcatca ccatcaccac    960
taa                                                                  963

SEQ ID NO: 21            moltype = DNA   length = 963
FEATURE                  Location/Qualifiers
source                   1..963
                         mol_type = genomic DNA
                         organism = Streptococcus pyogenes
SEQUENCE: 21
atggatagtt tttctgctaa tcaagagatt agatattcgg aagtaacacc ttatcacgtt     60
acttccgttt ggaccaaagg agttactcct ccagcaaact tcactcaagg tgaagatgtt    120
tttcacgctc cttatgttgc taaccaagga tggtatgata ttaccaaaac attcaatgga    180
aaagacgatc ttctttgcgg ggctgccaca gcagggaata tgcttcactg gtggttcgat    240
caaaacaaag accaaattaa acgttatttg gaagagcatc cagaaaagca aaaaataaac    300
ttccgtggcg aacagatgtt tgacgtaaaa gaagctatcg acactaaaaa ccaccagcta    360
gatagtaaat tatttgaata ttttaaagaa aaagcttttcc cttatctatc tactaaaac     420
ctaggagttt tccctgatca tgtaattgat atgttcatta acggctaccg ccttagtcta    480
actaaccacg gtccaacgcc agtaaaagaa ggtagtaaag atccccgagg tggtattttt    540
gacgccgtat ttacaagagg tgatcaaagt aagctattga caagtcgtca tgatttttaaa   600
gaaaaaaatc tcaagaaaat cagtgatctc attaagaaag agttaaccga aggcaaggct    660
ctaggcctat cacacaccta cgctaacgta cgcatcaacc atgttataaa cctgtgggga    720
gctgactttg attctaacgg gaaccttaaa gctatttatg taacagactc tgatagtaat    780
gcatctattg gtatgaagaa atactttgtt ggtgttaatt ccgctggaaa agtagctatt    840
tctgctaaag aaataaaaga agataatata ggtgctcaag tactagggtt atttacactt    900
tcaacagggc aagatagttg gaatcagacc aatggcggtg gccatcatca ccatcaccac    960
taa                                                                  963

SEQ ID NO: 22            moltype = DNA   length = 963
FEATURE                  Location/Qualifiers
source                   1..963
                         mol_type = genomic DNA
                         organism = Streptococcus pyogenes
SEQUENCE: 22
atggatagtt tttctgctaa tcaagagatt agatattcgg aagtaacacc ttatcacgtt     60
acttccgttt ggaccaaagg agttactcct ccagcaaact tcactcaagg tgaagatgtt    120
tttcacgctc cttatgttgc taaccaagga tggtatgata ttaccaaaac attcaatgga    180
aaagacgatc ttctttgcgg ggctgccaca gcagggaata tgcttcactg gtggttcgat    240
caaaacaaag accaaattaa acgttatttg gaagagcatc cagaaaagca aaaaataaac    300
ttcaaaggcg aacagatgtt tgacgtaaaa gaagctatcg acactaaaaa ccaccagcta    360
gatagtaaat tatttgaata ttttaaagaa aaagcttttcc cttatctatc tactaaaac     420
ctaggagttt tccctgatca tgtaattgat atgttcatta acggctaccg ccttagtcta    480
actaaccacg gtccaacgcc agtaaaacgt ggtagtaaag atccccgagg tggtattttt    540
gacgccgtat ttacaagagg taaccaaagt aagctattga caagtcgtca tgatttttaaa   600
gaaaaaaatc tcaagaaaat cagtgatctc attaagaaag agttaaccga aggcaaggct    660
ctaggcctat cacacaccta cgctaacgta cgcatcaacc atgttataaa cctgtgggga    720
gctgactttg attctaacgg gaaccttaaa gctatttatg taacagactc tgatagtaat    780
gcatctattg gtatgaagaa atactttgtt ggtgttaatt ccgctggaaa agtagctatt    840
tctgctaaag aaataaaaga agataatata ggtgctcaag tactagggtt atttacactt    900
tcaacagggc aagatagttg gaatcagacc aatggcggtg gccatcatca ccatcaccac    960
taa                                                                  963

SEQ ID NO: 23            moltype = DNA   length = 963
FEATURE                  Location/Qualifiers
source                   1..963
                         mol_type = genomic DNA
                         organism = Streptococcus pyogenes
SEQUENCE: 23
atggatagtt tttctgctaa tcaagagatt agatattcgg aagtaacacc ttatcacgtt     60
acttccgttt ggaccaaagg agttactcct ccagcaaact tcactcaagg tgaagatgtt    120
tttcacgctc cttatgttgc taaccaagga tggtatgata ttaccaaaac attcaatgga    180
aaagacgatc ttctttgcgg ggctgccaca gcagggaata tgcttcactg gtggttcgat    240
caaaacaaag accaaattaa acgttatttg gaagagcatc cagaaaagca aaaaataaac    300
ttccgtggcg aacagatgtt tgacgtaaaa gaagctatcg acactaaaaa ccaccagcta    360
gatagtaaat tatttgaata ttttaaagaa aaagcttttcc cttatctatc tactaaaac     420
ctaggagttt tccctgatca tgtaattgat atgttcatta acggctaccg ccttagtcta    480
actaaccacg gtccaacgcc agtaaaaaaa ggtagtaaag atccccgagg tggtattttt    540
gacgccgtat ttacaagagg taaccaaagt aagctattga caagtcgtca tgatttttaaa   600
gaaaaaaatc tcaagaaaat cagtgatctc attaagaaag agttaaccga aggcaaggct    660
ctaggcctat cacacaccta cgctaacgta cgcatcaacc atgttataaa cctgtgggga    720
gctgactttg attctaacgg gaaccttaaa gctatttatg taacagactc tgatagtaat    780
gcatctattg gtatgaagaa atactttgtt ggtgttaata agctggaaa agtagctatt     840
tctgctaaag aaataaaaga agataatata ggtgctcaag tactagggtt atttacactt    900
tcaacagggc aagatagttg gaatcagacc aatggcggtg gccatcatca ccatcaccac    960
taa                                                                  963

SEQ ID NO: 24            moltype = DNA   length = 963
FEATURE                  Location/Qualifiers
source                   1..963
```

```
                    mol_type = genomic DNA
                    organism = Streptococcus pyogenes
SEQUENCE: 24
atggatagtt tttctgctaa tcaagagatt agatattcgg aagtaacacc ttatcacgtt   60
acttccgttt ggaccaaagg agttactcct ccagcaaact tcactcaagg tgaagatgtt  120
tttcacgctc cttatgttgc taaccaagga tggtatgata ttaccaaaac attcaatgga  180
aaagacgatc ttctttgcgg ggctgccaca gcagggaata tgcttcactg gtggttcgat  240
caaaacaaag accaaattaa acgttatttg cgtgagcatc cagaaaagca aaaaataaac  300
ttcaatggcg aacagatgtt tgacgtaaaa gaagctatcg acactaaaaa ccaccagcta  360
gatagtaaat tatttgaata ttttaaagaa aaagctttcc cttatctatc tactaaaaac  420
ctaggagttt tccctgatca tgtaattgat atgttcatta acggctaccg ccttagtcta  480
actaaccacg tccaacgcc agtaaaagaa ggtagtaaag atccccgagg tggtattttt   540
gacgccgtat ttacaagagg taaccaaagt aagctattga caagtcgtca tgattttaaa  600
gaaaaaaatc tcaaagaaat cagtgatctc attaagaaag agttagatga aggcaaggct  660
ctaggcctat cacacaccta cgctaacgta cgcatcaacc atgttataaa cctgtgggga  720
gctgactttg attctaacgg gaaccttaaa gctatttatg taacagactc tgatagtaat  780
gcatctattg gtatgaagaa atactttgtt ggtgttaatt ccgctggaaa agtagctatt  840
tctgctaaag aaataaaaga agataatata ggtgctcaag tactagggtt atttacactt  900
tcaacagggc aagatagttg gaatcagacc aatggcggtg ccatcatca ccatcaccac   960
taa                                                                963

SEQ ID NO: 25        moltype = DNA   length = 963
FEATURE              Location/Qualifiers
source               1..963
                     mol_type = genomic DNA
                     organism = Streptococcus pyogenes
SEQUENCE: 25
atggatagtt tttctgctaa tcaagagatt agatattcgg aagtaacacc ttatcacgtt   60
acttccgttt ggaccaaagg agttactcct ccagcaaact tcactcaagg tgaagatgtt  120
tttcacgctc cttatgttgc taaccaagga tggtatgata ttaccaaaac attcaatgga  180
aaagacgatc ttctttgcgg ggctgccaca gcagggaata tgcttcactg gtggttcgat  240
caaaacaaag accaaattaa acgttatttg aaagagcatc cagaaaagca aaaaataaac  300
ttcaatggcg aacagatgtt tgacgtaaaa gaagctatcc gtactaaaaa ccaccagcta  360
gatagtaaat tatttgaata ttttaaagaa aaagcttttcc cttatctatt tactaaaaac  420
ctaggagttt tccctgatca tgtaattgat atgttcatta acggctaccg ccttagtcta  480
actaaccacg tccaacgcc agtaaaagaa ggtagtaaag atccccgagg tggtattttt   540
gacgccgtat ttacaagagg taaccaaagt aagctattga caagtcgtca tgattttaaa  600
gaaaaaaatc tcaaagaaat cagtgatctc attaagaaag agttagaaga aggcaaggct  660
ctaggcctat cacacaccta cgctaacgta cgcatcaacc atgttataaa cctgtgggga  720
gctgactttg attctaacgg gaaccttaaa gctatttatg taacagactc tgatagtaat  780
gcatctattg gtatgaagaa atactttgtt ggtgttaata agctggaaa agtagctatt  840
tctgctaaag aaataaaaga agataatata ggtgctcaag tactagggtt atttacactt  900
tcaacagggc aagatagttg gaatcagacc aatggcggtg ccatcatca ccatcaccac   960
taa                                                                963

SEQ ID NO: 26        moltype = DNA   length = 963
FEATURE              Location/Qualifiers
source               1..963
                     mol_type = genomic DNA
                     organism = Streptococcus pyogenes
SEQUENCE: 26
atggatagtt tttctgctaa tcaagagatt agatattcgg aagtaacacc ttatcacgtt   60
acttccgttt ggaccaaagg agttactcct ccagcaaact tcactcaagg tgaagatgtt  120
tttcacgctc cttatgttgc taaccaagga tggtatgata ttaccaaaac attcaatgga  180
aaagacgatc ttctttgcgg ggctgccaca gcagggaata tgcttcactg gtggttcgat  240
caaaacaaag accaaattaa acgttatttg gaagagcatc cagaaaagca aaaaataaac  300
ttcaatggcg aacagatgtt tgacgtaaaa gaagctatcg acactaaaaa ccaccagcta  360
gatagtaaat tatttgaata ttttaaagaa aaagctttcc cttatctatc tactaaaaac  420
ctaggagttt tccctgatca tgtaattgat atgttcatta acggctaccg ccttagtcta  480
actaaccacg tccaacgcc agtaaaagaa ggtagtaaag atccccgagg tggtattttt   540
gacgccgtat ttacaagagg taaccaaagt aagctattga caagtcgtca tgattttaaa  600
gaaaaaaatc tcaaagaaat cagtgatctc attaagaaag agttaaccaa aggcaaggct  660
ctaggcctat cacacaccta cgctaacgta cgcatcaacc atgttataaa cctgtgggga  720
gctgactttg attctaacgg gaaccttaaa gctatttatg taacagactc tgatagtaat  780
gcatctattg gtatgaagaa atactttgtt ggtgttaatt ccgctggaaa agtagctatt  840
tctgctaaag aaataaaaga aaaaatata ggtgctcaag tactagggtt atttacactt   900
tcaacagggc aaaaagttg gaatcagacc aatggcggtg ccatcatca ccatcaccac   960
taa                                                                963

SEQ ID NO: 27        moltype = DNA   length = 963
FEATURE              Location/Qualifiers
source               1..963
                     mol_type = genomic DNA
                     organism = Streptococcus pyogenes
SEQUENCE: 27
atggatagtt tttctgctaa tcaagagatt agatattcgg aagtaacacc ttatcacgtt   60
acttccgttt ggaccaaagg agttactcct ccagcaaact tcactcaagg tgaagatgtt  120
tttcacgctc cttatgttgc taaccaagga tggtatgata ttaccaaaac attcaatgga  180
aaagacgatc ttctttgcgg ggctgccaca gcagggaata tgcttcactg gtggttcgat  240
```

```
caaaacaaag accaaattaa acgttatttg aaagagcatc cagaaaagca aaaaataaac   300
ttccgtggcg aacagatgtt tgacgtaaaa gaagctatcc gtactaaaaa ccaccagcta   360
gatagtaaat tatttgaata ttttaaagaa aaagctttcc cttatctatc tactaaacac   420
ctaggagttt tccctgatca tgtaattgat atgttcatta acggctaccg ccttagtcta   480
actaaccacg gtccaacgcc agtaaaaaga ggtagtaaag atccccgagg tggtattttt   540
gacgccgtat ttacaagagg taaccaaagt aagctattga caagtcgtca tgattttaaa   600
gaaaaaaatc tcaaagaaat cagtgatctc attaagagtg agttagaaaa cggcaaggct   660
ctaggcctat cacacaccta cgctaacgta cgcatcaacc atgttataaa cctgtgggga   720
gctgactttg attctaacgg gaaccttaaa gctatttatg taacagactc tgatagtaat   780
gcatctattg gtatgaagaa atactttgtt ggtgttaata aagctggaaa agtagctatt   840
tctgctaaag aaataaaaga agataatata ggtgctcaag tactagggtt atttacactt   900
tcaacagggc aagatagttg gaatcagacc aatggcggtg ccatcatca ccatcaccac   960
taa                                                                963

SEQ ID NO: 28        moltype = DNA   length = 963
FEATURE              Location/Qualifiers
source               1..963
                     mol_type = genomic DNA
                     organism = Streptococcus pyogenes
SEQUENCE: 28
atggatagtt tttctgctaa tcaagagatt agatattcgg aagtaacacc ttatcacgtt    60
acttccgttt ggaccaaagg agttactcct ccagcaaact tcactcaagg tgaagatgtt   120
tttcacgctc cttatgttgc taaccaagga tggtatgata ttaccaaaac attcaatgga   180
aaagacgatc ttctttgcgg ggctgccaca gcagggaata tgcttcactg gtggttcgat   240
caaaacaaag accaaattaa acgttatttg aaagagcatc cagaaaagca aaaaataaac   300
ttccgtggcg aacagatgtt tgacgtaaaa gaagctatcc gtactaaaaa ccaccagcta   360
gatagtaaat tatttgaata ttttaaagaa aaagctttcc cttatctatc tactaaacac   420
ctaggagttt tccctgatca tgtaattgat atgttcatta acggctaccg ccttagtcta   480
actaaccacg gtccaacgcc agtaaaaaaa ggtagtaaag atccccgagg tggtattttt   540
gacgccgtat ttacaagagg taaccaaagt aagctattga caagtcgtca tgattttaaa   600
gaaaaaaatc tcaaagaaat cagtgatctc attaagaaag agttagaaga aggcaaggct   660
ctaggcctat cacacaccta cgctaacgta cgcatcaacc atgttataaa cctgtgggga   720
gctgactttg attctaacgg gaaccttaaa gctatttatg taacagactc tgatagtaat   780
gcatctattg gtatgaagaa atactttgtt ggtgttaatt ccgctggaaa agtagctatt   840
tctgctaaag aaataaaaga agataatata ggtgctcaag tactagggtt atttacactt   900
tcaacagggc aagatagttg gaatcagacc aatggcggtg ccatcatca ccatcaccac   960
taa                                                                963

SEQ ID NO: 29        moltype = DNA   length = 963
FEATURE              Location/Qualifiers
source               1..963
                     mol_type = genomic DNA
                     organism = Streptococcus pyogenes
SEQUENCE: 29
atggatagtt tttctgctaa tcaagagatt agatattcgg aagtaacacc ttatcacgtt    60
acttccgttt ggaccaaagg agttactcct ccagcaaact tcactcaagg tgaagatgtt   120
tttcacgctc cttatgttgc taaccaagga tggtatgata ttaccaaaac attcaatgga   180
aaagacgatc ttctttgcgg ggctgccaca gcagggaata tgcttcactg gtggttcgat   240
caaaacaaag accaaattga acgttatttg gaagagcatc cagaaaagca aaaaataaac   300
ttccgtggcg aacagatgtt tgacgtaaaa gaagctatcg acactaaaaa ccaccagcta   360
gatagtaaat tatttgaata ttttaaagaa aaagctttcc cttatctatc tactaaacac   420
ctaggagttt tccctgatca tgtaattgat atgttcatta acggctaccg ccttagtcta   480
actaaccacg gtccaacgcc agtaaaaaaa ggtagtaaag atccccgagg tggtattttt   540
gacgccgtat ttacaagagg taaccaaagt aagctattga caagtcgtca tgattttaaa   600
gaaaaaaatc tcaaagaaat cagtgatctc attaaggaag agttaaccaa aggcaaggct   660
ctaggcctat cacacaccta cgctaacgta cgcatcaacc atgttataaa cctgtgggga   720
gctgactttg attctaacgg gaaccttaaa gctatttatg taacagactc tgatagtaat   780
gcatctattg gtatgaagaa atactttgtt ggtgttaatt ccgctggaaa agtagctatt   840
tctgctaaag aaataaaaga agataatata ggtgctcaag tactagggtt atttacactt   900
tcaacagggc aaaaagttg gaatcagacc aatggcggtg ccatcatca ccatcaccac    960
taa                                                                963

SEQ ID NO: 30        moltype = DNA   length = 957
FEATURE              Location/Qualifiers
source               1..957
                     mol_type = genomic DNA
                     organism = Streptococcus pyogenes
SEQUENCE: 30
atggatagtt tttctgctaa tcaagagatt agatattcgg aagtaacacc ttatcacgtt    60
acttccgttt ggaccaaagg agttactcct ccagcaaact tcactcaagg tgaagatgtt   120
tttcacgctc cttatgttgc taaccaagga tggtatgata ttaccaaaac attcaatgga   180
aaagacgatc ttctttgcgg ggctgccaca gcagggaata tgcttcactg gtggttcgat   240
caaaacaaag accaaattaa acgttatttg gaagagcatc cagaaaagca aaaaataaac   300
ttcaatggcg aacagatgtt tgacgtaaaa gaagctatcc gtactaaaaa ccaccagcta   360
gatagtaaat tatttgaata ttttaaagaa aaagctttcc cttatctatc tactaaacac   420
ctaggagttt tccctgatca tgtaattgat atgttcatta acggctaccg ccttagtcta   480
actaaccacg gtccaacgcc agtaaaagaa ggtagtaaag atccccgagg tggtattttt   540
gacgccgtat ttacaagagg tgatcaaagt aagctattga caagtcgtca tgattttaaa   600
gaaaaaaatc tcaaagaaat cagtgatctc attaagaaag agttaaccga aggcaaggct   660
```

```
ctaggcctat cacacaccta cgctaacgta cgcatcaacc atgttataaa cctgtgggga   720
gctgactttg attctaacgg gaaccttaaa gctatttatg taacagactc tgatagtaat   780
gcatctattg gtatgaagaa atactttgtt ggtgttaatt ccgctggaaa agtagctatt   840
tctgctaaag aaataaaaga agataatata ggtgctcaag tactagggtt atttacactt   900
tcaacagggc aagatagttg gggtggcggc ggtggccatc atcaccatca ccactaa     957
```

SEQ ID NO: 31              moltype = DNA   length = 903
FEATURE                    Location/Qualifiers
source                     1..903
                           mol_type = genomic DNA
                           organism = Streptococcus pyogenes
SEQUENCE: 31
```
atgtccgttt ggaccaaagg agttactcct ccagcaaaact tcactcaagg tgaagatgtt   60
tttcacgctc cttatgttgc taaccaagga tggtatgata ttaccaaaac attcaatgga   120
aaagacgatc ttctttgcgg ggctgccaca gcagggaata tgcttcactg gtggttcgat   180
caaaacaaag accaaattaa acgttatttg gaagagcatc cagaaaagca aaaaataaac   240
ttcaatggcg aacagatgtt tgacgtaaaa gaagctatcg acactaaaaa ccaccagcta   300
gatagtaaat tatttgaata ttttaaagaa aaagctttcc cttatctatc tactaaacac   360
ctaggagttt ccctgatca tgtaattgat atgttcatta acggctaccg ccttagtcta   420
actaaccacg gtccaacgcc agtaaaagaa ggtagtaaag atccccgagg tggtattttt   480
gacgccgtat ttacaagagg tgatcaaagt aagctattga caagtcgtca tgattttaaa   540
gaaaaaaatc tcaaagaaat cagtgatctc attaagaaag agttaaccga aggcaaggct   600
ctaggcctat cacacaccta cgctaacgta cgcatcaacc atgttataaa cctgtgggga   660
gctgactttg attctaacgg gaaccttaaa gctatttatg taacagactc tgatagtaat   720
gcatctattg gtatgaagaa atactttgtt ggtgttaatt ccgctggaaa agtagctatt   780
tctgctaaag aaataaaaga agataatata ggtgctcaag tactagggtt atttacactt   840
tcaacagggc aagatagttg gaatcagacc aatggcggtg ccatcatca ccatcaccac   900
taa                                                                903
```

SEQ ID NO: 32              moltype = DNA   length = 903
FEATURE                    Location/Qualifiers
source                     1..903
                           mol_type = genomic DNA
                           organism = Streptococcus pyogenes
SEQUENCE: 32
```
atgtccgttt ggaccaaagg agttactcct ccagcaaact tcactcaagg tgaagatgtt   60
tttcacgctc cttatgttgc taaccaagga tggtatgata ttaccaaaac attcaatgga   120
aaagacgatc ttctttgcgg ggctgccaca gcagggaata tgcttcactg gtggttcgat   180
caaaacaaag accaaattaa acgttatttg gaagagcatc cagaaaagca aaaaataaac   240
ttcaaaggcg aacagatgtt tgacgtaaaa gaagctatcg acactaaaaa ccaccagcta   300
gatagtaaat tatttgaata ttttaaagaa aaagctttcc cttatctatc tactaaacac   360
ctaggagttt ccctgatca tgtaattgat atgttcatta acggctaccg ccttagtcta   420
actaaccacg gtccaacgcc agtaaaagaa ggtagtaaag atccccgagg tggtattttt   480
gacgccgtat ttacaagagg taaccaaagt aagctattga caagtcgtca tgattttaaa   540
gaaaaaaatc tcaaagaaat cagtgatctc attaagaaag agttaaccga aggcaaggct   600
ctaggcctat cacacaccta cgctaacgta cgcatcaacc atgttataaa cctgtgggga   660
gctgactttg attctaacgg gaaccttaaa gctatttatg taacagactc tgatagtaat   720
gcatctattg gtatgaagaa atactttgtt ggtgttaatt ccgctggaaa agtagctatt   780
tctgctaaag aaataaaaga agataatata ggtgctcaag tactagggtt atttacactt   840
tcaacagggc aagatagttg gaatcagacc aatggcggtg ccatcatca ccatcaccac   900
taa                                                                903
```

SEQ ID NO: 33              moltype = DNA   length = 903
FEATURE                    Location/Qualifiers
source                     1..903
                           mol_type = genomic DNA
                           organism = Streptococcus pyogenes
SEQUENCE: 33
```
atgtccgttt ggaccaaagg agttactcct ccagcaaact tcactcaagg tgaagatgtt   60
tttcacgctc cttatgttgc taaccaagga tggtatgata ttaccaaaac attcaatgga   120
aaagacgatc ttctttgcgg ggctgccaca gcagggaata tgcttcactg gtggttcgat   180
caaaacaaag accaaattga acgttatttg gaagagcatc cagaaaagca aaaaataaac   240
ttcaaaggcg aacagatgtt tgacgtaaaa aaagctatcg acactaaaaa ccaccagcta   300
gatagtaaat tatttgaata ttttaaagaa aaagctttcc cttatctatc tactaaacac   360
ctaggagttt ccctgatca tgtaattgat atgttcatta acggctaccg ccttagtcta   420
actaaccacg gtccaacgcc agtaaaagaa ggtagtaaag atccccgagg tggtattttt   480
gacgccgtat ttacaagagg taaccaaagt aagctattga caagtcgtca tgattttaaa   540
gaaaaaaatc tcaaagaaat cagtgatctc attaaggaag agttaaccaa aggcaaggct   600
ctaggcctat cacacaccta cgctaacgta cgcatcaacc atgttataaa cctgtgggga   660
gctgactttg attctaacgg gaaccttaaa gctatttatg taacagactc tgatagtaat   720
gcatctattg gtatgaagaa atactttgtt ggtgttaatt ccgctggaaa agtagctatt   780
tctgctaaag aaataaaaga agataatata ggtgctcaag tactagggtt atttacactt   840
tcaacagggc aaaaagttg gaatcagacc aatggcggtg ccatcatca ccatcaccac   900
taa                                                                903
```

SEQ ID NO: 34              moltype = DNA   length = 963
FEATURE                    Location/Qualifiers
source                     1..963
                           mol_type = genomic DNA

```
                        organism = Streptococcus pyogenes
SEQUENCE: 34
atggacgatt accaaggaa tgctacggaa gcttatgcca aagaagtacc acatcagatc   60
acttccgttt ggaccaaagg agttactcct ccagcaaact tcactcaagg tgaagatgtt  120
tttcacgctc cttatgttgc taaccaagga tggtatgata ttaccaaaac attcaatgga  180
aaagacgatc ttctttgcgg ggctgccaca gcagggaata tgcttcactg gtggttcgat  240
caaaacaaag accaaattga acgttatttg gaagagcatc cagaaaagca aaaaataaac  300
ttcaaaggcg aacagatgtt tgacgtaaaa aaagctatcg acactaaaaa ccaccagcta  360
gatagtaaat tatttgaata ttttaaagaa aaagctttcc cttatctatc tactaaacac  420
ctaggagttt tccctgatca tgtaattgat atgttcatta acggctaccg ccttagtcta  480
actaaccacg gtccaacgcc agtaaaagaa ggtagtaaag atccccgagg tggtattttt  540
gacgccgtat ttacaagagg taaccaaagt aagctattga caagtcgtca tgattttaaa  600
gaaaaaaatc tcaaagaaat cagtgatctc attaaggaag agttaaccaa aggcaaggct  660
ctaggcctat cacacaccta cgctaacgta cgcatcaacc atgttataaa cctgtgggga  720
gctgactttg attctaacgg gaaccttaaa gctatttatg taacagactc tgatagtaat  780
gcatctattg gtatgaagaa atactttgtt ggtgttaatt ccgctggaaa agtagctatt  840
tctgctaaag aaataaaaga agataatata ggtgctcaag tactagggtt atttacactt  900
tcaacagggc aaaaaagttg gaatcagacc aatggcggtg gccatcatca ccatcaccac  960
taa                                                              963

SEQ ID NO: 35              moltype = AA  length = 19
FEATURE                    Location/Qualifiers
source                     1..19
                           mol_type = protein
                           organism = Streptococcus pyogenes
SEQUENCE: 35
SFSANQEIRY SEVTPYHVT                                                19

SEQ ID NO: 36              moltype = AA  length = 19
FEATURE                    Location/Qualifiers
source                     1..19
                           mol_type = protein
                           organism = Streptococcus pyogenes
SEQUENCE: 36
DYQRNATEAY AKEVPHQIT                                                19

SEQ ID NO: 37              moltype = AA  length = 20
FEATURE                    Location/Qualifiers
source                     1..20
                           mol_type = protein
                           organism = Streptococcus pyogenes
SEQUENCE: 37
DDYQRNATEA YAKEVPHQIT                                               20
```

CYSTEINE PROTEASE

CROSS-REFERENCE TO RELATED APPLICATIONS

This application is a continuation of U.S. Non-Provisional application Ser. No. 17/644,315 filed Dec. 14, 2021, which is a continuation of U.S. Non-Provisional application Ser. No. 16/879,324 filed May 20, 2020, granted as U.S. Pat. No. 11,214,784 issued Jan. 4, 2022, which is a continuation of U.S. Non-Provisional application Ser. No. 15/550,309 filed Aug. 10, 2017, granted as U.S. Pat. No. 10,696,959 issued Jun. 30, 2020, which is a national phase application under 35 U.S.C. § 371 that claims priority to International Application No. PCT/EP2016/053052 filed Feb. 12, 2016, which claims priority to Great Britain Patent Application No. 1502306.2, Feb. 12, 2015, all of which are incorporated herein by reference in their entirety.

INCORPORATION OF SEQUENCE LISTING

The instant application contains a Sequence Listing, named "SeqLst_KEMPP0066USC3.xml" (52,504 bytes) which has been submitted electronically in XML format and is hereby incorporated by reference in its entirety.

FIELD OF THE INVENTION

The present invention relates to a novel polypeptide which displays IgG cysteine protease activity, and in vivo and ex vivo uses thereof. Uses of the polypeptide include methods for the prevention or treatment of diseases and conditions mediated by IgG, and methods for the analysis of IgG.

BACKGROUND OF THE INVENTION

IdeS (Immunoglobulin G-degrading enzyme of *S. pyogenes*) is an extracellular cysteine protease produced by the human pathogen *S. pyogenes*. IdeS was originally isolated from a group A *Streptococcus* strain of serotype M1, but the ides gene has now been identified in all tested group A *Streptococcus* strains. IdeS has an extraordinarily high degree of substrate specificity, with its only identified substrate being IgG. IdeS catalyses a single proteolytic cleavage in the lower hinge region of the heavy chains of all subclasses of human IgG. IdeS also catalyses an equivalent cleavage of the heavy chains of some subclasses of IgG in various animals. IdeS efficiently cleaves IgG to Fc and F(ab')$_2$ fragments via a two-stage mechanism. In the first stage, one (first) heavy chain of IgG is cleaved to generate a single cleaved IgG (scIgG) molecule with a non-covalently bound Fc molecule. The scIgG molecule is effectively an intermediate product which retains the remaining (second) heavy chain of the original IgG molecule. In the second stage of the mechanism this second heavy chain is cleaved by IdeS to release a F(ab')$_2$ fragment and a homodimeric Fc fragment. These are the products generally observed under physiological conditions. Under reducing conditions the F(ab')$_2$ fragment may dissociate to two Fab fragments and the homodimeric Fc may dissociate into its component monomers.

SUMMARY OF THE INVENTION

The IgG cleaving ability of IdeS has been shown to have utility ex vivo, for example in methods for production of Fab and Fc fragments, which may be used for the analysis of IgG. See, for example, WO2003051914 and WO2009033670. IdeS has also been shown to have in vivo utility as a therapeutic agent, since it is capable of the in vivo cleavage of IgG molecules which mediate disease or which are otherwise undesirable. See, for example, WO2003051914, WO2006131347 and WO2013110946. IdeS may be used as a therapy for any disease or condition wholly or partly mediated by IgG. Many autoimmune diseases are wholly or partly mediated by IgG, as is the acute rejection of donated organs.

However, IdeS is an immunogenic protein. That is, when IdeS is used as a therapeutic agent the immune system of the subject receiving IdeS will often respond to it. The reaction of the immune system to IdeS will typically involve the production of antibodies specific for IdeS. These antibodies may be referred to herein as anti-drug antibodies (ADA) specific for IdeS or "IdeS-specific ADA". The immune response to IdeS in general, and the production of IdeS-specific ADA in particular, may cause two related types of problem. Firstly, the efficacy of IdeS may be reduced, e.g. due to ADA binding, potentially requiring higher or repeat doses to achieve the same effect. ADA which have this effect may be referred to as "neutralising ADA". Secondly, there may be undesirable or even harmful complications, such as a hyper-inflammatory response triggered by immune complexes of ADA and IdeS. The higher the quantity of ADA specific for IdeS in a given subject, the greater the likelihood of these problems. The presence and quantity of IdeS-specific ADA molecules in a patient may be determined by any suitable method, such as an agent specific CAP FEIA (ImmunoCAP) test or a titre assay conducted on a serum sample from the patient. Above a threshold determined by the clinician, the quantity of IdeS-specific ADA molecules in the patient may preclude administration of IdeS, or indicate that a higher dose of IdeS is required. Such a higher dose may in turn result in an increased quantity of IdeS-specific ADA molecules in the patient, thereby precluding further administration of IdeS.

IdeS is a virulence factor of *S. pyogenes*, which is responsible for common infections like tonsillitis and strep throat. Accordingly most human subjects have encountered IdeS in this context and are likely to have anti-IdeS antibodies in the bloodstream. IdeS-specific ADA are routinely detected in serum samples from random human subjects (likely due to prior streptococcal infections), as well as in IVIg (Intravenous Immunoglobulin) preparations, which are preparations of IgG extracted from the pooled serum of thousands of donors. Even if a subject does not possess IdeS-specific ADA prior to an initial administration of IdeS, it is likely that such molecules will be produced subsequently. Thus, for any given subject, the problems associated with the immunogenicity of IdeS are likely to present a barrier to the use of IdeS as a treatment. These problems may require increases to the dose of IdeS and/or preclude treatment with IdeS entirely, particularly if repeat administrations are required. Existing approaches to problems of this type involve, for example, PEGylation of a therapeutic agent to reduce immunogenicity or co-administration of the therapeutic agent with an immune-suppressive agent.

The present inventors have adopted an entirely different approach. The inventors have identified specific positions within the sequence of IdeS which, when modified as described herein, lead to novel polypeptides for which the problems associated with immunogenicity are reduced as compared to IdeS. Some modifications may increase the efficacy at cleaving IgG of the polypeptide of the invention relative to IdeS, thereby indirectly reducing immunogenicity by permitting the use of a lower dose or concentration to achieve the same effect. Alternatively, or in addition, other modifications may directly reduce immunogenicity by reducing the ability of IdeS-specific antibodies to recognise the polypeptide of the invention relative to IdeS.

The full sequence of IdeS is publically available as NCBI Reference Sequence no WP_010922160.1 and is provided herein as SEQ ID NO: 1. This sequence includes an N terminal methionine followed by a 28 amino acid secretion signal sequence. The N terminal methionine and the signal sequence (a total of 29 amino acids at the N terminus) are typically removed to form the mature IdeS protein, the sequence of which is publically available as Genbank accession no. ADF13949.1 and is provided herein as SEQ ID NO: 2.

Unless otherwise stated, all references to numbering of amino acid positions in the polypeptides disclosed herein is based on the numbering of the corresponding positions in SEQ ID NO: 1, starting from the N terminus. Thus, since SEQ ID NO: 2 lacks the N terminal methionine and 28 amino acid signal sequence of SEQ ID NO: 1, the aspartic acid (D) residue at the N terminus of SEQ ID NO: 2 is referred to as position 30 as this the corresponding position in SEQ ID NO: 1. Applying this numbering scheme, the most critical residue for IgG cysteine protease activity of IdeS is the cysteine (C) at position 94 ($65^{th}$ residue from the N terminus of SEQ ID NO: 2). Other residues likely to be important for IgG cysteine protease activity are the lysine (K) at position 84, the histidine (H) at position 262, and the aspartic acid (D) at each of positions 284 and 286. These are the $55^{th}$, $233^{rd}$, $255^{th}$ and $257^{th}$ residues from the N terminus of SEQ ID NO: 2, respectively.

In accordance with the present invention, there is thus provided a polypeptide having IgG cysteine protease activity and comprising a variant of the sequence of SEQ ID NO:2, which variant:
(a) is at least 50% identical to SEQ ID NO: 2;
(b) has a cysteine (C) at the position in said variant sequence which corresponds to position 94 of SEQ ID NO: 1; and optionally
(c) has, at the positions in said variant sequence which correspond to positions 84, 262, 284 and 286 of SEQ ID NO: 1, a lysine (K), a histidine (H), an aspartic acid (D) and an aspartic acid (D), respectively;
wherein said polypeptide is more effective at cleaving IgG than IdeS and/or is less immunogenic than IdeS. The polypeptide of the invention may be more effective at cleaving IgG1 than IgG2.
Preferably said variant of SEQ ID NO: 2:
(1) has a positively charged amino acid at the position in said variant which corresponds to position 130 of SEQ ID NO: 1, optionally wherein said positively charged amino acid is arginine (R) or lysine (K); and/or
(2) has a positively charged amino acid at the position in said variant which corresponds to position 131 of SEQ ID NO: 1, optionally wherein said positively charged amino acid is arginine (R) or lysine (K); and/or
(3) does not include the contiguous sequence NQTN; and/or
(4) does not include the contiguous sequence DSFSANQEIR YSEVTPYHVT.

The invention also provides a polynucleotide, an expression vector or a host cell encoding or expressing a polypeptide of the invention.

The invention also provides a method of treating or preventing a disease or condition mediated by IgG antibodies in a subject, the method comprising administering to the subject a therapeutically or prophylactically effective amount of a polypeptide of the invention. The method may typically comprise multiple administrations of said polypeptide to the subject.

The invention also provides a method of treating, ex vivo, blood taken from a patient, typically a patient suffering from a disease or condition mediated by IgG antibodies, which method comprises contacting the blood with a polypeptide of the invention.

The invention also provides a method for improving the benefit to a subject of a therapy or therapeutic agent, the method comprising (a) administering to the subject a polypeptide of the invention; and (b) subsequently administering said therapy or said therapeutic agent to the subject; wherein:
said therapy is an organ transplant or said therapeutic agent is an antibody, a gene therapy such as a viral vector, a replacement for a defective endogenous factor such as an enzyme, a growth or a clotting factor, or a cell therapy;
the amount of said polypeptide administered is sufficient to cleave substantially all IgG molecules present in the plasma of the subject; and
steps (a) and (b) are separated by a time interval which is sufficient to cleave substantially all IgG molecules present in the plasma of the subject.

The invention also provides a method of generating Fc, Fab or F(ab')$_2$ fragments of IgG comprising contacting IgG with a polypeptide of the invention, preferably ex vivo.

Also provided are kits for carrying out the methods according to the invention.

BRIEF DESCRIPTION OF THE SEQUENCES

Figure 1:
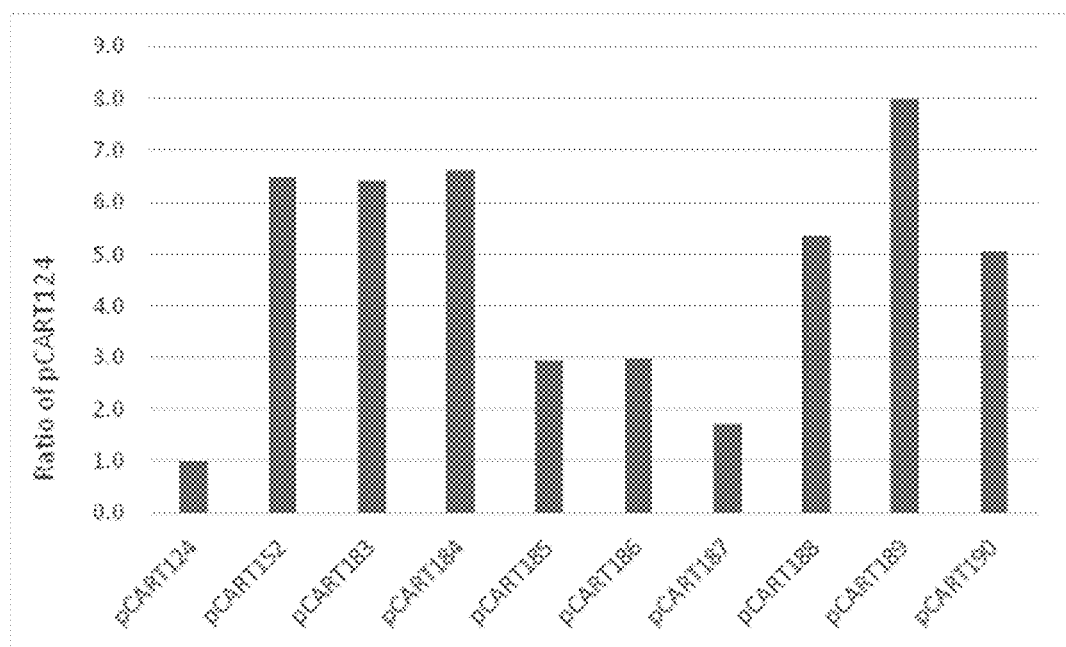
FIG. 1 shows the results of a representative assay to determine the potency (efficacy at cleavage of IgG) of polypeptides of the invention as compared to controls.

SEQ ID NO: 1 is the full sequence of IdeS including N terminal methionine and signal sequence. Also disclosed as NCBI Reference Sequence no WP_010922160.1

SEQ ID NO: 2 is the mature sequence of IdeS, lacking the N terminal methionine and signal sequence. Also disclosed as Genbank accession no. ADF13949.1

SEQ ID NOs: 3 to 16 are the sequences of exemplary polypeptides of the invention SEQ ID NO: 17 is the sequence of an IdeS polypeptide used herein as a control. Comprises the sequence of SEQ ID NO: 2 with an additional N terminal methionine and a histidine tag (internal reference pCART124).

SEQ ID NO: 18 is the contiguous sequence NQTN, which corresponds to positions 336-339 of SEQ ID NO: 1.

SEQ ID NO: 19 is the contiguous sequence DSFSANQEIR YSEVTPYHVT, which corresponds to positions 30-49 of SEQ ID NO: 1.

SEQ ID NOs: 20 to 34 are nucleotide sequences encoding polypeptides disclosed herein.

SEQ ID NO: 35 is the sequence SFSANQEIRY SEVTPYHVT, which corresponds to positions 31-49 of SEQ ID NO: 1.

SEQ ID NO: 36 is the sequence DYQRNATEAY AKEVPHQIT, which corresponds to positions 36-54 of the IdeZ polypeptide NCBI Reference Sequence no WP_014622780.1.

SEQ ID NO: 37 is the sequence DDYQRNATEA YAKEVPHQIT, which may be present at the N terminus of a polypeptide of the invention.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polypeptide" includes "polypeptides", and the like.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including both D or L optical isomers, and amino acid analogs and peptidomimetics.

The terms "patient" and "subject" are used interchangeably and typically refer to a human. References to IgG typically refer to human IgG unless otherwise stated.

All publications, patents and patent applications cited herein, whether supra or infra, are hereby incorporated by reference in their entirety.

Functional Features of the Polypeptide

The present invention relates to a novel polypeptide having IgG cysteine protease activity, wherein said polypeptide is more effective at cleaving IgG than IdeS and/or is less immunogenic than IdeS. In the context of a control or a comparison relative to a polypeptide of the invention, "IdeS" refers to a polypeptide consisting of the amino acid sequence of SEQ ID NO: 2. Alternatively or in addition, "IdeS" when used as a control or a comparison may refer to a polypeptide comprising the sequence the amino acid sequence of SEQ ID NO: 2 with an additional methionine (M) residue at the N terminus and/or a tag at the C terminus to assist with expression in and isolation from standard bacterial expression systems. Suitable tags include a histidine tag which may be joined directly to the C terminus of a polypeptide or joined indirectly by any suitable linker sequence, such as 3, 4 or 5 glycine residues. The histidine tag typically consists of six histidine residues, although it can be longer than this, typically up to 7, 8, 9, 10 or 20 amino acids or shorter, for example 5, 4, 3, 2 or 1 amino acids. The sequence of an exemplary IdeS polypeptide used herein is a control is provided as SEQ ID NO: 14. This polypeptide comprises the sequence of SEQ ID NO: 2 with an additional N terminal methionine and a histidine tag and may be referred to herein as pCART124.

IgG cysteine protease activity may be assessed by any suitable method, for example by incubating a polypeptide with a sample containing IgG and determining the presence of IgG cleavage products. Efficacy may be assessed in the presence or absence of an inhibitor, such as a neutralising antibody. However, efficacy herein will typically mean efficacy as assessed in the absence of such an inhibitor unless otherwise stated. Suitable methods are described in the Examples. The efficacy of a polypeptide at cleavage of IgG may be referred to herein as the "potency" of the polypeptide. The potency of a polypeptide of the invention is typically at least 1.5 fold, 2.0 fold, 2.5 fold, 3.0 fold, 4.0 fold, 4.5 fold, 5.0 fold, 6.0 fold, 7.0 fold or 7.5 fold greater than the potency of IdeS measured in the same assay. The potency of a polypeptide of the invention is preferably at least 4.5 fold, more preferably at least 6.0 fold and most preferably at least 7.5 fold greater than the potency of IdeS measured in the same assay. Increased potency relative to IdeS is a desirable improvement irrespective of the problems associated with immunogenicity of IdeS. However, such increased potency will typically also enable the use of a lower dose of a polypeptide of the invention for the same therapeutic effect as a higher dose of IdeS. The lower dose may also permit a greater number of repeat administrations of a polypeptide of the invention relative to IdeS. This is because the use of a lower dose reduces the problems associated with immunogenicity of a therapeutic agent, because the immune system is less likely to respond, or will respond less vigorously, to an agent which is present at a lower concentration. A polypeptide of the invention may therefore be as immunogenic as IdeS or even more immunogenic than IdeS when present at an equivalent dose, but problems associated with this immunogenicity are reduced or avoided because a lower dose is required to achieve the same therapeutic effect. In an alternative embodiment, a polypeptide of the invention may have equivalent potency to IdeS provided it is less immunogenic than IdeS when present at an equivalent dose.

Assays for assessing the efficacy of a polypeptide at the cleavage of IgG, that is assays for assessing the potency of a polypeptide, are well known in the art and any suitable assay may be used. Suitable assays include an ELISA-based assay, such as that which is described in the Examples. In such an assay, the wells of an assay plate will typically be coated with an antibody target, such as bovine serum albumin (BSA). Samples of the polypeptide to be tested are then added to the wells, followed by samples of target-specific antibody that is specific for BSA in this example. The polypeptide and antibody are allowed to interact under conditions suitable for IgG cysteine protease activity. After a suitable interval, the assay plate will be washed and a detector antibody which specifically binds to the target-specific antibody will be added under conditions suitable for binding to the target-specific antibody. The detector antibody will bind to any intact target-specific antibody that has bound to the target in each well. After washing, the amount of detector antibody present in a well will be proportional to the amount of target-specific antibody bound to that well. The detector antibody may be conjugated directly or indirectly to a label or another reporter system (such as an enzyme), such that the amount of detector antibody remaining in each well can be determined. The higher the potency of the tested polypeptide that was in a well, the less intact target-specific antibody will remain and thus there will be less detector antibody. Typically, at least one well on a given assay plate will include IdeS instead of a polypeptide to be tested, so that the potency of the tested polypeptides may be directly compared to the potency of IdeS. The polypeptide of the invention may be more effective at cleaving IgG1 than IgG2.

Other assays may determine the potency of a tested polypeptide by directly visualizing and/or quantifying the fragments of IgG which result from cleavage of IgG by a tested polypeptide. An assay of this type is also described in the Examples. Such an assay will typically incubate a sample of IgG with a test polypeptide (or with IdeS as a control) at differing concentrations in a titration series. The products which result from incubation at each concentration are then separated using gel electrophoresis, for example by SDS-PAGE. Whole IgG and the fragments which result from cleavage of IgG can then be identified by size and quantified by the intensity of staining with a suitable dye. The greater the quantity of cleavage fragments, the greater the potency of a tested polypeptide at a given concentration. A polypeptide of the invention will typically produce detectable quantities of cleavage fragments at a lower concentration (a lower point in the titration series) than IdeS. This type of assay may also enable the identification of test polypeptides that are more effective at cleaving the first or the second heavy chain of an IgG molecule, as the quantities of the different fragments resulting from each cleavage event may also be determined. This type of assay may also be adapted to determine the extent to which the presence of IdeS-specific ADA may reduce the potency of a polypeptide of the invention. In the adapted assay, when a sample of IgG is incubated with a test polypeptide (or with IdeS as a control), serum or an IVIg preparation containing IdeS-specific ADA is included with the reaction medium. Preferably, the potency of a polypeptide of the invention is not affected by the presence of ADA or is less reduced by the presence of ADA than the potency of IdeS in the same assay. In other words, preferably the neutralizing effect of IdeS-specific ADA on the polypeptide of the invention is the same or lower than the neutralizing effect of IdeS-specific ADA on IdeS, measured in the same assay.

As indicated above, a polypeptide of the invention may be as immunogenic as IdeS or even more immunogenic than IdeS when present at an equivalent dose, because the problems associated with this immunogenicity are reduced or avoided since a lower dose of the polypeptide of the invention is required to achieve the same therapeutic effect. However, typically a polypeptide of the invention is no more immunogenic than IdeS and preferably it is less immunogenic than IdeS. That is, a polypeptide of the invention may result in the same or preferably a lower immune response than IdeS when present at an equivalent dose or concentration and measured in the same assay. The immunogenicity of a polypeptide of the invention is typically no more than 90%, no more than 85%, no more than 80%, no more than 70%, no more than 60%, or no more than 50% of the immunogenicity of IdeS measured in the same assay. Preferably the immunogenicity of a polypeptide of the invention is no more than 85% of the immunogenicity of IdeS measured in the same assay. More preferably the immunogenicity of a polypeptide of the invention is no more than 70% of the immunogenicity of IdeS measured in the same assay.

Assays for assessing the immunogenicity of a polypeptide are known in the art and any suitable assay may be used. Preferred assays for assessing the immunogenicity of a polypeptide relative to the immunogenicity of IdeS involves assessing the extent to which ADA specific for IdeS also bind to a polypeptide of the invention. Assays of this type are described in the Examples.

One such an assay involves testing for competition between IdeS and a test polypeptide for binding to IdeS-specific ADA. Typically, the wells of an assay plate are coated with IdeS, followed by administration of a pre-incubated mixture of a solution containing IdeS-specific ADA, e.g. an IVIg preparation, and a test polypeptide (or IdeS as a control). The pre-incubation takes place in the presence of an inhibitor of IgG cysteine protease activity, e.g. iodoacetic acid (IHAc), and at high salt concentration so that only high affinity binding between protein and ADA is permitted. The pre-incubated mixture is allowed to interact with the IdeS coated wells. Any IdeS-specific ADA not bound to test polypeptide will bind to the IdeS on the wells. After a suitable interval, the assay plate will be washed and a detector antibody which specifically binds to IgG will be added under conditions suitable for binding. The detector antibody will bind to any ADA that has bound to the IdeS in each well. After washing, the amount of detector antibody present in a well will be inversely proportional to the amount of ADA that had bound to the test polypeptide. The detector antibody may be conjugated directly or indirectly to a label or another reporter system (such as an enzyme), such that the amount of detector antibody remaining in each well can be determined. Typically, at least one well on a given assay plate will be tested with a pre-incubated mixture of IVIg and IdeS instead of a polypeptide to be tested, so that the binding of ADA to the tested polypeptides may be directly compared to the binding to IdeS.

Another suitable assay involves testing the extent to which a titration series of different concentrations of IdeS-specific ADA, e.g. an IVIg preparation, binds to a test polypeptide as compared to IdeS. Preferably, a polypeptide of the invention will require a higher concentration of ADA for binding to be detectable, relative to the concentration of ADA for which binding to IdeS is detectable. Such an assay is described in the Examples. Such an assay typically involves coating the wells of an assay plate with test polypeptide or IdeS, followed by incubating with each well with a different concentration of IdeS-specific ADA from a titration series. The incubations are conducted in the presence of an inhibitor of IgG cysteine protease activity, e.g. iodoacetic acid (IHAc), and at high salt concentration so that only high affinity binding between protein and ADA is permitted. After a suitable interval, the assay plate will be washed and a detector antibody which specifically binds to IgG F(ab')$_2$ will be added under conditions suitable for binding. The detector antibody will bind to any ADA that has bound to the test polypeptide or the IdeS in each well. After washing, the amount of detector antibody present in a well will be directly proportional to the amount of ADA that had bound to the test polypeptide or IdeS. The detector antibody may be conjugated directly or indirectly to a label or another reporter system (such as an enzyme), such that the amount of detector antibody remaining in each well can be determined. At least one well on a given assay plate will be incubated with buffer lacking ADA as a blank to establish a threshold level for detection of binding in the test wells.

Structural Features of the Polypeptide

This section sets out the structural features of a polypeptide of the invention, which apply in addition to the functional features outlined in the preceding section.

The polypeptide of the invention is typically at least 100, 150, 200, 250, 260, 270, 280, 290 or 300 amino acids in length. The polypeptide of the invention is typically no larger than 400, 350, 340, 330, 320 or 310 amino acids in length. It will be appreciated that any of the above listed lower limits may be combined with any of the above listed upper limits to provide a range for the length the polypeptide of the invention. For example, the polypeptide may be 100 to 400 amino acids in length, or 250 to 350 amino acids in length. The polypeptide is preferably 290 to 320 amino acids in length, most preferably 300 to 310 amino acids in length.

The primary structure (amino acid sequence) of a polypeptide of the invention is based on the primary structure of IdeS, specifically the amino acid sequence of SEQ ID NO: 2. The sequence of a polypeptide of the invention comprises a variant of the amino acid sequence of SEQ ID NO: 2 which is at least 50% identical to the amino acid sequence of SEQ ID NO: 2. The variant sequence may be at least 60%, at least 70%, at least 80%, at least 85%, preferably at least 90%, at least 95%, at least 98% or at least 99% identical to the sequence of SEQ ID NO:2. The variant may be identical to the sequence of SEQ ID NO: 2 apart from the inclusion of one or more of the specific modifications identified herein. Identity relative to the sequence of SEQ ID NO: 2 can be measured over a region of at least 50, at least 100, at least 200, at least 300 or more contiguous amino acids of the sequence shown in SEQ ID NO: 2, or more preferably over the full length of SEQ ID NO: 2.

Amino acid identity may be calculated using any suitable algorithm. For example the PILEUP and BLAST algorithms can be used to calculate identity or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10. Software for performing BLAST analyses is publicly available through the National Center for Biotechnology Information (This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001. Alternatively, the UWGCG Package provides the BESTFIT program which can be used to calculate identity (for example used on its default settings) (Devereux et al (1984) *Nucleic Acids Research* 12, 387-395).

The sequence of a polypeptide of the invention comprises a variant of the amino acid sequence of SEQ ID NO: 2 in which modifications, such as amino acid additions, deletions or substitutions are made relative to the sequence of SEQ ID NO: 2. Unless otherwise specified, the modifications are preferably conservative amino acid substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table A1 below. Where amino acids have similar polarity, this can be determined by reference to the hydropathy scale for amino acid side chains in Table A2.

TABLE A1

Chemical properties of amino acids

| | |
|---|---|
| Ala (A) | aliphatic, hydrophobic, neutral |
| Cys (C) | polar, hydrophobic, neutral |
| Asp (D) | polar, hydrophilic, charged (−) |
| Glu (E) | polar, hydrophilic, charged (−) |
| Phe (F) | aromatic, hydrophobic, neutral |
| Gly (G) | aliphatic, neutral |
| His (H) | aromatic, polar, hydrophilic, charged (+) |
| Ile (I) | aliphatic, hydrophobic, neutral |
| Lys (K) | polar, hydrophilic, charged(+) |
| Leu (L) | aliphatic, hydrophobic, neutral |
| Met (M) | hydrophobic, neutral |
| Asn (N) | polar, hydrophilic, neutral |
| Pro (P) | hydrophobic, neutral |
| Gln (Q) | polar, hydrophilic, neutral |
| Arg (R) | polar, hydrophilic, charged (+) |
| Ser (S) | polar, hydrophilic, neutral |
| Thr (T) | polar, hydrophilic, neutral |
| Val (V) | aliphatic, hydrophobic, neutral |
| Trp (W) | aromatic, hydrophobic, neutral |
| Tyr (Y) | aromatic, polar, hydrophobic |

TABLE A2

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

The amino acid sequence of a polypeptide of the invention comprises a variant of the amino acid sequence of SEQ ID NO: 2. However, certain residues in the amino acid sequence of SEQ ID NO: 2 are preferably retained within the said variant sequence. For example, the said variant sequence typically retains certain residues which are known to be required for IgG cysteine protease activity. Thus, the cysteine at position 94 of SEQ ID NO: 1 must be retained ($65^{th}$ residue of SEQ ID NO: 2) in the amino acid sequence of a polypeptide of the invention. Optionally, the lysine at position 84, the histidine at position 262 and the aspartic acid at each of positions 284 and 286 of SEQ ID NO: 1 are also retained. These are the $55^{th}$ $233^{rd}$, $255^{th}$ and $257^{th}$ residues of SEQ ID NO: 2, respectively. Thus, a polypeptide of the invention typically comprises a variant of the amino acid sequence of SEQ ID NO: 2 which has a cysteine (C) at the position in said variant sequence which corresponds to position 94 of SEQ ID NO: 1; and optionally has, at the positions in said variant sequence which correspond to positions 84, 262, 284 and 286 of SEQ ID NO: 1, a lysine (K), a histidine (H), an aspartic acid (D) and an aspartic acid (D), respectively;

Starting with the above structural limitations, the inventors identified specific positions for modification to adjust the functional properties of IdeS by assessing a three dimensional model of IdeS. The inventors have identified the following:

(1) Replacing the asparagine (N) at position 130 of SEQ ID NO: 1 with a positively charged amino acid enhances the potency of a polypeptide which incorporates this change. Thus, a polypeptide of the invention may comprise a variant of the amino acid sequence of SEQ ID NO: 2 which has a positively charged amino acid at the position in said variant which corresponds to position 130 of SEQ ID NO: 1. Common positively charged amino acids are identified in Table A1 above. The positively charged amino acid is preferably arginine (R) or lysine (K). Accordingly this particular modification may be identified herein by the term "N130R/K".

(2) Replacing the glycine (G) at position 131 of SEQ ID NO: 1 with a positively charged amino acid enhances the potency of a polypeptide which incorporates this change. Thus, a polypeptide of the invention may comprise a variant of the amino acid sequence of SEQ ID NO: 2 which has a positively charged amino acid at the position in said variant which corresponds to position 131 of SEQ ID NO: 1. Common positively charged amino acids are identified in Table A1 above. The positively charged amino acid is preferably arginine (R) or lysine (K). Accordingly this particular modification may be identified herein by the term "G131R/K".

(3) Deleting the last four residues at the C terminus of SEQ ID NO: 2 enhances the potency of a polypeptide which incorporates this change. The last four residues at the C terminus of SEQ ID NO: 2 consist of the contiguous sequence NQTN. Thus, a polypeptide of the invention may comprise a variant of the amino acid sequence of SEQ ID NO: 2 which does not include the contiguous sequence NQTN. That is, the last four residues at the C terminus of SEQ ID NO: 2 may be absent from said variant of SEQ ID NO: 2. The last four residues of SEQ ID NO: 2 correspond to positions 336-339 of SEQ ID NO: 1. Accordingly this particular modification may be identified herein by the term "N336_N339del".

(4) Deleting or altering the sequence of the first twenty residues at the N terminus of SEQ ID NO: 2 may enhance the potency of a polypeptide which incorporates this change and/or may reduce immunogenicity without adversely affecting potency.

The first twenty residues at the N terminus of SEQ ID NO: 2 consist of the contiguous sequence DSFSANQEIRYSEVTPYHVT (SEQ ID NO: 19). Thus, a polypeptide of the invention may comprise a variant of the amino acid sequence of SEQ ID NO: 2 which does not include the contiguous sequence DSFSANQEIRYSEVTPYHVT.

As an example, the said contiguous sequence of SEQ ID NO: 19 may be deleted in its entirety. That is, the first twenty residues at the N terminus of SEQ ID NO: 2 may be absent from said variant of SEQ ID NO: 2. The first twenty residues of SEQ ID NO: 2 correspond to positions 30-49 of SEQ ID NO: 1. Accordingly the deletion of this contiguous sequence may be identified herein by the term "D30_T49del".

Alternatively, a polypeptide of the invention may comprise a variant of the amino acid sequence of SEQ ID NO: 2 in which the sequence of the first twenty residues at the N terminus of SEQ ID NO: 2 is altered by replacing one or more amino acids in said first twenty residues. The altered sequence preferably has reduced immunogenicity compared to the first twenty amino acids of SEQ ID NO: 2. As an example, the amino acids at positions 2 to 20 of SEQ ID NO: 2 (which corresponding to positions 31-49 of SEQ ID NO: 1) may optionally be replaced with the contiguous sequence DYQRNATEAY AKEVPHQIT (SEQ ID NO: 36). In other words, the first twenty amino acids of a polypeptide of the invention may consist of the sequence DDYQRNATEA YAKEVPHQIT (SEQ ID NO: 37) instead of the sequence of SEQ ID NO: 19. The inserted sequence SEQ ID NO: 36 is taken from the N terminal region of IdeZ and corresponds to positions 36-54 of the IdeZ NCBI Reference Sequence no WP_014622780.1. Human subjects typically do not express antibodies to IdeZ, and so a polypeptide including this sequence is less prone to ADA. The replacement of SEQ ID NO: 35 with SEQ ID NO: 37 may be identified herein by the term "S31_T49replZ".

In summary therefore, a polypeptide of the invention comprises a variant of the sequence of SEQ ID NO: 2, which variant:
  (a) is at least 50% identical to SEQ ID NO: 2;
  (b) has a cysteine (C) at the position in said variant sequence which corresponds to position 94 of SEQ ID NO: 1; and optionally
  (c) has, at the positions in said variant sequence which correspond to positions 84, 262, 284 and 286 of SEQ ID NO: 1, a lysine (K), a histidine (H), an aspartic acid (D) and an aspartic acid (D), respectively;

Preferably, said variant of SEQ ID NO: 2:
  (1) has a positively charged amino acid at the position in said variant which corresponds to position 130 of SEQ ID NO: 1, optionally wherein said positively charged amino acid is arginine (R) or lysine (K); and/or
  (2) has a positively charged amino acid at the position in said variant which corresponds to position 131 of SEQ ID NO: 1, optionally wherein said positively charged amino acid is arginine (R) or lysine (K); and/or
  (3) does not include the contiguous sequence NQTN; and/or
  (4) does not include the contiguous sequence DSFSANQEIR YSEVTPYHVT.

Said variant of SEQ ID NO: 2 may include one, two, three or all four of modifications (1) to (4) set out above. Said variant may include any combination of two or three of modifications (1) to (4) set out above. A preferred variant includes modification (3) and at least one of modifications (1) and (2). Another preferred variant includes modifications (3) and (4) and at least one of modifications (1) and (2).

The inventors have also determined that certain other modifications to the sequence of SEQ ID NO: 2, which may be applied alternatively or in addition to any combination of the modifications (1) to (4) described above, may increase the potency of a polypeptide of the invention and/or may reduce the recognition of a polypeptide of the invention by IdeS-specific ADA. Thus, a polypeptide of the invention may comprise a variant of the sequence of SEQ ID NO: 2 in which a substitution is made at one or more of the positions corresponding to positions 115, 119, 139, 142, 198, 216, 226, 241, 245, 302, 316, and 333 of SEQ ID NO: 1. The said variant may comprise a substitution in all of these positions, but typically comprises a substitution in two, three, four, five, six, or seven of these positions. The substitutions in these positions typically replace the existing amino acid with another amino acid that has different properties. For example, an uncharged amino acid may be replaced with a charged amino acid, and vice versa. Preferred substitutions at these positions are set out in Table B below using the one letter code:

TABLE B

| Existing amino acid in SEQ ID NO: 2 | Position in SEQ ID NO: 1 | Preferred replacement |
|---|---|---|
| K | 115 | E |
| E | 119 | R |
| E | 139 | K |
| D | 142 | R |
| E | 198 | K |
| D | 216 | N |
| D | 226 | N |
| K | 241 | E |
| E | 245 | K |
| S | 302 | K |
| D | 316 | K |
| D | 333 | K |

Each of the substitutions in table B may be referred to herein using a term obtained by combining the entries in the first, second and third columns for each row from left to right. For example, the substitution in the first row may be referred to herein as "K115E", the substitution in the second row may be referred to as "E119R", and so on. The specific modification "D226N" is intended to disrupt a known cell adhesion motif in the sequence of IdeS, that is the contiguous RGD sequence at positions 224-226 of SEQ ID NO: 1.

Table C below summarizes the modifications made to produce the amino acid sequences of certain exemplary polypeptides of the invention.

TABLE C

| Internal reference | Modifications relative to IdeS (positions correspond to SEQ ID NO: 1) | SEQ ID NO of full sequence |
|---|---|---|
| pCART152 | N130R | 3 |
| pCART183 | N130K, E198R, D216N | 4 |
| pCART184 | N130R, E198K, D216N, S302K | 5 |
| pCART185 | E119R, D216N, T244D | 6 |
| pCART186 | E119K, D142R, D216N, T244E, S302K | 7 |
| pCART187 | K115E, D216N, K241E, E245K, D316K, D333K | 8 |
| pCART188 | E119K, N130R, D142R, D216N, K241S, T244E, E245N, S302K | 9 |
| pCART189 | E119K, N130R, D142R, E198K, D216N, T244E | 10 |
| pCART190 | K115E, N130R, E198K, D216N, K241E, E245K, D333K | 11 |
| pCART209 | N336_N339del (NQTN deletion) | 12 |
| pCART125 | D30_T49del (DSFSANQEIR YSEVTPYHVT deletion) | 13 |
| pCART213 | D30_T49del (DSFSANQEIR YSEVTPYHVT deletion), N130K, D216N | 14 |

TABLE C-continued

| Internal reference | Modifications relative to IdeS (positions correspond to SEQ ID NO: 1) | SEQ ID NO of full sequence |
|---|---|---|
| PCART214 | D30_T49del (DSFSANQEIR YSEVTPYHVT deletion), K115E, N130K, E139K, D216N, K241E, E245K, D333K | 15 |
| pCART228 | S31_T49replZ (replace SEQ ID NO: 35 with SEQ ID NO: 36), K115E, N130K, E139K, D216N, K241E, E245K, D333K | 16 |

The amino acid sequence of SEQ ID NOs: 1 and 2 is reproduced in full below, followed by the amino acid sequence of each of the exemplary polypeptides of the invention described in Table C.

SEQ ID NO: 1
MRKRCYSTSAAVLAAVTLFVLSVDRGVIADSFSANQEIRYSEVTPYHVT
SVWTKGVTPPANFTQGEDVFHAPYVANQGWYDITKTFNGKDDLLCGAAT
AGNMLHWWFDQNKDQIKRYLEEHPEKQKINFNGEQMFDVKEAIDTKNHQ
LDSKLFEYFKEKAFPYLSTKHLGVFPDHVIDMFINGYRLSLTNHGPTPV
KEGSKDPRGGIFDAVFTRGDQSKLLTSRHDFKEKNLKEISDLIKKELTE
GKALGLSHTYANVRINHVINLWGADFDSNGNLKAIYVTDSDSNASIGMK
KYFVGVNSAGKVAISAKEIKEDNIGAQVLGLFTLSTGQDSWNQTN

SEQ ID NO: 2
DSFSANQEIRYSEVTPYHVTSVWTKGVTPPANFTQGEDVFHAPYVANQG
WYDITKTFNGKDDLLCGAATAGNMLHWWFDQNKDQIKRYLEEHPEKQKI
NFNGEQMFDVKEAIDTKNHQLDSKLFEYFKEKAFPYLSTKHLGVFPDHV
IDMFINGYRLSLTNHGPTPVKEGSKDPRGGIFDAVFTRGDQSKLLTSRH
DFKEKNLKEISDLIKKELTEGKALGLSHTYANVRINHVINLWGADFDSN
GNLKAIYVTDSDSNASIGMKKYFVGVNSAGKVAISAKEIKEDNIGAQVL
GLFTLSTGQDSWNQTN (pCART152)
SEQ ID NO: 3
DSFSANQEIRYSEVTPYHVTSVWTKGVTPPANFTQGEDVFHAPYVANQG
WYDITKTFNGKDDLLCGAATAGNMLHWWFDQNKDQIKRYLEEHPEKQKI
NFRGEQMFDVKEAIDTKNHQLDSKLFEYFKEKAFPYLSTKHLGVFPDHV
IDMFINGYRLSLTNHGPTPVKEGSKDPRGGIFDAVFTRGDQSKLLTSRH
DFKEKNLKEISDLIKKELTEGKALGLSHTYANVRINHVINLWGADFDSN
GNLKAIYVTDSDSNASIGMKKYFVGVNSAGKVAISAKEIKEDNIGAQVI
GLFTLSTGQDSWNQTN (pCART183)
SEQ ID NO: 4
DSFSANQEIRYSEVTPYHVTSVWTKGVTPPANFTQGEDVFHAPYVANQG
WYDITKTFNGKDDLLCGAATAGNMLHWWFDQNKDQIKRYLEEHPEKQKI
NFKGEQMFDVKEAIDTKNHQLDSKLF
EYFKEKAFPYLSTKHLGVFPDHVIDMFINGYRLSLTNHGPTPVKRGSKD
PRGGIFDAVFTRGNQSKLLTSRHDFKEKNLKEISDLIKKELTEGKALGL
SHTYANVRINHVINLWGADFDSNGNLKAIYVTDSDSNASIGMKKYFVGV
NSAGKVAISAKEIKEDNIGAQVLGLFTLSTGQDSWNQTN (pCART184)
SEQ ID NO: 5
DSFSANQEIRYSEVTPYHVTSVWTKGVTPPANFTQGEDVFHAPYVANQG
WYDITKTFNGKDDLLCGAATAGNMLHWWFDQNKDQIKRYLEEHPEKQKI
NFRGEQMFDVKEAIDTKNHQLDSKLFEYFKEKAFPYLSTKHLGVFPDHV
IDMFINGYRLSLTNHGPTPVKKGSKDPRGGIFDAVFTRGNQSKLLTSRH
DFKEKNLKEISDLIKKELTEGKALGLSHTYANVRINHVINLWGADFDSN
GNLKAIYVTDSDSNASIGMKKYFVGVNKAGKVAISAKEIKEDNIGAQVL
GLFTLSTGQDSWNQTN (pCART185)
SEQ ID NO: 6
DSFSANQEIRYSEVTPYHVTSVWTKGVTPPANFTQGEDVFHAPYVANQG
WYDITKTFNGKDDLLCGAATAGNMLHWWFDQNKDQIKRYLREHPEKQKI
NFNGEQMFDVKEAIDTKNHQLDSKLFEYFKEKAFPYLSTKHLGVFPDHV
IDMFINGYRLSLTNHGPTPVKEGSKDPRGGIFDAVFTRGNQSKLLTSRH
DFKEKNLKEISDLIKKELDEGKALGLSHTYANVRINHVINLWGADFDSN
GNLKAIYVTDSDSNASIGMKKYFVGVNSAGKVAISAKEIKEDNIGAQVL
GLFTLSTGQDSWNQTN (pCART186)
SEQ ID NO: 7
DSFSANQEIRYSEVTPYHVTSVWTKGVTPPANFTQGEDVFHAPYVANQG
WYDITKTFNGKDDLLCGAATAGNMLHWWFDQNKDQIKRYLKEHPEKQKI
NFNGEQMFDVKEAIRTKNHQLDSKLFEYFKEKAFPYLSTKHLGVFPDHV
IDMFINGYRLSLTNHGPTPVKEGSKDPRGGIFDAVFTRGNQSKLLTSRH
DFKEKNLKEISDLIKKELEEGKALGLSHTYANVRINHVINLWGADFDSN
GNLKAIYVTDSDSNASIGMKKYFVGVNKAGKVAISAKEIKEDNIGAQVL
GLFTLSTGQDSWNQTN (pCART187)
SEQ ID NO: 8
DSFSANQEIRYSEVTPYHVTSVWTKGVTPPANFTQGEDVFHAPYVANQG
WYDITKTFNGKDDLLCGAATAGNMLHWWFDQNKDQIERYLEEHPEKQKI
NFNGEQMFDVKEAIDTKNHQLDSKLFEYFKEKAFPYLSTKHLGVFPDHV
IDMFINGYRLSLTNHGPTPVKEGSKDPRGGIFDAVFTRGNQSKLLTSRH
DFKEKNLKEISDLIKEELTKGKALGLSHTYANVRINHVINLWGADFDSN
GNLKAIYVTDSDSNASIGMKKYFVGVNSAGKVAISAKEIKEKNIGAQVL
GLFTLSTGQKSWNQTN

-continued (pCART188)
SEQ ID NO: 9
DSFSANQEIRYSEVTPYHVTSVWTKGVTPPANFTQGEDVFHAPYVANQG
WYDITKTFNGKDDLLCGAATAGNMLHWWFDQNKDQIKRYLKEHPEKQI
NFRGEQMFDVKEAIRTKNHQLDSKLFEYFKEKAFPYLSTKHLGVFPDHV
IDMFINGYRLSLTNHGPTPVKEGSKDPRGGIFDAVFTRGNQSKLLTSRH
DFKEKNLKEISDLIKSELENGKALGLSHTYANVRINHVINLWGADFDSN
GNLKAIYVTDSDSNASIGMKKYFVGVNKAGKVAISAKEIKEDNIGAQVL
GLFTLSTGQDSWNQTN (pCART189)
SEQ ID NO: 10
DSFSANQEIRYSEVTPYHVTSVWTKGVTPPANFTQGEDVFHAPYVANQG
WYDITKTFNGKDDLLCGAATAGNMLHWWFDQNKDQIKRYLKEHPEKQI
NFRGEQMFDVKEAIRTKNHQLDSKLFEYFKEKAFPYLSTKHLGVFPDHV
IDMFINGYRLSLTNHGPTPVKKGSKDPRGGIFDAVFTRGNQSKLLTSRH
DFKEKNLKEISDLIKKELEEGKALGLSHTYANVRINHVINLWGADFDSN
GNLKAIYVTDSDSNASIGMKKYFVGVNSAGKVAISAKEIKEDNIGAQVL
GLFTLSTGQDSWNQTN (pCART190)
SEQ ID NO: 11
DSFSANQEIRYSEVTPYHVTSVWTKGVTPPANFTQGEDVFHAPYVANQG
WYDITKTFNGKDDLLCGAATAGNMLHWWFDQNKDQIERYLEEHPEKQI
NFRGEQMFDVKEAIDTKNHQLDSKLFEYFKEKAFPYLSTKHLGVFPDHV
IDMFINGYRLSLTNHGPTPVKKGSKDPRGGIFDAVFTRGNQSKLLTSRH
DFKEKNLKEISDLIKEELTKGKALGLSHTYANVRINHVINLWGADFDSN
GNLKAIYVTDSDSNASIGMKKYFVGVNSAGKVAISAKEIKEDNIGAQVL
GLFTLSTGQKSWNQTN (pCART209)
SEQ ID NO: 12
DSFSANQEIRYSEVTPYHVTSVWTKGVTPPANFTQGEDVFHAPYVANQG
WYDITKTFNGKDDLLCGAATAGNMLHWWFDONKDQIKRYLEEHPEKQI
NFNGEQMFDVKEAIDTKNHQLDSKLFEYFKEKAFPYLSTKHLGVFPDHV
IDMFINGYRLSLTNHGPTPVKEGSKDPRGGIFDAVFTRGDQSKLLTSRH
DFKEKNLKEISDLIKKELTEGKALGLSHTYANVRINHVINLWGADFDSN
GNLKAIYVTDSDSNASIGMKKYFVGVNSAGKVAISAKEIKEDNIGAQVL
GLFTLSTGQDSW (pCART125)
SEQ ID NO: 13
SVWTKGVTPPANFTQGEDVFHAPYVANQGWYDITKTFNGKDDLLCGAAT
AGNMLHWWFDQNKDQIKRYLEEHPEKQKINFNGEQMFDVKEAIDTKNHQ
LDSKLFEYFKEKAFPYLSTKHLGVFPDHVIDMFINGYRLSLTNHGPTPV
KEGSKDPRGGIFDAVFTRGDQSKLLTSRHDFKEKNLKEISDLIKKELTE
GKALGLSHTYANVRINHVINLWGADFDSNGNLKAIYVTDSDSNASIGMK
KYFVGVNSAGKVAISAKEIKEDNIGAQVLGLFTLSTGQDSWNQTN (pCART213)
SEQ ID NO: 14
SVWTKGVTPPANFTQGEDVFHAPYVANQGWYDITKTFNGKDDLLCGAAT
AGNMLHWWFDQNKDQIKRYLEEHPEKQKINFKGEQMFDVKEAIDTKNHQ
LDSKLFEYFKEKAFPYLSTKHLGVFPDHVIDMFINGYRLSLTNHGPTPV
KEGSKDPRGGIFDAVFTRGNQSKLLTSRHDFKEKNLKEISDLIKKELTE
GKALGLSHTYANVRINHVINLWGADFDSNGNLKAIYVTDSDSNASIGMK
KYFVGVNSAGKVAISAKEIKEDNIGAQVLGLFTLSTGQDSWNQTN (pCART214)
SEQ ID NO: 15
SVWTKGVTPPANFTQGEDVFHAPYVANQGWYDITKTFNGKDDLLCGAAT
AGNMLHWWFDQNKDQIERYLEEHPEKSKDPRGGIFDAVFTRGNQSKLLT
SRHDFKEKNLKEISDLIKEELTKGKALGLSHTYANVRINHVINLWGADF
DSNGNLKAIYVTDSDSNASIGMKKYFVGVNSAGKVAISAKEIKEDNIGA
QVLGLFTLSTGQKSWNQTN (pCART228)
SEQ ID NO: 16
DDYQRNATEAYAKEVPHQITSVWTKGVTPPANFTQGEDVFHAPYVANQG
WYDITKTFNGKDDLLCGAATAGNMLHFINGYRLSLTNHGPTPVKEGSKD
PRGGIFDAVFTRGNQSKLLTSRHDFKEKNLKEISDLIKEELTKGKALGL
SHTYANVRINHVINLWGADFDSNGNLKAIYVTDSDSNASIGMKKYFVGV
NSAGKVAISAKEIKEDNIGAQVLGLFTLSTGQKSWNQTNGGGHHHHHH The polypeptide of the invention may comprise, consist essentially, or consist of the sequence of any one of SEQ ID NOs: 3 to 16. Each of SEQ ID NOs: 3 to 16 may optionally include an additional methionine at the N terminus and/or a histidine tag at the C terminus. The histidine tag is preferably consists of six histidine residues. The histidine tag is preferably linked to the C terminus by a linker of 3× glycine or 5× glycine residues. For SEQ ID NO: 13 the histidine tag is preferably linked to the C terminus by a linker of 5× glycine residues.

Production of Polypeptides

A polypeptide as disclosed herein may be produced by any suitable means. For example, the polypeptide may be synthesised directly using standard techniques known in the art, such as Fmoc solid phase chemistry, Boc solid phase chemistry or by solution phase peptide synthesis. Alternatively, a polypeptide may be produced by transforming a cell, typically a bacterial cell, with a nucleic acid molecule or vector which encodes said polypeptide. Production of polypeptides by expression in bacterial host cells is described below and is exemplified in the Examples. The invention provides nucleic acid molecules and vectors which encode a polypeptide of the invention. The invention also provides a host cell comprising such a nucleic acid or vector. Exemplary polynucleotide molecules encoding polypeptides disclosed herein are provided as SEQ ID NOs: 20 to 34. Each of these sequences includes at the 3' end a codon for the N terminal methionine (ATG) and, prior to the stop codon (TAA) at the 5' end, codons for a 3× gly linker and a 6× his histidine tag, which may optionally be excluded.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or substantially isolated form. By substantially isolated, it is meant that there may be substantial, but not total, isolation of the polypeptide from any surrounding medium. The polynucleotides may be mixed with carriers or diluents which will not interfere with their intended use and still be regarded as substantially isolated. A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences, for example in an expression vector. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides can be synthesised according to methods well known in the art, as described by way of example in Sambrook et al (1989, Molecular Cloning—a laboratory manual; Cold Spring Harbor Press). The nucleic acid molecules of the present invention may be provided in the form of an expression cassette which includes control sequences operably linked to the inserted sequence, thus allowing for expression of the polypeptide of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes cells that have been modified to express a polypeptide of the invention. Such cells typically include prokaryotic cells such as bacterial cells, for example E. coli. Such cells may be cultured using routine methods to produce a polypeptide of the invention.

A polypeptide may be derivatised or modified to assist with their production, isolation or purification. For example, where a polypeptide of the invention is produced by recombinant expression in a bacterial host cell, the sequence of the polypeptide may include an additional methionine (M) residue at the N terminus to improve expression. As another example, the polypeptide of the invention may be derivatised or modified by addition of a ligand which is capable of binding directly and specifically to a separation means. Alternatively, the polypeptide may be derivatised or modified by addition of one member of a binding pair and the separation means comprises a reagent that is derivatised or modified by addition of the other member of a binding pair. Any suitable binding pair can be used. In a preferred embodiment where the polypeptide for use in the invention is derivatised or modified by addition of one member of a binding pair, the polypeptide is preferably histidine-tagged or biotin-tagged. Typically the amino acid coding sequence of the histidine or biotin tag is included at the gene level and the polypeptide is expressed recombinantly in E. coli. The histidine or biotin tag is typically present at either end of the polypeptide, preferably at the C-terminus. It may be joined directly to the polypeptide or joined indirectly by any suitable linker sequence, such as 3, 4 or 5 glycine residues. The histidine tag typically consists of six histidine residues, although it can be longer than this, typically up to 7, 8, 9, 10 or 20 amino acids or shorter, for example 5, 4, 3, 2 or 1 amino acids.

The amino acid sequence of a polypeptide may be modified to include non-naturally occurring amino acids, for example to increase stability. When the polypeptides are produced by synthetic means, such amino acids may be introduced during production. The polypeptides may also be modified following either synthetic or recombinant production. Polypeptides may also be produced using D-amino acids. In such cases the amino acids will be linked in reverse sequence in the C to N orientation. This is conventional in the art for producing such polypeptides.

A number of side chain modifications are known in the art and may be made to the side chains of the polypeptides, subject to the polypeptides retaining any further required activity or characteristic as may be specified herein. It will also be understood that polypeptides may be chemically modified, e.g. post-translationally modified. For example, they may be glycosylated, phosphorylated or comprise modified amino acid residues.

The polypeptide may be PEGylated. The polypeptide of the invention may be in a substantially isolated form. It may be mixed with carriers or diluents (as discussed below) which will not interfere with the intended use and still be regarded as substantially isolated. It may also be in a substantially purified form, in which case it will generally comprise at least 90%, e.g. at least 95%, 98% or 99%, of the protein in the preparation.

Compositions and Formulations Comprising Polypeptides

In another aspect, the present invention provides compositions comprising a polypeptide of the invention. For example, the invention provides a composition comprising one or more polypeptides of the invention, and at least one pharmaceutically acceptable carrier or diluent. The carrier (s) must be 'acceptable' in the sense of being compatible with the other ingredients of the composition and not deleterious to a subject to which the composition is administered. Typically, carriers and the final composition, are sterile and pyrogen free.

Formulation of a suitable composition can be carried out using standard pharmaceutical formulation chemistries and methodologies all of which are readily available to the reasonably skilled artisan. For example, the agent can be combined with one or more pharmaceutically acceptable excipients or vehicles. Auxiliary substances, such as wetting or emulsifying agents, pH buffering substances, reducing agents and the like, may be present in the excipient or vehicle. Suitable reducing agents include cysteine, thioglycerol, thioreducin, glutathione and the like. Excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol, thioglycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e. g., sterile pyrogen-free water) prior to parenteral administration of the reconstituted composition. The compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other parentally-administrable compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt. The compositions may be suitable for administration by any suitable route including, for example, intradermal, subcutaneous, percutaneous, intramuscular, intra-arterial, intraperitoneal, intraarticular, intraosseous or other appropriate administration routes. Preferred compositions are suitable for administration by intravenous infusion.

Methods of Use of Polypeptides

The invention provides for the use of polypeptides of the invention in various methods. For example, the present polypeptides may provide useful tools for biotechnology. The polypeptides may be used for specific ex vivo cleavage of IgG, in particular human IgG. In such a method, the polypeptide may be incubated with a sample containing IgG under conditions which permit the specific cysteine protease activity to occur. Specific cleavage can be verified, and the cleavage products isolated using any suitable method, such as those described in WO2003051914 and WO2009033670. Thus the method can be used in particular to generate Fc and F(ab')$_2$ fragments. Fab fragments may then be produced by carrying out a reduction step (for example in 2-mercaptoethanolamine or Cysteamine) on the F(ab')$_2$ fragments that result from cleavage of IgG with a polypeptide of the invention.

The method may also be used to detect or analyse IgG in a sample, or to remove IgG from a sample. A method for the detection of IgG in a sample typically involves incubating the polypeptide with the sample under conditions which permit IgG-specific binding and cleavage. The presence of IgG can be verified by detection of the specific IgG cleavage products, which may subsequently be analysed.

The polypeptides in accordance with the present invention may also be used in therapy or prophylaxis. In therapeutic applications, polypeptides or compositions are administered to a subject already suffering from a disorder or condition, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as "therapeutically effective amount". In prophylactic applications, polypeptides or compositions are administered to a subject not yet exhibiting symptoms of a disorder or condition, in an amount sufficient to prevent or delay the development of symptoms. Such an amount is defined as a "prophylactically effective amount". The subject may have been identified as being at risk of developing the disease or condition by any suitable means. Thus the invention also provides a polypeptide of the invention for use in the treatment of the human or animal body. Also provided herein is a method of prevention or treatment of disease or condition in a subject, which method comprises administering a polypeptide of the invention to the subject in a prophylactically or therapeutically effective amount. The polypeptide may be co-administered with an immune-suppressive agent. The polypeptide is preferably administered by intravenous infusion, but may be administered by any suitable route including, for example, intradermal, subcutaneous, percutaneous, intramuscular, intra-arterial, intraperitoneal, intraarticular, intraosseous or other appropriate administration routes. The amount of said polypeptide that is administered may have a lower limit of about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25 mg/kg BW. The amount of said polypeptide that is administered may have an upper limit of about 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 mg/kg BW. It would be understood that any of the above mentioned upper limits may be combined with any of the above lower limits to provide a range for the dose that is administered. For example, the amount of said polypeptide that is administered may be between about 0.01 mg/kg BW and 2 mg/kg BW, between 0.10 and 1 mg/kg BW, and preferably between 0.25 mg/kg BW and 0.5 mg/kg BW. The polypeptide may be administered on multiple occasions to the same subject, provided that the quantity of ADA in the serum of the subject which is capable of binding to the polypeptide does not exceed a threshold determined by the clinician. The quantity of ADA in the serum of the subject which is capable of binding to the polypeptide may be determined by any suitable method, such as an agent specific CAP FEIA (ImmunoCAP) test or a titre assay.

Polypeptides of the invention may be particularly useful in the treatment or prevention of a disease or condition mediated by pathogenic IgG antibodies. Accordingly, the invention provides a polypeptide of the invention for use in the treatment or prevention of a disease or condition mediated by pathogenic IgG antibodies. The invention also provides a method of treating or preventing a disease or condition mediated by pathogenic IgG antibodies comprising administering to an individual a polypeptide of the invention. The method may comprise repeat administration of the said polypeptide. The invention also provides a polypeptide of the invention for use in the manufacture of a medicament for the treatment or prevention of a disease or condition mediated by pathogenic IgG antibodies.

The pathogenic antibodies may typically be specific for an antigen which is targeted in an autoimmune disease or other condition mediated wholly or in part by antibodies. Table D sets out a list of such diseases and the associated antigens. A polypeptide of the invention may be used to treat any of these diseases or conditions. The polypeptide is particularly effective for the treatment or prevention of autoimmune disease which is mediated in whole or in part by pathogenic IgG antibodies.

TABLE D

| DISEASE | AUTOANTIGENS |
| --- | --- |
| Addison's disease | Steroid 21-hydroxylase, 17 alpha-Hydroxylase (17OH) and side-chain-cleavage enzyme (P450scc), Thyroperoxidase, thyroglobulin and H+/K(+)– |
| Anti-GBM glomerulonephritis (related to Goodpasteur) | Anti-glomerular basement membrane (anti-GBM): noncollagenous (NC1) domains of the alpha3alpha4alpha5(IV) collagen |
| Anti-neutrophil cytoplasmic antibody-associated vasculitides (ANCA associated vasculitis)(Wegener granulomatosis, Churg-Strauss syndrome, microscopic polyangiitis) | Myeloperoxidase, proteinase 3 |
| Anti-NMDAR Encephalitis | N-methyl-D-aspartate receptor (NMDAR) |
| Anti-phospholipid antibody syndrome (APS) and catastrophic APS | Negatively-charged phospholipids complexed with phospholipid binding plasma proteins (e.g. beta2GPI), cardiolipin, beta2-glycoprotein I, and (beta2GPI) |
| Autoimmune bullous skin diseases (Pemphigus). Pemphigus foliaceus (PF), fogo selvagem (FS)(endemic form), pemphigus vulgaris (PV) | IgG against keratinocytes. Specific target is desmoglein (Dsg) 1 (desmosomal Cadherins) |
| Autoimmune hemolytic anemia (AIHA) | Self-antigens on red-blood-cells |
| Autoimmune hepatitis (AIH) | Actin, antinuclear antibody (ANA), smooth muscle antibody (SMA), liver/kidney microsomal antibody (LKM-1), anti soluble liver antigen (SLA/LP) and anti-mitochondrial antibody (AMA), CYP2D6, CYP2C9-tienilic acid, UGT1A, CYP1A2, CYP2A6, CYP3A, CYP2E1, CYP11A1, CYP17 and CYP21 |
| Autoimmune neutropenia (AIN) | FcgRIIIb |
| Bullous pemphigoid (BP) | Hemidesmosomal proteins BP230 and BP180 (type XVII collagen), laminin 5, the alpha6 subunit of the integrin alpha6beta4 and p200 |
| Celiac disease | transglutaminase 2 (TG2), transglutaminase 3, actin, ganglioside, collagen, calreticulin and zonulin, thyroid, endocrine pancreas, anti-gastric and liver, anti-nuclear constituents, anti-reticulin, actin, smooth muscle, calreticulin, desmin, collagens, bone, anti-brain, ganglioside, neuronal, blood vessel |
| Chronic utricaria | Alpha-subunit of the high-affinity IgE receptor, IgE |
| Complete congenital heart block (CCHB) | Ro (Sjögens syndrome antigen A (SSA)), La (Sjögens syndrome antigen B(SSB)) |
| Diabetes type 1A (T1DM) | Islet cell autoantibodies (ICA), antibodies to insulin (IAA), glutamic acid decarboxylase (GAA or GAD), protein tyrosine phosphatase (IA2 or ICA512), Insulinoma Associated Peptide-2. The number of antibodies, rather than the individual antibody, is thought to be most predictive of progression to overt diabetes. |
| Epidermolysis bullosa acquisita (EBA) | The 145-kDa noncollagenous aminoterminal (NC-1) domain of collagen VII |
| Essential mixed cryoglobulinemia | Essential mixed cryoglobulinemia antigens |
| Goodpasture's syndrome (also known as Goodpasture's disease and anti-glomerular basement membrane disease | alpha3(IV) collagen (=Goodpasture antigen) |
| Graves'disease (Basedow's disease), includes Goitre and hyperthyroidism, infiltrative exopthalmos and infiltarative dermopathy. | Thyrotropin receptor (TSHR) Thyroid peroxidase (TPO) |
| Guillain-Barré syndrome (GBS). Acute inflammatory demyelinating polyneuropathy (AIDP), acute motor axonal neuropathy (AMAN) | Gangliosides GM1, GM1b, GD1a, and GalNAc-GD1a, glycosphingolipid, myelin proteins PMP22 and P0 |
| Hemophilia - Acquired FVIII deficiency | Factor VIII |

TABLE D-continued

| DISEASE | AUTOANTIGENS |
| --- | --- |
| Idiopathic thrombocytopenic purpura (ITP) | Platelet glycoprotein (GP) IIb-IIIa and/or GPIb-IX |
| Lambert-Eaton myasthenic syndrome (LEMS) | voltage gated calcium channels |
| Mixed Connective Tissue Disease (MCTD) | IgG directed against the spliceosome, U1-snRNP |
| Multiple Myeloma | Multiple Myeloma antigens |
| Myasthenia gravis Myasthenic crisis | Acetylcholine receptors (AchR), muscle-specific kinase (MuSK) |
| Myocarditis, dilated cardiomyopathy (DCM)(congestive cardiomyopathy) | heart-reactive autoantibodies against multiple antigens e.g. cardiac myosin |
| Neuromyelitis Optica (NMO) | Aquaporin 4 (AQP4) |
| Primary biliary cirrhosis (PBC) | pyruvate dehydrogenase complex (PDC)-E2 and other members of the oxaloacid dehydrogenase family, Glycoprotein-210, p62, sp100 |
| Primary Progressive Multiple Sclerosis (PPMS) | Myelin oligodendrocyte glycoprotein (MOG), Myelin proteolipid protein (PLP), transketolase (TK), cyclic nucleotide phosphodiesterase type I (CNPase I), collapsin response mediator protein 2, tubulin beta4, neurofascin |
| Rheumatic heart disease (RHD), (Rheumatic fever) | Cardiac myosin |
| Rheumatoid Arthritis (RA) | Type II collagen, citrullin (-ated proteins (e.g. (fibrinogen, vimentin, filaggrin, type II collagen, enolase)), G6PI, RFs (anti-Fc/IgG), Vimentin, and cytokeratin |
| Serum-sickness, immune complex hypersensitivity (type III) | Various antigens |
| Sjögren Syndrome (SS) | Ro (Sjögens syndrome antigen A (SS-A)), La (Sjögens syndrome antigen B(SS-B)), p80 coilin, antinuclear antibodies, anti-thyroid, anti-centromere antibodies (Raynaud's phenomenon), anti-carbonic anhydrase II (distal renal tubular acidosis), anti-mitochondrial antibodies (liver pathology), cryoglobulins (evolution to non-Hodgkin's lymphoma), alpha- and beta-fodrin, islet cell autoantigen, poly(ADP)ribose polymerase (PARP), NuMA, Golgins, NOR-90, M3-muscarinic receptor |
| SLE including Lupus nephritis | Autoantibodies to nuclear constituents (e.g. dsDNA and nucleosomes), dsDNA, PARP, Sm, PCDA, rRNA Ribosome P proteins, C1q |
| Stiff-person syndrome (SPS) | glutamic acid decarboxylase (GAD), amphiphysin. |
| Systemic sclerosis (scleroderma) | DNA-topoisomerase I (Scl-70), U3 snRNP, U2 snRNP, 7-2 RNP, NOR-90, centromere-associated proteins, and nucleolar antigens, Anti-Th/To, Anti-RNA polymerase I/III, Anti-PDGF receptor, Anti-fibrillin-1, M3-muscarinic receptor, |
| Transplant rejection | Transplant rejection antigens |
| Thrombotic Thrombocytopenic Purpura (TTP) | ADAMTS13 |

In another embodiment, a polypeptide of the invention may be used in a method to improve the benefit to a subject of a therapy or a therapeutic agent. The method comprises two steps, which are referred to herein as steps (a) and (b).

Step (a) comprises administering to the subject a polypeptide of the invention. The amount of the polypeptide administered is preferably sufficient to cleave substantially all IgG molecules present in the plasma of the subject. Step (b) comprises subsequently administering to the subject the said therapy or therapeutic agent. Steps (a) and (b) are separated by a time interval which is preferably sufficient for cleavage of substantially all IgG molecules present in the plasma of the subject to take place. The said interval may typically be of at least 30 minutes and at most 21 days.

The therapeutic agent of which the benefit is improved is typically an antibody which is administered for the treatment of cancer or another disease. The therapeutic agent may be IVIg. In the context of this embodiment, the invention may be alternatively described as providing a method for the treatment of cancer or another disease in a subject, the method comprising (a) administering to the subject a polypeptide of the invention; and (b) subsequently administering to the subject a therapeutically effective amount of an antibody which is a treatment for said cancer or said other disease; wherein:
the amount of said polypeptide administered is sufficient to cleave substantially all IgG molecules present in the plasma of the subject; and
steps (a) and (b) are separated by a time interval of at least 2 hours and at most 21 days.

In other words, the invention also provides the polypeptide for use in such a method for the treatment of cancer or another disease. The invention also provides use of the agent in the manufacture of a medicament for the treatment of cancer or another disease by such a method. The cancer may be Acute lymphoblastic leukemia, Acute myeloid leukemia, Adrenocortical carcinoma, AIDS-related cancers, AIDS-related lymphoma, Anal cancer, Appendix cancer, Astrocytoma, childhood cerebellar or cerebral, Basal cell carcinoma, Bile duct cancer, extrahepatic, Bladder cancer, Bone cancer, Osteosarcoma/Malignant fibrous histiocytoma, Brainstem glioma, Brain cancer, Brain tumor, cerebellar astrocytoma, Brain tumor, cerebral astrocytoma/malignant glioma, Brain tumor, ependymoma, Brain tumor, medulloblastoma, Brain tumor, supratentorial primitive neuroectodermal tumors, Brain tumor, visual pathway and hypothalamic glioma, Breast cancer, Bronchial adenomas/carcinoids, Burkitt lymphoma, Carcinoid tumor, Carcinoid tumor, gastrointestinal, Carcinoma of unknown primary, Central nervous system lymphoma, Cerebellar astrocytoma, Cerebral astrocytoma/Malignant glioma, Cervical cancer, Chronic lymphocytic leukemia, Chronic myelogenous leukemia Chronic myeloproliferative disorders, Colon Cancer, Cutaneous T-cell lymphoma, Desmoplastic small round cell tumor, Endometrial cancer, Ependymoma, Esophageal cancer, Ewing's sarcoma in the Ewing family of tumors, Extracranial germ cell tumor, Childhood, Extragonadal Germ cell tumor, Extrahepatic bile duct cancer, Eye Cancer, Intraocular melanoma, Eye Cancer, Retinoblastoma, Gallbladder cancer, Gastric (Stomach) cancer, Gastrointestinal Carcinoid Tumor, Gastrointestinal stromal tumor (GIST), Germ cell tumor: extracranial, extragonadal, or ovarian, Gestational trophoblastic tumor, Glioma of the brain stem, Glioma, Childhood Cerebral Astrocytoma, Glioma, Childhood Visual Pathway and Hypothalamic, Gastric carcinoid, Hairy cell leukemia, Head and neck cancer, Heart cancer, Hepatocellular (liver) cancer, Hodgkin lymphoma, Hypopharyngeal cancer, Hypothalamic and visual pathway glioma, Intraocular Melanoma, Islet Cell Carcinoma (Endocrine Pancreas), Kaposi sarcoma, Kidney cancer (renal cell cancer), Laryngeal Cancer, Leukemias, Leukemia, acute lymphoblastic (also called acute lymphocytic leukemia), Leukemia, acute myeloid (also called acute myelogenous leukemia), Leukemia, chronic lymphocytic (also called chronic lymphocytic leukemia), Leukemia, chronic myelogenous (also called chronic myeloid leukemia), Leukemia, hairy cell, Lip and Oral Cavity Cancer, Liposarcoma, Liver Cancer (Primary), Lung Cancer, Non-Small Cell Lung Cancer, Small Cell, Lymphomas, Lymphoma, AIDS-related, Lymphoma, Burkitt, Lymphoma, cutaneous T-Cell, Lymphoma, Hodgkin, Lymphomas, Non-Hodgkin (an old classification of all lymphomas except Hodgkin's), Lymphoma, Primary Central Nervous System, Macroglobulinemia, Waldenström, Malignant Fibrous Histiocytoma of Bone/Osteosarcoma, Medulloblastoma, Melanoma, Melanoma, Intraocular (Eye), Merkel Cell Carcinoma, Mesothelioma, Adult Malignant, Mesothelioma, Metastatic Squamous Neck Cancer with Occult Primary, Mouth Cancer, Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Myelogenous Leukemia, Chronic, Myeloid Leukemia, Adult Acute, Myeloid Leukemia, Childhood Acute, Myeloma, Multiple (Cancer of the Bone-Marrow), Myeloproliferative Disorders, Nasal cavity and paranasal sinus cancer, Nasopharyngeal carcinoma, Neuroblastoma, Non-Hodgkin lymphoma, Non-small cell lung cancer, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, Pancreatic cancer, islet cell, Paranasal sinus and nasal cavity cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Renal pelvis and ureter, transitional cell cancer, Retinoblastoma, Rhabdomyosarcoma, Salivary gland cancer, Sarcoma, Ewing family of tumors, Kaposi Sarcoma, Sarcoma, soft tissue, Sarcoma, uterine, Sézary syndrome, Skin cancer (nonmelanoma), Skin cancer (melanoma), Skin carcinoma, Merkel cell, Small cell lung cancer, Small intestine cancer, Soft tissue sarcoma, Squamous cell carcinoma, Squamous neck cancer with occult primary, metastatic, Stomach cancer, Supratentorial primitive neuroectodermal tumor, T-Cell lymphoma, cutaneous—see Mycosis Fungoides and Sézary syndrome, Testicular cancer, Throat cancer, Thymoma, Thymoma and Thymic carcinoma, Thyroid cancer, Thyroid cancer, Transitional cell cancer of the renal pelvis and ureter, Trophoblastic tumor, Ureter and renal pelvis, transitional cell cancer Urethral cancer, Uterine cancer, endometrial, Uterine sarcoma, Vaginal cancer, Visual pathway and hypothalamic glioma, Vulvar cancer, Waldenström macroglobulinemia and Wilms tumor (kidney cancer).

The cancer is preferably prostate cancer, breast cancer, bladder cancer, colon cancer, rectal cancer, pancreatic cancer, ovarian cancer, lung cancer, cervical cancer, endometrial cancer, kidney (renal cell) cancer, oesophageal cancer, thyroid cancer, skin cancer, lymphoma, melanoma or leukemia.

The antibody administered in step (b) is preferably specific for a tumour antigen associated with one or more of the above cancer types. Targets of interest for an antibody for use in the method include CD2, CD3, CD19, CD20, CD22, CD25, CD30, CD32, CD33, CD40, CD52, CD54, CD56, CD64, CD70, CD74, CD79, CD80, CD86, CD105, CD138, CD174, CD205, CD227, CD326, CD340, MUC16, GPNMB, PSMA, Cripto, ED-B, TMEFF2, EphA2, EphB2, FAP, av integrin, Mesothelin, EGFR, TAG-72, GD2, CA1X, 5T4, α4β7 integrin, Her2. Other targets are cytokines, such as interleukins IL-I through IL-13, tumour necrosis factors α and β, interferons α, β and γ, tumour growth factor Beta (TGF-β), colony stimulating factor (CSF) and granulocyte monocyte colony stimulating factor (GMCSF). See Human Cytokines: Handbook for Basic & Clinical Research (Aggrawal et al. eds., Blackwell Scientific, Boston, MA 1991). Other targets are hormones, enzymes, and intracellular and intercellular messengers, such as, adenyl cyclase, guanyl cyclase, and phospholipase C. Other targets of interest are leukocyte antigens, such as CD20, and CD33. Drugs may also be targets of interest. Target molecules can be human, mammalian or bacterial. Other targets are antigens, such as proteins, glycoproteins and carbohydrates from microbial pathogens, both viral and bacterial, and tumors. Still other targets are described in U.S. Pat. No. 4,366,241.

The antibody may be attached directly or indirectly to a cytotoxic moiety or to a detectable label. The antibody may be administered via one or more routes of administration using one or more of a variety of methods known in the art. The route and/or mode of administration will vary depending upon the desired results. Preferred routes of administration for antibodies include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection. Alternatively, an antibody can be administered via a non-parenteral route, such as a topical, epidermal or mucosal route of administration. Local administration is also preferred, including peritumoral, juxtatumoral, intratumoral, intralesional, perilesional, intra cavity infusion, intravesicle administration, and inhalation.

A suitable dosage of an antibody of the invention may be determined by a skilled medical practitioner. Actual dosage levels of an antibody may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular antibody employed, the route of administration, the time of administration, the rate of excretion of the antibody, the duration of the treatment, other drugs, compounds and/or materials used in combination with the particular compositions employed, the age, sex, weight, condition, general health and prior medical history of the patient being treated, and like factors well known in the medical arts.

A suitable dose of an antibody may be, for example, in the range of from about 0.1 µg/kg to about 100 mg/kg body weight of the patient to be treated. For example, a suitable dosage may be from about 1 µg/kg to about 10 mg/kg body weight per day or from about 10 µg/kg to about 5 mg/kg body weight per day.

Dosage regimens may be adjusted to provide the optimum desired response (e.g., a therapeutic response). For example, a single bolus may be administered, or step (b) of the method may comprise several divided doses administered over time or the dose may be proportionally reduced or increased as indicated by the exigencies of the therapeutic situation, provided the required interval between steps (a) and (b) is not exceeded. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The antibody of step (b) may be administered in combination with chemotherapy or radiation therapy. The method may further comprises the administration of an additional anti-cancer antibody or other therapeutic agent, which may be administered together with the antibody of step (b) in a single composition or in separate compositions as part of a combined therapy. For example, the antibody of step (b) may be administered before, after or concurrently with the other agent.

The antibody may be Abagovomab, Abciximab, Actoxumab, Adalimumab, Adecatumumab, Afelimomab, Afutuzumab, Alacizumab pegol, ALD518, Alemtuzumab, Alirocumab, Altumomab pentetate, Amatuximab, Anatumomab mafenatox, Anrukinzumab, Apolizumab, Arcitumomab, Aselizumab, Atinumab, Atlizumab (=tocilizumab), Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, CC49, Cedelizumab, Certolizumab pegol, Cetuximab, Ch.14.18, Citatuzumab bogatox, Cixutumumab, Clazakizumab, Clenoliximab, Clivatuzumab tetraxetan, Conatumumab, Concizumab, Crenezumab, CR6261, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Elotuzumab Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab Farletuzumab, Fasinumab, FBTA05, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, GS6624, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Obinutuzumab, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN1412, Ticilimumab (=tremelimumab), Tildrakizumab, Tigatuzumab, TNX-650, Tocilizumab (=atlizumab), Toralizumab, Tositumomab, Tralokinumab, Trastuzumab, TRBS07, Tregalizumab, Tremelimumab Tucotuzumab celmoleukin, Tuvirumab, Ublituximab, Urelumab, Urtoxazumab, Ustekinumab, Vapaliximab, Vatelizumab, Vedolizumab, Veltuzumab, Vepalimomab Vesencumab, Visilizumab, Volociximab, Vorsetuzumab mafodotin, Votumumab, Zalutumumab, Zanolimumab, Zatuximab, Ziralimumab or Zolimomab aritox.

Preferred antibodies include Natalizumab, Vedolizumab, Belimumab, Atacicept, Alefacept, Otelixizumab, Teplizumab, Rituximab, Ofatumumab, Ocrelizumab, Epratuzumab, Alemtuzumab, Abatacept, Eculizamab, Omalizumab, Canakinumab, Meplizumab, Reslizumab, Tocilizumab, Ustekinumab, Briakinumab, Etanercept, Inlfliximab, Adalimumab, Certolizumab pegol, Golimumab, Trastuzumab, Gemtuzumab, Ozogamicin, Ibritumomab, Tiuxetan, Tositumomab, Cetuximab, Bevacizumab, Panitumumab, Denosumab, Ipilimumab, Brentuximab and Vedotin.

The therapy of which the benefit is improved is typically an organ transplant. The organ may be selected from kidney, liver, heart, pancreas, lung, or small intestine. The subject to be treated may preferably be sensitized or highly sensitized. By "sensitized" it is meant that the subject has developed antibodies to human major histocompatibility (MHC) antigens (also referred to as human leukocyte antigens (HLA)). The anti-HLA antibodies originate from allogenically sensitized B-cells and are usually present in patients that have previously been sensitized by blood transfusion, previous transplantation or pregnancy (Jordan et al., 2003).

Whether or not a potential transplant recipient is sensitized may be determined by any suitable method. For example, a Panel Reactive Antibody (PRA) test may be used to determine if a recipient is sensitized. A PRA score >30% is typically taken to mean that the patient is "high immunologic risk" or "sensitized". Alternatively, a cross match test may be conducted, in which a sample of the potential transplant donor's blood is mixed with that of the intended recipient. A positive cross-match means that the recipient has antibodies which react to the donor sample, indicating that the recipient is sensitized and transplantation should not occur. Cross-match tests are typically conducted as a final check immediately prior to transplantation.

The presence of high titer antibodies against MHC antigens of the potential donor (i.e. donor specific antibodies (DSA)) is a direct contraindication to transplantation because of the risk of acute antibody-mediated rejection. In short, sensitization to donor MHC antigens hampers the identification of a suitable donor. A positive cross-match test is an unambiguous barrier to transplantation. Since approximately one third of patients waiting for kidney transplantation are sensitized, with as many as 15% being highly sensitized, this leads to an accumulation of patients waiting for transplant. In the US, the median time on the waiting list for renal transplantation in 2001-2002 was 1329 days for those with Panel Reactive Antibody (PRA) score 0-9%, 1920 days for those with PRA 10-79%, and 3649 days for those with PRA 80% or greater (OPTN-database, 2011).

One accepted strategy to overcome the DSA barrier is to apply plasma exchange or immune adsorption, often in combination with e.g. intravenous gamma globulin (IVIg) or Rituximab, to lower the levels of DSA to a level where transplantation can be considered (Jordan et al., 2004; Montgomery et al., 2000; Vo et al., 2008a; Vo et al., 2008b). However, plasma exchange, immune adsorption and IVIg treatments have the disadvantage of being inefficient and requiring rigorous planning since they involve repeated treatments over an extended period of time. When an organ from a deceased donor becomes available it has to be transplanted within hours since prolonged cold ischemia time is one of the most important risk factors for delayed graft function and allograft loss in renal transplantation (Ojo et al., 1997).

By contrast, the method of the present invention allows the rapid, temporary and safe removal of DSAs in a potential transplant recipient. Administering the polypeptide of the invention just prior to transplantation has the capacity to effectively desensitize a highly sensitized patient, thereby allowing transplantation and avoiding acute antibody-mediated rejection. A single dose of polypeptide prior to transplantation will enable transplantation of thousands of patients with donor specific IgG antibodies.

In the context of this embodiment, the method may be alternatively described as a method for the treatment of organ failure in a subject, the method comprising (a) administering to the subject a polypeptide of the invention and (b) subsequently transplanting a replacement organ into the subject; wherein:

the amount of said polypeptide administered is sufficient to cleave substantially all IgG molecules present in the plasma of the subject; and steps (a) and (b) are separated by a time interval of at least 2 hours and at most 21 days.

In other words, this embodiment may be described as a method for preventing rejection of a transplanted organ in a subject, particularly acute antibody-mediated transplant rejection, the method comprising, at least 2 hours and at most 21 days prior to transplantation of the organ, administering to the subject a polypeptide of the invention, wherein the amount of said polypeptide administered is sufficient to cleave substantially all IgG molecules present in the plasma of the subject. The invention also provides use of the polypeptide of the invention in such a method of treating organ failure or preventing transplant rejection, particularly acute antibody-mediated transplant rejection. The invention also provides use of the polypeptide of the invention in the manufacture of a medicament for the treatment of organ failure or for the prevention of transplant rejection by such a method. In this embodiment, the method of the invention may additionally comprise a step conducted at or immediately prior to transplantation, which step comprises induction suppression of T cells and/or B cells in the patient. Said induction suppression may typically comprise administering an effective amount of an agent which kills or inhibits T cells, and/or administering an effective amount of an agent which kills or inhibits B cells. Agents which kill or inhibit T cells include Muromonab, Basiliximab, Daclizumab, an antithymocyte globulin (ATG) antibody and a lymphocyte immune globulin, anti-thymocyte globulin preparation (ATGAM). Rituximab is known to kill or inhibit B cells.

EXAMPLES

Unless indicated otherwise, the methods used are standard biochemistry and molecular biology techniques. Examples of suitable methodology textbooks include Sambrook et al., Molecular Cloning, A Laboratory Manual (1989) and Ausubel et al., Current Protocols in Molecular Biology (1995), John Wiley and Sons, Inc.

Example 1—Design of Polypeptides, Production and Purification

The mature IdeS molecule was analysed and regions suitable for mutation were identified. In some cases an in silico assessment was used to evaluate the likely outcome of a mutation. Having decided on the sequence of each polypeptide, cDNA encoding each polypeptide were generated at GeneCust, Luxembourg either by site-directed mutation of a starting sequence or synthesis depending on the number of mutations introduced. cDNA were sequenced and transferred to the pET9a expression vector (Novagene) in frame with a C-terminal 6× His-tag, joined to the C-terminus by a short glycine linker (3× Gly). N terminal methionine was added to improve bacterial expression. The plasmids were transformed (heat-shock) into E. coli BL21(DE3) (Stratagene) and seeded on LB agarose plates containing 30 µg/ml kanamycin. Single colonies were picked and overnight cultures (3 ml LB-medium) were started at 37° C., 250 rpm. The following day glycerol stocks were prepared and 10 ml TB-medium supplemented with 30 µg/ml kanamycin and anti-foam were inoculated with overnight culture and grown until OD 0.6-0.8 (37° C., 300 rpm). At this point IPTG (1 mM) was added and cultures were continued for 1 hour prior to harvest of the bacteria by centrifugation. The pellets were washed in PBS and frozen at −20° C. A freeze-thaw protocol for bacterial lysis was used (three freeze/thaw cycles in 1 ml PBS each) and the proteins were purified using Ni-NTA pre-packed spin-columns (Pierce). After purification the eluted proteins were activated with 10 mM DTT prior to buffer exchange (3 volumes PBS in MWCO 9K Millipore cfg devises). The purity and stability of each protein was evaluated using sodium dodecyl sulphate polyacrylamide gel electrophoreses (SDS-PAGE) stainless 12% Mini-PROTEAN®TGX™precast gel (Biorad) SDS-PAGE The following table summarises the changes made for each tested polypeptide relative to mature IdeS, not including the additional N terminal methionine and his tag. Thus, the sequence of each polypeptide used in the experiments described herein typically comprises the sequence of the SEQ ID NO as indicated in the table, plus an additional N terminal methionine and a his tag joined to the C terminal end by a short glycine linker.

As a control, a version of IdeS was produced using the same methodology as described above. This version of IdeS comprises the sequence of SEQ ID NO: 2 plus an additional N terminal methionine and a his tag joined to the C terminal end by a short glycine linker. This version of IdeS may be referred to herein as pCART124. The sequence of pCART124 is provided below:

(SEQ ID NO: 17)
MDSFSANQEIRYSEVTPYHVTSVWTKGVTPPANFTQGEDVFHAPY

VANQGWYDITKTFNGKDDLLCGAATAGNMLHWWFDQNKDQIKRYL

EEHPEKQKINFNGEQMFDVKEAIDTKNHQLDSKLFEYFKEKAFPY

LSTKHLGVFPDHVIDMFINGYRLSLTNHGPTPVKEGSKDPRGGIF

DAVFTRGDQSKLLTSRHDFKEKNLKEISDLIKKELTEGKALGLSH

TYANVRINHVINLWGADFDSNGNLKAIYVTDSDSNASIGMKKYFV

GVNSAGKVAISAKEIKEDNIGAQVLGLFTLSTGQDSWNQTNGGGH

HHHHH

IdeS lacking tag was also independently produced to GMP standard using automated multistep chromatographic purification, for use as a further control. This polypeptide is referred to herein as BX1001865.

The cDNA sequence used to produce each of the tested polypeptides and pCART124 is provided below. Each cDNA sequence includes at the 3' end a codon for the N terminal methionine (ATG) and, prior to the stop codon (TAA) at the 5' end, codons for the glycine linker and the histidine tag.

| Internal reference | Modifications relative to IdeS (positions correspond to SEQ ID NO: 1) | SEQ ID NO |
|---|---|---|
| pCART152 | N130R | 3 |
| pCART183 | N130K, E198R, D216N | 4 |
| pCART184 | N130R, E198K, D216N, S302K | 5 |
| pCART185 | E119R, D216N, T244D | 6 |
| pCART186 | E119K, D142R, D216N, T244E, S302K | 7 |
| pCART187 | K115E, D216N, K241E, E245K, D316K, D333K | 8 |
| pCART188 | E119K, N130R, D142R, D216N, K241S, T244E, E245N, S302K | 9 |
| pCART189 | E119K, N130R, D142R, E198K, D216N, T244E | 10 |
| pCART190 | K115E, N130R, E198K, D216N, K241E, E245K, D333K | 11 |
| pCART209 | N336_N339del (NQTN deletion) | 12 |
| pCART125 | D30_T49del (DSFSANQEIR YSEVTPYHVT deletion) | 13 |
| pCART213 | D30_T49del (DSFSANQEIR YSEVTPYHVT deletion), N130K, D216N | 14 |
| pCART214 | D30_T49del (DSFSANQEIR YSEVTPYHVT deletion), K115E, N130K, E139K, D216N, K241E, E245K, D333K | 15 |
| pCART228 | S31_T49replZ (replace SEQ ID NO: 35 with SEQ ID NO: 36), K115E, N130K, E139K, D216N, K241E, E245K, D333K | 16 | pCART124

(IdeS; SEQ ID NO: 20)
ATGGATAGTTTTTCTGCTAATCAAGAGATTAGATATTCGGAAGTAACACCTTATCACGTTACTTCCGTTTGGACC

AAAGGAGTTACTCCTCCAGCAAACTTCACTCAAGGTGAAGATGTTTTTCACGCTCCTTATGTTGCTAACCAAGGA

TGGTATGATATTACCAAAACATTCAATGGAAAAGACGATCTTCTTTGCGGGGCTGCCACAGCAGGGAATATGCTT

CACTGGTGGTTCGATCAAAACAAAGACCAAATTAAACGTTATTTGGAAGAGCATCCAGAAAAGCAAAAATAAAC

TTCAATGGCGAACAGATGTTTGACGTAAAAGAAGCTATCGACACTAAAAACCACCAGCTAGATAGTAAATTATTT

GAATATTTTAAAGAAAAGCTTTCCCTTATCTATCTACTAAACACCTAGGAGTTTTCCCTGATCATGTAATTGAT

ATGTTCATTAACGGCTACCGCCTTAGTCTAACTAACCACGGTCCAACGCCAGTAAAAGAAGGTAGTAAAGATCCC

CGAGGTGGTATTTTTGACGCCGTATTTACAAGAGGTGATCAAAGTAAGCTATTGACAAGTCGTCATGATTTTAAA

GAAAAAAATCTCAAAGAAATCAGTGATCTCATTAAGAAAGAGTTAACCGAAGGCAAGGCTCTAGGCCTATCACAC

ACCTACGCTAACGTACGCATCAACCATGTTATAAACCTGTGGGGAGCTGACTTTGATTCTAACGGGAACCTTAAA

GCTATTTATGTAACAGACTCTGATAGTAATGCATCTATTGGTATGAAGAAATACTTTGTTGGTGTTAATTCCGCT

GGAAAAGTAGCTATTTCTGCTAAAGAAATAAAAGAAGATAATATAGGTGCTCAAGTACTAGGGTTATTTACACTT

TCAACAGGGCAAGATAGTTGGAATCAGACCAATGGCGGTGGCCATCATCACCATCACCACTAA pCART152

(SEQ ID NO: 21)
ATGGATAGTTTTTCTGCTAATCAAGAGATTAGATATTCGGAAGTAACACCTTATCACGTTACTTCCGTTTGGACC

AAAGGAGTTACTCCTCCAGCAAACTTCACTCAAGGTGAAGATGTTTTTCACGCTCCTTATGTTGCTAACCAAGGA

TGGTATGATATTACCAAAACATTCAATGGAAAAGACGATCTTCTTTGCGGGGCTGCCACAGCAGGGAATATGCTT

CACTGGTGGTTCGATCAAAACAAAGACCAAATTAAACGTTATTTGGAAGAGCATCCAGAAAAGCAAAAATAAAC

TTCCGTGGCGAACAGATGTTTGACGTAAAAGAAGCTATCGACACTAAAAACCACCAGCTAGATAGTAAATTATTT

GAATATTTTAAAGAAAAGCTTTCCCTTATCTATCTACTAAACACCTAGGAGTTTTCCCTGATCATGTAATTGAT

ATGTTCATTAACGGCTACCGCCTTAGTCTAACTAACCACGGTCCAACGCCAGTAAAAGAAGGTAGTAAAGATCCC

CGAGGTGGTATTTTTGACGCCGTATTTACAAGAGGTGATCAAAGTAAGCTATTGACAAGTCGTCATGATTTTAAA

GAAAAAAATCTCAAAGAAATCAGTGATCTCATTAAGAAAGAGTTAACCGAAGGCAAGGCTCTAGGCCTATCACAC

ACCTACGCTAACGTACGCATCAACCATGTTATAAACCTGTGGGGAGCTGACTTTGATTCTAACGGGAACCTTAAA

GCTATTTATGTAACAGACTCTGATAGTAATGCATCTATTGGTATGAAGAAATACTTTGTTGGTGTTAATTCCGCT

GGAAAAGTAGCTATTTCTGCTAAAGAAATAAAAGAAGATAATATAGGTGCTCAAGTACTAGGGTTATTTACACTT

TCAACAGGGCAAGATAGTTGGAATCAGACCAATGGCGGTGGCCATCATCACCATCACCACTAA pCART183

(SEQ ID NO: 22)
ATGGATAGTTTTTCTGCTAATCAAGAGATTAGATATTCGGAAGTAACACCTTATCACGTTACTTCCGTTTGGACC

AAAGGAGTTACTCCTCCAGCAAACTTCACTCAAGGTGAAGATGTTTTTCACGCTCCTTATGTTGCTAACCAAGGA

TGGTATGATATTACCAAAACATTCAATGGAAAAGACGATCTTCTTTGCGGGGCTGCCACAGCAGGGAATATGCTT

CACTGGTGGTTCGATCAAAACAAAGACCAAATTAAACGTTATTTGGAAGAGCATCCAGAAAAGCAAAAATAAAC

TTCAAAGGCGAACAGATGTTTGACGTAAAAGAAGCTATCGACACTAAAAACCACCAGCTAGATAGTAAATTATTT

GAATATTTTAAAGAAAAGCTTTCCCTTATCTATCTACTAAACACCTAGGAGTTTTCCCTGATCATGTAATTGAT

ATGTTCATTAACGGCTACCGCCTTAGTCTAACTAACCACGGTCCAACGCCAGTAAAACGTGGTAGTAAAGATCCC

CGAGGTGGTATTTTTGACGCCGTATTTACAAGAGGTAACCAAAGTAAGCTATTGACAAGTCGTCATGATTTTAAA

GAAAAAAATCTCAAAGAAATCAGTGATCTCATTAAGAAAGAGTTAACCGAAGGCAAGGCTCTAGGCCTATCACAC

ACCTACGCTAACGTACGCATCAACCATGTTATAAACCTGTGGGGAGCTGACTTTGATTCTAACGGGAACCTTAAA

GCTATTTATGTAACAGACTCTGATAGTAATGCATCTATTGGTATGAAGAAATACTTTGTTGGTGTTAATTCCGCT

-continued

GGAAAAGTAGCTATTTCTGCTAAAGAAATAAAAGAAGATAATATAGGTGCTCAAGTACTAGGGTTATTTACACTT
TCAACAGGGCAAGATAGTTGGAATCAGACCAATGGCGGTGGCCATCATCACCATCACCACTAA pCART184
(SEQ ID NO: 23)
ATGGATAGTTTTTCTGCTAATCAAGAGATTAGATATTCGGAAGTAACACCTTATCACGTTACTTCCGTTTGGACC
AAAGGAGTTACTCCTCCAGCAAACTTCACTCAAGGTGAAGATGTTTTTCACGCTCCTTATGTTGCTAACCAAGGA
TGGTATGATATTACCAAAACATTCAATGGAAAAGACGATCTTCTTTGCGGGGCTGCCACAGCAGGGAATATGCTT
CACTGGTGGTTCGATCAAAACAAAGACCAAATTAAACGTTATTTGGAAGAGCATCCAGAAAAGCAAAAATAAAC
TTCCGTGGCGAACAGATGTTTGACGTAAAAGAAGCTATCGACACTAAAAACCACCAGCTAGATAGTAAATTATTT
GAATATTTTAAAGAAAAAGCTTTCCCTTATCTATCTACTAAACACCTAGGAGTTTTCCCTGATCATGTAATTGAT
ATGTTCATTAACGGCTACCGCCTTAGTCTAACTAACCACGGTCCAACGCCAGTAAAAAAAGGTAGTAAAGATCCC
CGAGGTGGTATTTTTGACGCCGTATTTACAAGAGGTAACCAAAGTAAGCTATTGACAAGTCGTCATGATTTTAAA
GAAAAAAATCTCAAAGAAATCAGTGATCTCATTAAGAAAGAGTTAACCGAAGGCAAGGCTCTAGGCCTATCACAC
ACCTACGCTAACGTACGCATCAACCATGTTATAAACCTGTGGGGAGCTGACTTTGATTCTAACGGGAACCTTAAA
GCTATTTATGTAACAGACTCTGATAGTAATGCATCTATTGGTATGAAGAAATACTTTGTTGGTGTTAATAAAGCT
GGAAAAGTAGCTATTTCTGCTAAAGAAATAAAAGAAGATAATATAGGTGCTCAAGTACTAGGGTTATTTACACTT
TCAACAGGGCAAGATAGTTGGAATCAGACCAATGGCGGTGGCCATCATCACCATCACCACTAA pCART185
(SEQ ID NO: 24)
ATGGATAGTTTTTCTGCTAATCAAGAGATTAGATATTCGGAAGTAACACCTTATCACGTTACTTCCGTTTGGACC
AAAGGAGTTACTCCTCCAGCAAACTTCACTCAAGGTGAAGATGTTTTTCACGCTCCTTATGTTGCTAACCAAGGA
TGGTATGATATTACCAAAACATTCAATGGAAAAGACGATCTTCTTTGCGGGGCTGCCACAGCAGGGAATATGCTT
CACTGGTGGTTCGATCAAAACAAAGACCAAATTAAACGTTATTTGCGTGAGCATCCAGAAAAGCAAAAATAAAC
TTCAATGGCGAACAGATGTTTGACGTAAAAGAAGCTATCGACACTAAAAACCACCAGCTAGATAGTAAATTATTT
GAATATTTTAAAGAAAAAGCTTTCCCTTATCTATCTACTAAACACCTAGGAGTTTTCCCTGATCATGTAATTGAT
ATGTTCATTAACGGCTACCGCCTTAGTCTAACTAACCACGGTCCAACGCCAGTAAAAGAAGGTAGTAAAGATCCC
CGAGGTGGTATTTTTGACGCCGTATTTACAAGAGGTAACCAAAGTAAGCTATTGACAAGTCGTCATGATTTTAAA
GAAAAAAATCTCAAAGAAATCAGTGATCTCATTAAGAAAGAGTTAGATGAAGGCAAGGCTCTAGGCCTATCACAC
ACCTACGCTAACGTACGCATCAACCATGTTATAAACCTGTGGGGAGCTGACTTTGATTCTAACGGGAACCTTAAA
GCTATTTATGTAACAGACTCTGATAGTAATGCATCTATTGGTATGAAGAAATACTTTGTTGGTGTTAATTCCGCT
GGAAAAGTAGCTATTTCTGCTAAAGAAATAAAAGAAGATAATATAGGTGCTCAAGTACTAGGGTTATTTACACTT
TCAACAGGGCAAGATAGTTGGAATCAGACCAATGGCGGTGGCCATCATCACCATCACCACTAA pCART186
(SEQ ID NO: 25)
ATGGATAGTTTTTCTGCTAATCAAGAGATTAGATATTCGGAAGTAACACCTTATCACGTTACTTCCGTTTGGACC
AAAGGAGTTACTCCTCCAGCAAACTTCACTCAAGGTGAAGATGTTTTTCACGCTCCTTATGTTGCTAACCAAGGA
TGGTATGATATTACCAAAACATTCAATGGAAAAGACGATCTTCTTTGCGGGGCTGCCACAGCAGGGAATATGCTT
CACTGGTGGTTCGATCAAAACAAAGACCAAATTAAACGTTATTTGAAAGAGCATCCAGAAAAGCAAAAATAAAC
TTCAATGGCGAACAGATGTTTGACGTAAAAGAAGCTATCCGTACTAAAAACCACCAGCTAGATAGTAAATTATTT
GAATATTTTAAAGAAAAAGCTTTCCCTTATCTATCTACTAAACACCTAGGAGTTTTCCCTGATCATGTAATTGAT
ATGTTCATTAACGGCTACCGCCTTAGTCTAACTAACCACGGTCCAACGCCAGTAAAAGAAGGTAGTAAAGATCCC
CGAGGTGGTATTTTTGACGCCGTATTTACAAGAGGTAACCAAAGTAAGCTATTGACAAGTCGTCATGATTTTAAA
GAAAAAAATCTCAAAGAAATCAGTGATCTCATTAAGAAAGAGTTAGAAGAAGGCAAGGCTCTAGGCCTATCACAC

-continued

ACCTACGCTAACGTACGCATCAACCATGTTATAAACCTGTGGGGAGCTGACTTTGATTCTAACGGGAACCTTAAA

GCTATTTATGTAACAGACTCTGATAGTAATGCATCTATTGGTATGAAGAAATACTTTGTTGGTGTTAATAAAGCT

GGAAAAGTAGCTATTTCTGCTAAAGAAATAAAAGAAGATAATATAGGTGCTCAAGTACTAGGGTTATTTACACTT

TCAACAGGGCAAGATAGTTGGAATCAGACCAATGGCGGTGGCCATCATCACCATCACCACTAA pCART187 (SEQ ID NO: 26)

ATGGATAGTTTTTCTGCTAATCAAGAGATTAGATATTCGGAAGTAACACCTTATCACGTTACTTCCGTTTGGACC

AAAGGAGTTACTCCTCCAGCAAACTTCACTCAAGGTGAAGATGTTTTTCACGCTCCTTATGTTGCTAACCAAGGA

TGGTATGATATTACCAAAACATTCAATGGAAAAGACGATCTTCTTTGCGGGGCTGCCACAGCAGGGAATATGCTT

CACTGGTGGTTCGATCAAAACAAAGACCAAATTGAACGTTATTTGGAAGAGCATCCAGAAAAGCAAAAATAAAC

TTCAATGGCGAACAGATGTTTGACGTAAAAGAAGCTATCGACACTAAAAACCACCAGCTAGATAGTAAATTATTT

GAATATTTTAAAGAAAAAGCTTTCCCTTATCTATCTACTAAACACCTAGGAGTTTTCCCTGATCATGTAATTGAT

ATGTTCATTAACGGCTACCGCCTTAGTCTAACTAACCACGGTCCAACGCCAGTAAAAGAAGGTAGTAAAGATCCC

CGAGGTGGTATTTTTGACGCCGTATTTACAAGAGGTAACCAAAGTAAGCTATTGACAAGTCGTCATGATTTTAAA

GAAAAAATCTCAAAGAAATCAGTGATCTCATTAAGGAAGAGTTAACCAAAGGCAAGGCTCTAGGCCTATCACAC

ACCTACGCTAACGTACGCATCAACCATGTTATAAACCTGTGGGGAGCTGACTTTGATTCTAACGGGAACCTTAAA

GCTATTTATGTAACAGACTCTGATAGTAATGCATCTATTGGTATGAAGAAATACTTTGTTGGTGTTAATTCCGCT

GGAAAAGTAGCTATTTCTGCTAAAGAAATAAAAGAAAAAATATAGGTGCTCAAGTACTAGGGTTATTTACACTT

TCAACAGGGCAAAAAGTTGGAATCAGACCAATGGCGGTGGCCATCATCACCATCACCACTAA

PCART188 (SEQ ID NO: 27)

ATGGATAGTTTTTCTGCTAATCAAGAGATTAGATATTCGGAAGTAACACCTTATCACGTTACTTCCGTTTGGACC

AAAGGAGTTACTCCTCCAGCAAACTTCACTCAAGGTGAAGATGTTTTTCACGCTCCTTATGTTGCTAACCAAGGA

TGGTATGATATTACCAAAACATTCAATGGAAAAGACGATCTTCTTTGCGGGGCTGCCACAGCAGGGAATATGCTT

CACTGGTGGTTCGATCAAAACAAAGACCAAATTAAACGTTATTTGAAAGAGCATCCAGAAAAGCAAAAATAAAC

TTCCGTGGCGAACAGATGTTTGACGTAAAAGAAGCTATCCGTACTAAAAACCACCAGCTAGATAGTAAATTATTT

GAATATTTTAAAGAAAAAGCTTTCCCTTATCTATCTACTAAACACCTAGGAGTTTTCCCTGATCATGTAATTGAT

ATGTTCATTAACGGCTACCGCCTTAGTCTAACTAACCACGGTCCAACGCCAGTAAAAGAAGGTAGTAAAGATCCC

CGAGGTGGTATTTTTGACGCCGTATTTACAAGAGGTAACCAAAGTAAGCTATTGACAAGTCGTCATGATTTTAAA

GAAAAAATCTCAAAGAAATCAGTGATCTCATTAAGAGTGAGTTAGAAAACGGCAAGGCTCTAGGCCTATCACAC

ACCTACGCTAACGTACGCATCAACCATGTTATAAACCTGTGGGGAGCTGACTTTGATTCTAACGGGAACCTTAAA

GCTATTTATGTAACAGACTCTGATAGTAATGCATCTATTGGTATGAAGAAATACTTTGTTGGTGTTAATAAAGCT

GGAAAAGTAGCTATTTCTGCTAAAGAAATAAAAGAAGATAATATAGGTGCTCAAGTACTAGGGTTATTTACACTT

TCAACAGGGCAAGATAGTTGGAATCAGACCAATGGCGGTGGCCATCATCACCATCACCACTAA pCART189 (SEQ ID NO: 28)

ATGGATAGTTTTTCTGCTAATCAAGAGATTAGATATTCGGAAGTAACACCTTATCACGTTACTTCCGTTTGGACC

AAAGGAGTTACTCCTCCAGCAAACTTCACTCAAGGTGAAGATGTTTTTCACGCTCCTTATGTTGCTAACCAAGGA

TGGTATGATATTACCAAAACATTCAATGGAAAAGACGATCTTCTTTGCGGGGCTGCCACAGCAGGGAATATGCTT

CACTGGTGGTTCGATCAAAACAAAGACCAAATTAAACGTTATTTGAAAGAGCATCCAGAAAAGCAAAAATAAAC

TTCCGTGGCGAACAGATGTTTGACGTAAAAGAAGCTATCCGTACTAAAAACCACCAGCTAGATAGTAAATTATTT

GAATATTTTAAAGAAAAAGCTTTCCCTTATCTATCTACTAAACACCTAGGAGTTTTCCCTGATCATGTAATTGAT

ATGTTCATTAACGGCTACCGCCTTAGTCTAACTAACCACGGTCCAACGCCAGTAAAAAAGGTAGTAAAGATCCC

CGAGGTGGTATTTTTGACGCCGTATTTACAAGAGGTAACCAAAGTAAGCTATTGACAAGTCGTCATGATTTTAAA

```
GAAAAAAATCTCAAAGAAATCAGTGATCTCATTAAGAAAGAGTTAGAAGAAGGCAAGGCTCTAGGCCTATCACAC

ACCTACGCTAACGTACGCATCAACCATGTTATAAACCTGTGGGGAGCTGACTTTGATTCTAACGGGAACCTTAAA

GCTATTTATGTAACAGACTCTGATAGTAATGCATCTATTGGTATGAAGAAATACTTTGTTGGTGTTAATTCCGCT

GGAAAAGTAGCTATTTCTGCTAAAGAAATAAAAGAAGATAATATAGGTGCTCAAGTACTAGGGTTATTTACACTT

TCAACAGGGCAAGATAGTTGGAATCAGACCAATGGCGGTGGCCATCATCACCATCACCACTAA
``` pCART190

```
                                                             (SEQ ID NO: 29)
ATGGATAGTTTTTCTGCTAATCAAGAGATTAGATATTCGGAAGTAACACCTTATCACGTTACTTCCGTTTGGACC

AAAGGAGTTACTCCTCCAGCAAACTTCACTCAAGGTGAAGATGTTTTTCACGCTCCTTATGTTGCTAACCAAGGA

TGGTATGATATTACCAAAACATTCAATGGAAAAGACGATCTTCTTTGCGGGGCTGCCACAGCAGGGAATATGCTT

CACTGGTGGTTCGATCAAAACAAAGACCAAATTGAACGTTATTTGGAAGAGCATCCAGAAAAGCAAAAAATAAAC

TTCCGTGGCGAACAGATGTTTGACGTAAAAGAAGCTATCGACACTAAAAACCACCAGCTAGATAGTAAATTATTT

GAATATTTTAAAGAAAAAGCTTTCCCTTATCTATCTACTAAACACCTAGGAGTTTTCCCTGATCATGTAATTGAT

ATGTTCATTAACGGCTACCGCCTTAGTCTAACTAACCACGGTCCAACGCCAGTAAAAAAGGTAGTAAAGATCCC

CGAGGTGGTATTTTGACGCCGTATTTACAAGAGGTAACCAAAGTAAGCTATTGACAAGTCGTCATGATTTTAAA

GAAAAAATCTCAAAGAAATCAGTGATCTCATTAAGGAAGAGTTAACCAAAGGCAAGGCTCTAGGCCTATCACAC

ACCTACGCTAACGTACGCATCAACCATGTTATAAACCTGTGGGGAGCTGACTTTGATTCTAACGGGAACCTTAAA

GCTATTTATGTAACAGACTCTGATAGTAATGCATCTATTGGTATGAAGAAATACTTTGTTGGTGTTAATTCCGCT

GGAAAAGTAGCTATTTCTGCTAAAGAAATAAAAGAAGATAATATAGGTGCTCAAGTACTAGGGTTATTTACACTT

TCAACAGGGCAAAAAAGTTGGAATCAGACCAATGGCGGTGGCCATCATCACCATCACCACTAA
``` pCART209

```
                                                             (SEQ ID NO: 30)
ATGGATAGTTTTTCTGCTAATCAAGAGATTAGATATTCGGAAGTAACACCTTATCACGTTACTTCCGTTTGGACC

AAAGGAGTTACTCCTCCAGCAAACTTCACTCAAGGTGAAGATGTTTTTCACGCTCCTTATGTTGCTAACCAAGGA

TGGTATGATATTACCAAAACATTCAATGGAAAAGACGATCTTCTTTGCGGGGCTGCCACAGCAGGGAATATGCTT

CACTGGTGGTTCGATCAAAACAAAGACCAAATTAAACGTTATTTGGAAGAGCATCCAGAAAAGCAAAAAATAAAC

TTCAATGGCGAACAGATGTTTGACGTAAAAGAAGCTATCGACACTAAAAACCACCAGCTAGATAGTAAATTATTT

GAATATTTTAAAGAAAAAGCTTTCCCTTATCTATCTACTAAACACCTAGGAGTTTTCCCTGATCATGTAATTGAT

ATGTTCATTAACGGCTACCGCCTTAGTCTAACTAACCACGGTCCAACGCCAGTAAAAGAAGGTAGTAAAGATCCC

CGAGGTGGTATTTTTGACGCCGTATTTACAAGAGGTGATCAAAGTAAGCTATTGACAAGTCGTCATGATTTTAAA

GAAAAAATCTCAAAGAAATCAGTGATCTCATTAAGAAAGAGTTAACCGAAGGCAAGGCTCTAGGCCTATCACAC

ACCTACGCTAACGTACGCATCAACCATGTTATAAACCTGTGGGGAGCTGACTTTGATTCTAACGGGAACCTTAAA

GCTATTTATGTAACAGACTCTGATAGTAATGCATCTATTGGTATGAAGAAATACTTTGTTGGTGTTAATTCCGCT

GGAAAAGTAGCTATTTCTGCTAAAGAAATAAAAGAAGATAATATAGGTGCTCAAGTACTAGGGTTATTTACACTT

TCAACAGGGCAAGATAGTTGGGGTGGCGGCGGTGGCCATCATCACCATCACCACTAA
``` pCART125

```
                                                             (SEQ ID NO: 31)
ATGTCCGTTTGGACCAAAGGAGTTACTCCTCCAGCAAACTTCACTCAAGGTGAAGATGTTTTTCACGCTCCTTAT

GTTGCTAACCAAGGATGGTATGATATTACCAAAACATTCAATGGAAAAGACGATCTTCTTTGCGGGGCTGCCACA

GCAGGGAATATGCTTCACTGGTGGTTCGATCAAAACAAAGACCAAATTAAACGTTATTTGGAAGAGCATCCAGAA

AAGCAAAAAATAAACTTCAATGGCGAACAGATGTTTGACGTAAAAGAAGCTATCGACACTAAAAACCACCAGCTA

GATAGTAAATTATTTGAATATTTTAAAGAAAAAGCTTTCCCTTATCTATCTACTAAACACCTAGGAGTTTTCCCT

GATCATGTAATTGATATGTTCATTAACGGCTACCGCCTTAGTCTAACTAACCACGGTCCAACGCCAGTAAAAGAA
```

-continued

```
GGTAGTAAAGATCCCCGAGGTGGTATTTTTGACGCCGTATTTACAAGAGGTGATCAAAGTAAGCTATTGACAAGT

CGTCATGATTTTAAAGAAAAAAATCTCAAAGAAATCAGTGATCTCATTAAGAAAGAGTTAACCGAAGGCAAGGCT

CTAGGCCTATCACACACCTACGCTAACGTACGCATCAACCATGTTATAAACCTGTGGGGAGCTGACTTTGATTCT

AACGGGAACCTTAAAGCTATTTATGTAACAGACTCTGATAGTAATGCATCTATTGGTATGAAGAAATACTTTGTT

GGTGTTAATTCCGCTGGAAAAGTAGCTATTTCTGCTAAAGAAATAAAAGAAGATAATATAGGTGCTCAAGTACTA

GGGTTATTTACACTTTCAACAGGGCAAGATAGTTGGAATCAGACCAATGGCGGTGGCCATCATCACCATCACCAC

TAA
``` pCART213

(SEQ ID NO: 32)
```
ATGTCCGTTTGGACCAAAGGAGTTACTCCTCCAGCAAACTTCACTCAAGGTGAAGATGTTTTTCACGCTCCTTAT

GTTGCTAACCAAGGATGGTATGATATTACCAAAACATTCAATGGAAAAGACGATCTTCTTTGCGGGGCTGCCACA

GCAGGGAATATGCTTCACTGGTGGTTCGATCAAAACAAAGACCAAATTAAACGTTATTTGGAAGAGCATCCAGAA

AAGCAAAAATAAACTTCAAAGGCGAACAGATGTTTGACGTAAAAGAAGCTATCGACACTAAAAACCACCAGCTA

GATAGTAAATTATTTGAATATTTTAAAGAAAAAGCTTTCCCTTATCTATCTACTAAACACCTAGGAGTTTTCCCT

GATCATGTAATTGATATGTTCATTAACGGCTACCGCCTTAGTCTAACTAACCACGGTCCAACGCCAGTAAAAGAA

GGTAGTAAAGATCCCCGAGGTGGTATTTTTGACGCCGTATTTACAAGAGGTAACCAAAGTAAGCTATTGACAAGT

CGTCATGATTTTAAAGAAAAAAATCTCAAAGAAATCAGTGATCTCATTAAGAAAGAGTTAACCGAAGGCAAGGCT

CTAGGCCTATCACACACCTACGCTAACGTACGCATCAACCATGTTATAAACCTGTGGGGAGCTGACTTTGATTCT

AACGGGAACCTTAAAGCTATTTATGTAACAGACTCTGATAGTAATGCATCTATTGGTATGAAGAAATACTTTGTT

GGTGTTAATTCCGCTGGAAAAGTAGCTATTTCTGCTAAAGAAATAAAAGAAGATAATATAGGTGCTCAAGTACTA

GGGTTATTTACACTTTCAACAGGGCAAGATAGTTGGAATCAGACCAATGGCGGTGGCCATCATCACCATCACCAC

TAA
``` pCART214

(SEQ ID NO: 33)
```
ATGTCCGTTTGGACCAAAGGAGTTACTCCTCCAGCAAACTTCACTCAAGGTGAAGATGTTTTTCACGCTCCTTAT

GTTGCTAACCAAGGATGGTATGATATTACCAAAACATTCAATGGAAAAGACGATCTTCTTTGCGGGGCTGCCACA

GCAGGGAATATGCTTCACTGGTGGTTCGATCAAAACAAAGACCAAATTGAACGTTATTTGGAAGAGCATCCAGAA

AAGCAAAAATAAACTTCAAAGGCGAACAGATGTTTGACGTAAAAAAAGCTATCGACACTAAAAACCACCAGCTA

GATAGTAAATTATTTGAATATTTTAAAGAAAAAGCTTTCCCTTATCTATCTACTAAACACCTAGGAGTTTTCCCT

GATCATGTAATTGATATGTTCATTAACGGCTACCGCCTTAGTCTAACTAACCACGGTCCAACGCCAGTAAAAGAA

GGTAGTAAAGATCCCCGAGGTGGTATTTTTGACGCCGTATTTACAAGAGGTAACCAAAGTAAGCTATTGACAAGT

CGTCATGATTTTAAAGAAAAAAATCTCAAAGAAATCAGTGATCTCATTAAGGAAGAGTTAACCAAAGGCAAGGCT

CTAGGCCTATCACACACCTACGCTAACGTACGCATCAACCATGTTATAAACCTGTGGGGAGCTGACTTTGATTCT

AACGGGAACCTTAAAGCTATTTATGTAACAGACTCTGATAGTAATGCATCTATTGGTATGAAGAAATACTTTGTT

GGTGTTAATTCCGCTGGAAAAGTAGCTATTTCTGCTAAAGAAATAAAAGAAGATAATATAGGTGCTCAAGTACTA

GGGTTATTTACACTTTCAACAGGGCAAAAAGTTGGAATCAGACCAATGGCGGTGGCCATCATCACCATCACCAC

TAA
``` pCART228

(SEQ ID NO: 34)
```
ATGGACGATTACCAAAGGAATGCTACGGAAGCTTATGCCAAAGAAGTACCACATCAGATCACTTCCGTTTGGACC

AAAGGAGTTACTCCTCCAGCAAACTTCACTCAAGGTGAAGATGTTTTTCACGCTCCTTATGTTGCTAACCAAGGA

TGGTATGATATTACCAAAACATTCAATGGAAAAGACGATCTTCTTTGCGGGGCTGCCACAGCAGGGAATATGCTT

CACTGGTGGTTCGATCAAAACAAAGACCAAATTGAACGTTATTTGGAAGAGCATCCAGAAAAGCAAAAATAAAC

TTCAAAGGCGAACAGATGTTTGACGTAAAAAAAGCTATCGACACTAAAAACCACCAGCTAGATAGTAAATTATTT
```

-continued

```
GAATATTTTAAAGAAAAAGCTTTCCCTTATCTATCTACTAAACACCTAGGAGTTTTCCCTGATCATGTAATTGAT

ATGTTCATTAACGGCTACCGCCTTAGTCTAACTAACCACGGTCCAACGCCAGTAAAAGAAGGTAGTAAAGATCCC

CGAGGTGGTATTTTTGACGCCGTATTTACAAGAGGTAACCAAAGTAAGCTATTGACAAGTCGTCATGATTTTAAA

GAAAAAAATCTCAAAGAAATCAGTGATCTCATTAAGGAAGAGTTAACCAAAGGCAAGGCTCTAGGCCTATCACAC

ACCTACGCTAACGTACGCATCAACCATGTTATAAACCTGTGGGGAGCTGACTTTGATTCTAACGGGAACCTTAAA

GCTATTTATGTAACAGACTCTGATAGTAATGCATCTATTGGTATGAAGAAATACTTTGTTGGTGTTAATTCCGCT

GGAAAAGTAGCTATTTCTGCTAAAGAAATAAAAGAAGATAATATAGGTGCTCAAGTACTAGGGTTATTTACACTT

TCAACAGGGCAAAAAAGTTGGAATCAGACCAATGGCGGTGGCCATCATCACCATCACCACTAA
```

Example 2—Assessment of Potency (IgG Cleavage Efficacy)

ELISA

Enzymatic activity was measured using an ELISA-based potency assay. The principle of the ELISA was to coat wells of a multi titre plate with an antibody target (BSA), then incubate different concentrations of IgG cysteine protease polypeptide (test or control) with anti-BSA antibody in the wells, before detecting the quantity of anti-BSA antibody bound to the wells using a detector antibody. The higher the concentration of a given IgG cysteine protease polypeptide in a well, the less intact anti-BSA polypeptide will be bound to the wells, giving a lower signal. Similarly, a more potent IgG cysteine protease polypeptide will give a lower signal than a less potent IgG cysteine protease polypeptide when present at the same concentration.

The reference IdeS BX1001865 was prepared as a titration series in 1:2 dilution steps from 320 nM down to 0.16 nM to allow plotting of a standard calibration curve for the assay. The results achieved in the assay for multiple known concentrations of each tested polypeptide were compared against the linear section of the calibration curve to determine the concentration of reference IdeS which achieved the same potency. Dividing the known concentration of each polypeptide by the determined equivalent concentration of reference IdeS from the curve, a score is produced which is the fold change in potency relative to reference IdeS BX1001865. For example, if 5 nM test polypeptide achieves a result equivalent to 10 nM reference IdeS on the calibration curve, the test polypeptide has a potency 2 fold greater than reference IdeS BX1001865. A mean score for fold change in potency relative to reference IdeS BX1001865 was calculated from all of the scores achieved at the different concentrations for each tested polypeptide, provided that they fell within the linear section of the calibration curve. This mean score was then compared to the mean score achieved for pCART124 reference IdeS, which was included on each plate to enable comparison between plates. The mean score for pCART124 is divided by the mean score for the test polypeptide to produce a "pCART124 ratio", which is effectively the fold change in potency relative to IdeS for each polypeptide. This pCART124 ratio could then be visualised on a bar diagram.

Briefing summarising the laboratory protocol: Wells of multi-titre plates were coated overnight with BSA (10 µg/ml), then washed with PBS-T and blocked for 1 hour with 2% fish skin gelatine in PBS. IdeS BX1001865 polypeptide was prepared as a titration series in 1:2 dilution steps in PBS with 0.1% gelatine from 320 nM down to 0.16 nM. The test polypeptides and the pCART124 control were then prepared at each of 15, 7.5, 3.75, and 1.9 nM in PBS with 0.1% gelatine. A 50 µl sample of polypeptide was added to each well with 50 µl of rabbit anti-BSA (ACRIS, #R1048P, 10 nM) as substrate. The plates were incubated at room temperature for 1 hour and then washed with PBS-T. Biotinylated goat anti-rabbit Fc-specific antibody (30 000× diluted) was added as a detector antibody and incubated for 30 min. The plate was washed and 40 000× diluted SA-Horseradish Peroxidase (HRP; Pierce) was added and incubated for 30 min. The plates were washed and developed using TMB One Component as a chromogenic substrate for HRP for 7 min, stopped with 0.5 M $H_2SO_4$. Absorbance (OD) was measured at λ=450 nm. Mean scores for fold change in potency relative to BX1001865 were determined for each test polypeptide and for pCART124. The "pCART124 ratio" for each test polypeptide was then calculated as set out above.

The "pCART124 ratio" results for pCART152, 183, 184, 185, 186, 187, 189 and 190 are shown in FIG. 1, alongside the result for pCART124. All of the exemplary polypeptides of the invention shown here achieve at least 1.5 fold improvement in potency relative to the IdeS control (pCART124). pCART152, 183, 184, 188, 189 and 190 all achieve much higher potency, even as high as 8.0 fold improvement over control for pCART189. Each of these six text polypeptides includes the N130R/K modification. The pCART125 polypeptide was tested separately and achieved potency comparable to that of IdeS (data not shown).

Visualisation of IgG Cleavage Patterns

The efficacy of the different pCART polypeptides was further evaluated by visualising on SDS-PAGE the cleavage products produced by a titration series of each polypeptide in different substrates. To test efficacy in pure IgG substrate, adalimumab (Humira) was used for IgG1 and denosumab (XGEVA) for IgG2. To test efficacy in a more complex physiological environment, some of the polypeptides were also titrated in in IVIg (Octagam). This allows the evaluation of the impact of neutralizing anti-IdeS antibodies on polypeptide activity. Cleavage patterns for each polypeptide are compared with the cleavage patterns of IdeS (BX1001865 and pCART124) in the same substrate. The protocol was follows:

For the pure IgG tests, each test polypeptide or control was diluted in a 1:3 steps titration series from 6.7 µg/ml down to 0.04 ng/ml in PBS with 0.05% BSA as supporting protein. 25 µl of each concentration was transferred to multi titre plates and the cleavage reaction was starting by adding 25 µl of either Humira or XGEVA (2 mg/ml). Thus each starting concentration of polypeptide is diluted 1:2 in the well, giving a titration series of 3.3 µg/ml down to 0.02 ng/ml.

For the IVIg tests, each test polypeptide or control was diluted in a 1:2 steps titration series from 30 μg/ml down to 0.015 ng/ml in PBS with 0.05% BSA as supporting protein. 25 μl of each concentration was transferred to multi titre plates and the cleavage reaction was starting by adding 25 μl of 10 mg/ml IVIg. Thus each starting concentration of polypeptide is diluted 1:2 in the well, giving a titration series of 15 μg/ml down to 0.0075 ng/ml.

The plates were incubated in 37° C. for 1.5 hours. The samples were mixed 1:4 in 2×SDS loading buffer and heated at 92° C. for 5 min. 10 μl were loaded on a polyacrylamide gel (15-well 4-20% Mini-PROTEAN®TGX™precast gel (Biorad) which was read according to standard protocols.

Figure 2:
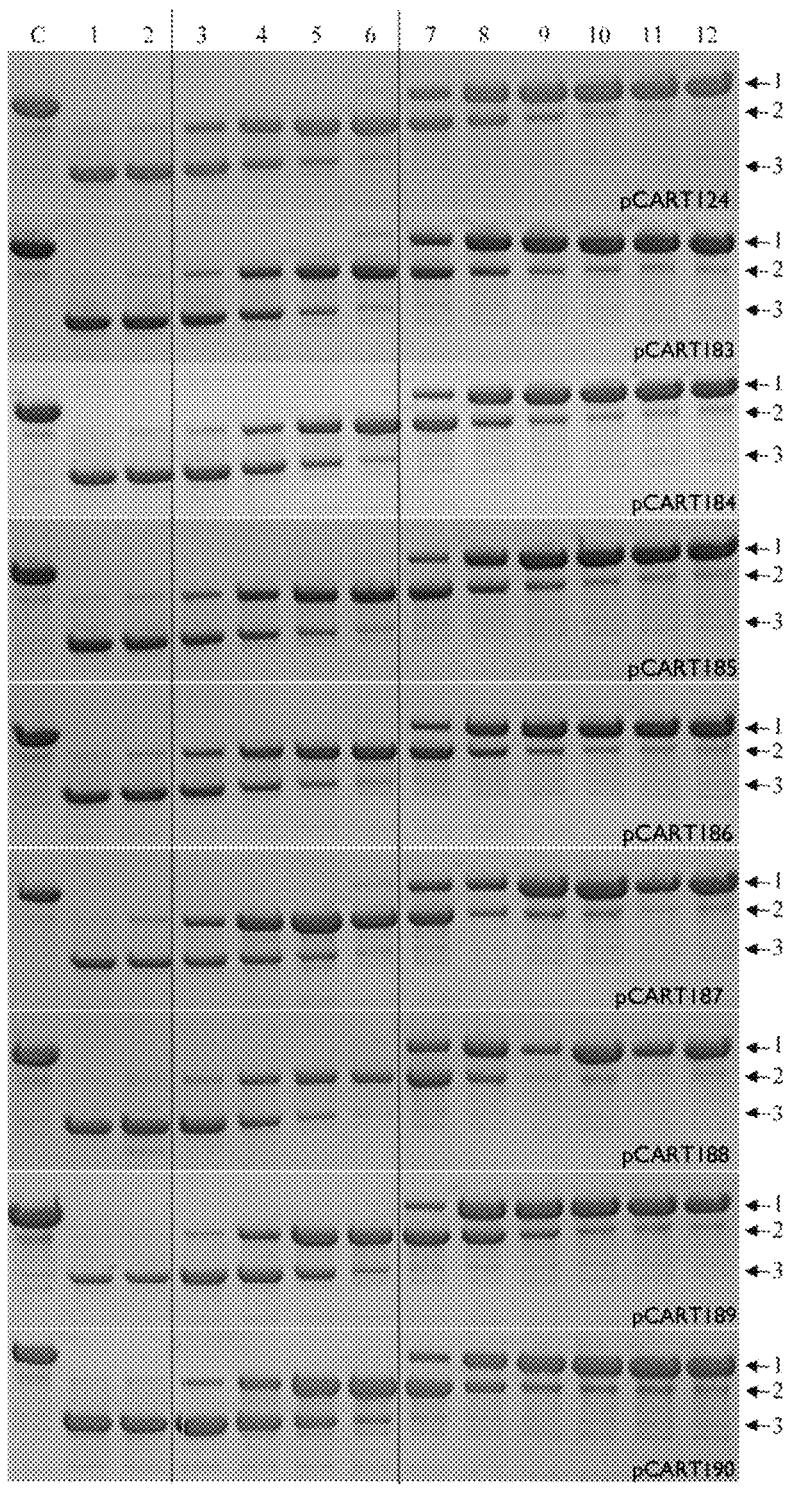
FIG. 2 shows the results of a representative SDS-PAGE gel used to visualize the cleavage products produced by incubation of IgG1 with polypeptides of the invention or controls.

FIG. 2 shows the cleavage patterns produced with IgG1 (adalimumab) substrate for pCART183, 184, 185, 186, 187, 189 and 190 as compared to IdeS (pCART124). Polypeptide concentrations are from 3.33 μg/ml (lane 1) down to 0.02 ng/ml (lane 12) in a 1:3 step dilution series. Intact adalimumab (without enzyme) is visualized to the left (lane C).

The arrows on the right indicate the different cleavage products from IgG. Arrow 1: Intact IgG; arrow 2: scIgG (single cleaved IgG—results from cleavage of first IgG heavy chain); arrow 3: F(ab')$_2$ fragment (results from cleavage of second IgG heavy chain). Vertical lines were added to facilitate the comparison at the $1^{st}$ IgG heavy chain cleavage, where Intact IgG becomes scIgG (between lane 6 and 7) and at the $2^{nd}$ IgG heavy chain cleavage, where scIgG becomes F(ab')$_2$ fragment (between lane 2 and 3).

pCART183, 184, 188, 189 and 190 in particular all show increased cleavage efficacy of the $2^{nd}$ heavy chain resulting in more intense F(ab')$_2$ (arrow 3) band and less intense scIgG band (arrow 2), compared to pCART124 at the same concentrations. The difference is seen from the 0.12 μg/ml concentration (lane 4) but is even more evident at 0.37 μg/ml (lane 3). Thus, overall FIG. 2 shows that a change to a positive amino acid at position 130 (N130R/K) increase the efficacy of cleavage of the $2^{nd}$ IgG heavy chain (pCART183, 184, 188, 189 and 190).

Figure 3:
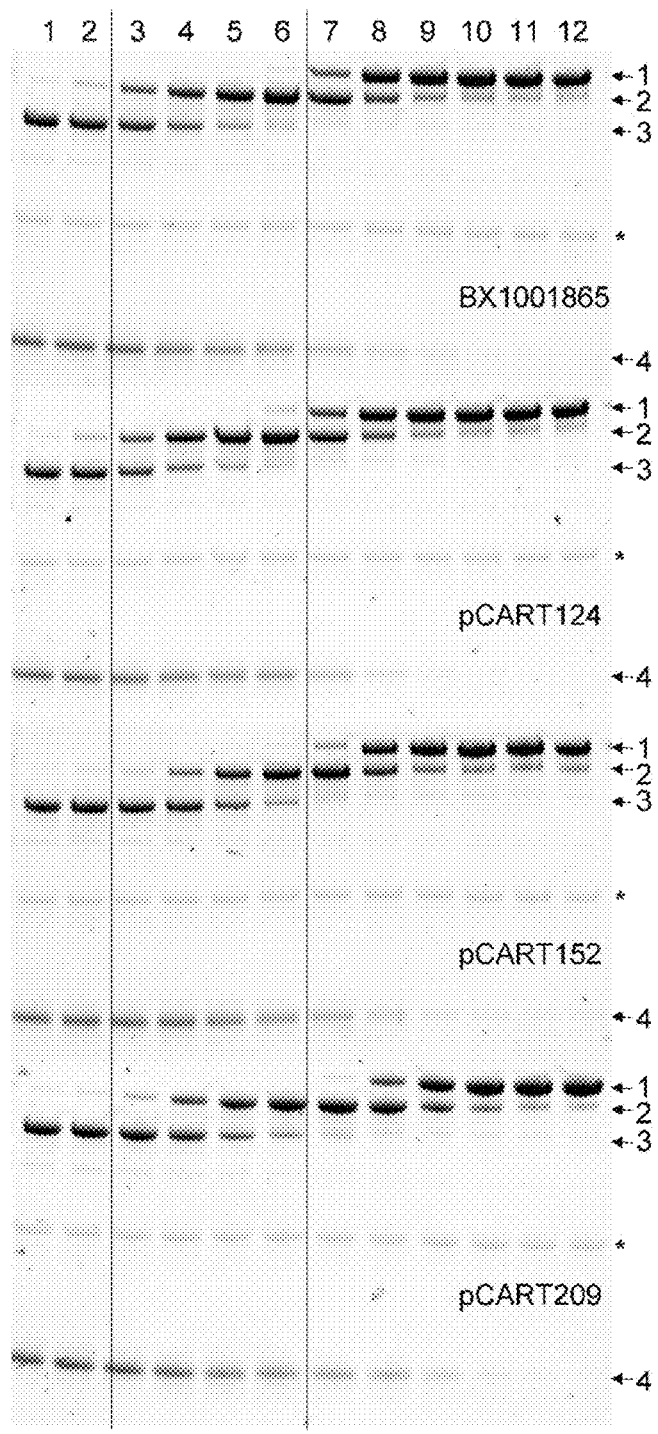
FIG. 3 shows the results of a representative SDS-PAGE gel used to visualize the cleavage products produced by incubation of IgG1 with further polypeptides of the invention or controls.

FIG. 3 shows the cleavage patterns produced with IgG1 substrate for pCART152 and pCART209, as compared to both IdeS controls (pCART124 and BX1001865). Enzyme concentrations are from 3.33 μg/ml (lane 1) down to 0.02 ng/ml (line 12) in a 1:3 step dilution series. The arrows on the right indicate the different cleavage products from IgG. Arrow 1: Intact IgG; arrow 2: scIgG (single cleaved IgG—results from cleavage of first IgG heavy chain); arrow 3: F(ab')$_2$ fragment (results from cleavage of second IgG heavy chain); arrow 4: Fc fragment; (*) indicates the carrier protein (BSA) in the titration buffer. Vertical lines were added to facilitate the comparison at the $1^{st}$ IgG heavy chain cleavage, where Intact IgG becomes scIgG (between lane 6 and 7) and at the $2^{nd}$ IgG heavy chain cleavage, where scIgG becomes F(ab')$_2$ fragment (between lane 2 and 3).

pCART152 and pCART209 both show increased cleavage efficacy of the 2nd heavy chain resulting in a more intense F(ab')$_2$ bands (arrow 3) and less scIgG remaining (arrow 2), compared to pCART124 and BX1001865 (arrow 3 and 2) at the same concentration. This difference is seen from enzyme concentrations of 41 ng/ml (lane 5) but is even more evident at 0.12 μg/ml and 0.37 μg/ml (lane 4 and 3). Both pCART152 and pCART209 show cleavage efficacy of the 2nd heavy chain about 3× original IdeS (BX1001865 and pCART124), i.e. 0.37 μg/ml of pCART152 and pCART209 (lane 3) produces similar result to 1.11 μg/ml of BX100186 and pCART124 (lane 2).

pCART152 and pCART209 also show an improved efficacy in the cleavage of the $1^{st}$ IgG heavy chain, resulting in a more intense scIgG band (arrow 2) and a less intense IgG band (arrow 1) compared to original IdeS (BX1001865 and pCART124) at the same concentration. For pCART152 this can be seen at 1.5 ng/ml of enzyme (lane 8) but is even more obvious at 4.6 ng/ml (lane 7). pCART209 shows an increased cleavage efficacy about 3× original IdeS (BX1001865 and pCART124) also for the first heavy chain cleavage, i.e. 4.6 ng/ml (lane 7) of pCART209 produces similar result to 14 ng/ml (lane 6) of BX1001865 and pCART124.

Thus, FIG. 3 shows that a single amino acid substitution at position 130 (N130K in pCART152) increases the efficacy of cleavage of primarily the $2^{nd}$ but also to some extent the $1^{st}$ IgG1 heavy chain, and that a deletion of the NQTN sequence (pCART209) improves the cleavage efficacy by 3 fold for both the $1^{St}$ and $2^{nd}$ IgG1 heavy chains.

Figure 4:
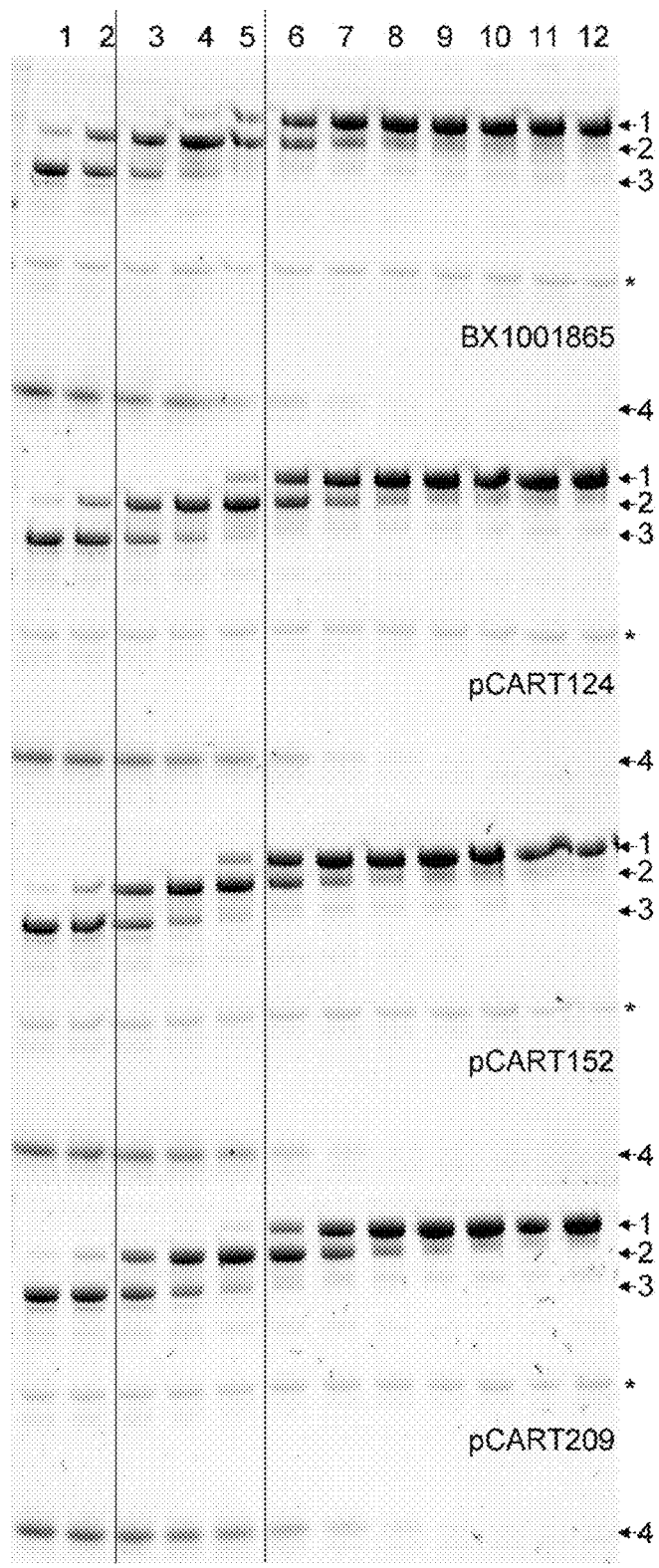
FIG. 4 shows the results of a representative SDS-PAGE gel used to visualize the cleavage products produced by incubation of IgG2 with polypeptides of the invention or controls.

FIG. 4 shows the cleavage patterns produced with IgG2 substrate for pCART152 and pCART209, as compared to both IdeS controls (pCART124 and BX1001865). Enzyme concentrations are from 3.33 μg/ml (lane 1) down to 0.02 ng/ml (line 12) in a 1:3 step dilution series. The arrows on the right indicate the different cleavage products from IgG. Arrow 1: Intact IgG; arrow 2: scIgG (single cleaved IgG—results from cleavage of first IgG heavy chain); arrow 3: F(ab')$_2$ fragment (results from cleavage of second IgG heavy chain); arrow 4: Fc fragment; (*) indicates the carrier protein (BSA) in the titration buffer. Vertical lines were added to facilitate the comparison at the $1^{st}$ IgG heavy chain cleavage, where Intact IgG becomes scIgG (between lane 6 and 7) and at the $2^{nd}$ IgG heavy chain cleavage, where scIgG becomes F(ab')$_2$ fragment (between lane 2 and 3).

pCART152 and pCART209 both show increased cleavage efficacy of the $2^{nd}$ heavy chain resulting in a more intense F(ab')$_2$ (arrow 3) bands and less intense scIgG (arrow 2) compared to pCART124 and BX1001865 (arrow 3 and 2) at the same concentrations. This difference is seen from enzyme concentrations of 0.37 μg/ml (lane 3) but even more evident at 1.11 μg/ml (lane 2).

The result in lane 6 (enzyme concentration 14 ng/ml) for pCART209 as compared to BX1001865 and pCART124 shows that pCART209 is also more effective at cleaving the $1^{st}$ IgG heavy chain. This results in a less intense intact IgG band (arrow 1) and a more intense scIgG band (arrow 2) as most protein has been converted to scIgG.

Thus, FIG. 4 shows that a single amino acid substitution at position 130 (N130K in pCART152) increases the efficacy of cleavage of primarily the $2^{nd}$ IgG2 heavy chain, and that a deletion of the NQTN sequence (pCART209) improves the cleavage efficacy of both the $1^{st}$ and $2^{nd}$ heavy IgG2 chains.

Overall, it can be seen that the test polypeptides are generally more effective than IdeS at cleaving IgG1 and IgG2. Consistent with the ELISA results, pCART152, 183, 184, 188, 189 and 190 appear to be particularly effective. The increased efficacy for these polypeptides appears to relate primarily to cleavage of the second IgG heavy chain.

A change to a positive amino acid from the G at position 131 is expected to produce similar results to the N130R/K substitution. Positions 130 and 131 are situated in the loop of a beta hairpin structure spanning positions 126 to 136 of SEQ ID NO: 1. Based on the results obtained herein, changes to positive amino acids in either or both of positions 130 and 131 are expected to increase IgG cysteine protease activity.

Example 3—Assessment of Immunogenicity

Competitive ADA Assay

This assay is based on competition between a test polypeptide and IdeS for binding to anti-IdeS antibody. A pre-incubation of test enzyme and IVIg will enable binding of anti-IdeS antibodies to the tested pCART enzyme. Thereafter the IVIg-enzyme-mix is added to an IdeS-coated plate and any anti-IdeS antibody not bound to test polypeptide will instead bind to the IdeS on the plate. All binding incubations was made in the presence of 2 mM iodoacetic acid (IHAc) to inhibit IgG cleavage and in high salt so that only high affinity binding occurs. After washing, a biotinylated goat anti-human F(ab')$_2$-specific F(ab')$_2$ fragment is used as detector. Poor recognition of test polypeptide by the anti-IdeS antibodies in IVIg will result in high binding of the anti-IdeS antibodies in IVIg to the plate, giving a high signal. Good recognition of test polypeptide by the anti-IdeS antibodies in IVIg will give the opposition result. The detailed protocol is as follows:

Reference IdeS (BX1001865) was coated overnight on multi-titre plates (5 µg/ml), then washed with PBS-T and blocked for 1 hour with 2% BSA in PBS supplemented with 2 mM IHAc and 1 M NaCl. A mixing plate was prepared with stepwise dilutions of test polypeptide and 20 µg/ml IVIg in PBS supplemented with 0.1% BSA, 2 mM IHAc and 1 M NaCl. The mixing plate was incubated for 1 hour at room temperature on a shaker. After incubation, the blocking solution was discarded from the IdeS-coated plate and 50 µl of each mixture from the mixing plate was transferred to the wells of the coated plate. After incubation for 1 hour room temperature on a shaker, the plate was washed with PBS-T and a detector, biotinylated goat anti-human F(ab')$_2$-specific F(ab')$_2$ fragment (20 000× diluted) was added. After incubation for 30 minutes the plate was washed and 40 000× diluted SA-HRP (Pierce) was added and incubated for 30 min. The plate was washed and developed using TMB One Component as a chromogenic substrate for HRP for 7 min, stopped with 0.5 M H$_2$SO$_4$. Absorbance (OD) was measured at λ=450 nm. The results were inverted (1/OD value) and presented as a ratio compared with pCART124 (1/(test polypeptide/pCART124)) for visualisation in bar diagrams.

Figure 5:
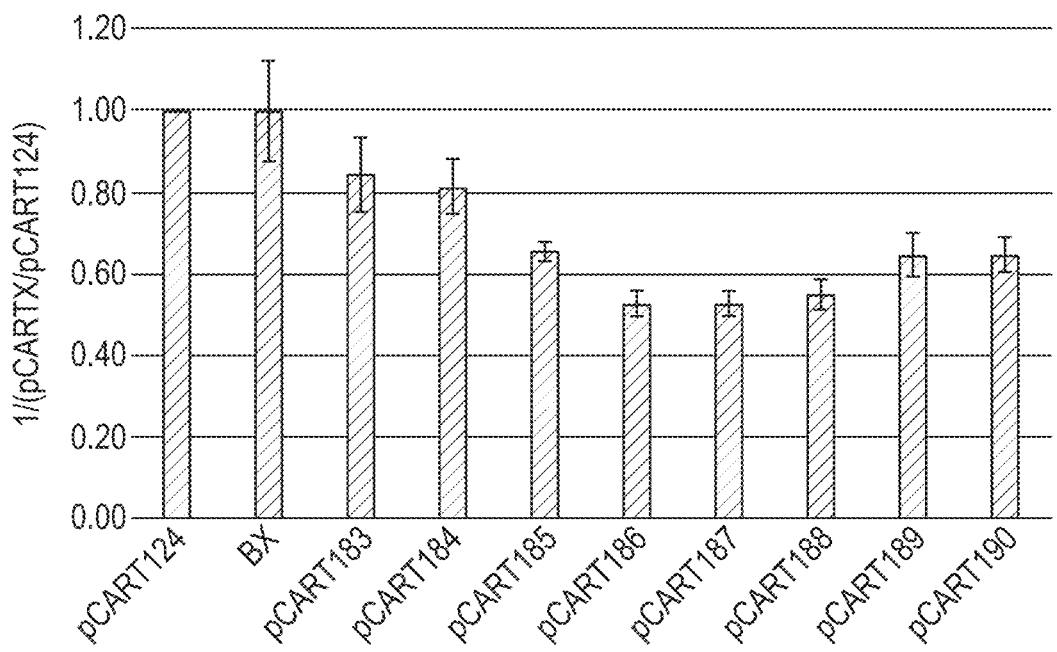
FIGS. 5 and 6 show the results of representative competition assays to determine the level of recognition of polypeptides of the invention by IdeS-specific antibodies, as compared to controls.
Figure 6:
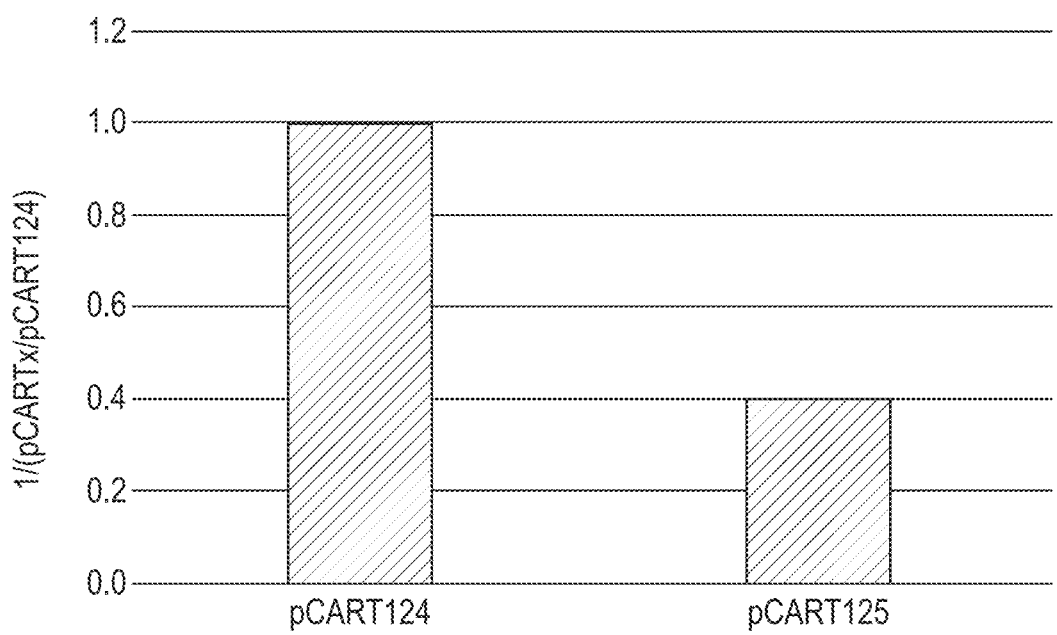

The results for pCART183, 184, 185, 186, 187, 189 and 190 are shown in FIG. 5. The results for pCART125 are shown in FIG. 6. All of the tested polypeptides show some reduction in anti-IdeS antibody recognition as compared to IdeS, typically at least 10%. pCART185, 186 and 187 in particular show a greater reduction in recognition, of around 40% relative to IdeS. pCART125 shows a reduction of around 60%.

SUMMARY

All of the tested polypeptides show increased potency and/or reduced immunogenicity relative to IdeS.

Example 4—Assessment of Potency

Potency ELISA

Figure 13:
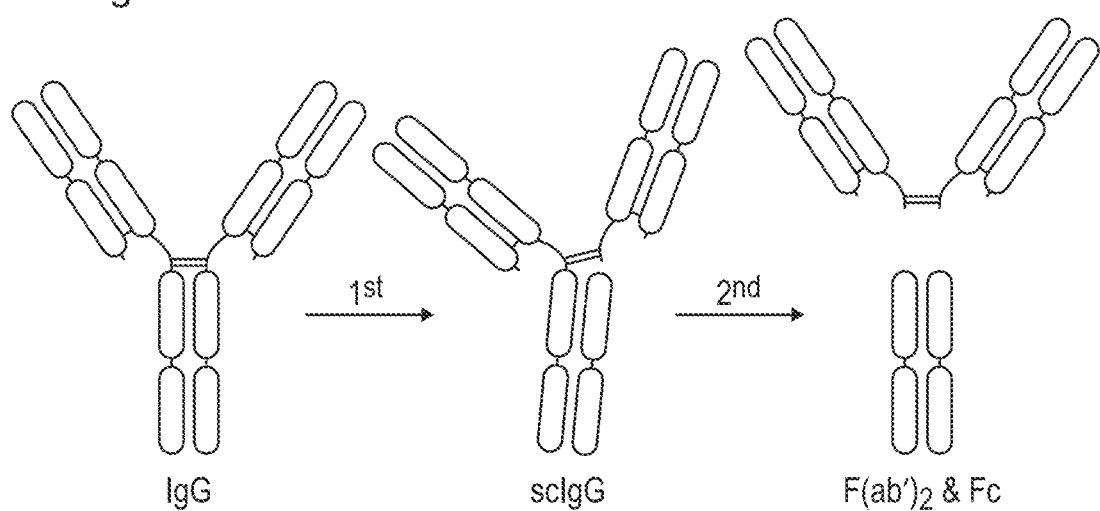
FIG. 13 Schematic representation of the cleavage of immunoglobulins by polypeptides of the invention.

To address the cleavage capacity of human IgG1 and IgG2, two ELISA-based potency assays were set up. One assay measuring IgG1 cleavage and the other IgG2 cleavage. EC50 (half maximal effective concentration) values were calculated for the different IgG cysteine protease polypeptides tested. The principle of the assays was to coat wells of a multi titre plate with a F(ab)$_2$-fragment directed to human IgG antibodies with specificity to the Fab region. Then titrated concentrations of IgG cysteine protease polypeptide (test or control) were incubated together with human IgG1 antibody (Humira) or human IgG2 antibody (XGEVA) in the wells. The quantity of intact or single cleaved human IgG (Humira or XGEVA) bound to the wells was measured using a detector antibody directed to human IgG with specificity against the Fc part of the antibody. The higher the concentration of a given IgG cysteine protease polypeptide in a well, the less intact human IgG antibody will be bound to the well, giving a lower signal. Similarly, a more potent IgG cysteine protease polypeptide will give a lower signal than a less potent IgG cysteine protease polypeptide when present at the same concentration. Titration dose-response curves were prepared for the IdeS control (pCART124) and all tested IgG cysteine protease polypeptides, in both the IgG1 (humira) and IgG2 (XGEVA) assay. EC50 values were also calculated for each tested variant, representing the concentration of a polypeptide where 50% of its maximal effect, in the second cleavage of the IgG molecule, is observed i.e. the concentration where half of the IgG are fully cleaved. A lower EC50 value represents a more effective IgG cysteine protease. The cleavage of the first IgG heavy chain, IgG to scIgG, is not visible in this assay because the Fc-part of the IgG is still present and can be detected by the Fc specific detector antibody (FIG. 13).

Brief summary of the laboratory protocol: Wells of multi titre plates were coated overnight (+2-8° C.) with Goat-anti-human Fab-specific F(ab)$_2$-fragment (0.5 µg/ml) (Jackson #109-006-097), then washed with PBS+0.05% Tween 20 (PBS-T) and blocked in 0.45% fish gelatin in Phosphate Buffered Saline-Tween (PBS-T) (block buffer) for 45-120 min at room temperature. Control IdeS (pCART124) and the IgG cysteine protease polypeptides to be tested were prepared as a titration series in 1:4 dilution steps in block buffer with a starting concentration of 80 µg/ml. Equal volumes (25 µl) of human IgG1 (Humira) at a concentration of 0.5 µg/ml and the titrated amounts of IgG cysteine protease polypeptides were added to the wells and incubated 2 hours with shaking in a controlled temperature environment at 37° C. and then washed with PBS-T. Biotinylated mouse anti-human IgG Fc-specific (m-a-hIgG Bio II, Lot: C0013-ZC43C, Southern Biotech) (600 ng/ml) antibody was mixed with Strep-sulfo (200 ng/ml) and added to the multi titre plates. The plates were sealed with aluminum tape and incubated at +25° C. for 1 hour with shaking. The plates were then washed in PBS-T and 150 µl of 2× diluted Read buffer T (MSD read buffer T, Cat. no. R92TC-2) were added to each well. The plates were immediately read on a Plate reader, MSD (Meso Scale Discovery) QuickPlex SQ 120 Model 1300.

Efficacy assays visualised on gel: Assay conducted as described in Example 2 for cleavage of IgG1 (Humira), IgG2 (XGEVA) as well as cleavage of a pool of human IgG IVIg (Octagam).

Results

Potency ELISA

Figure 7:
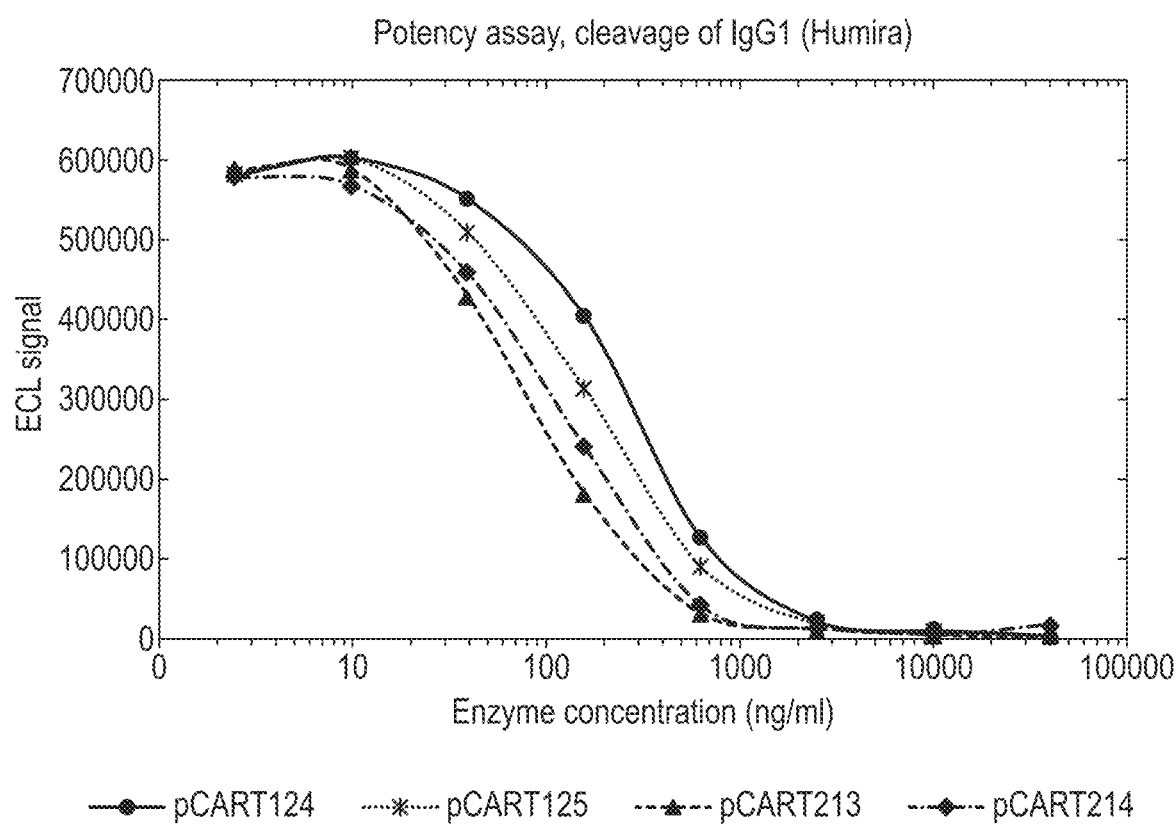
FIG. 7 shows representative titration curves for cleavage of IgG1 by different IgG cysteine protease polypeptides.
Figure 8:
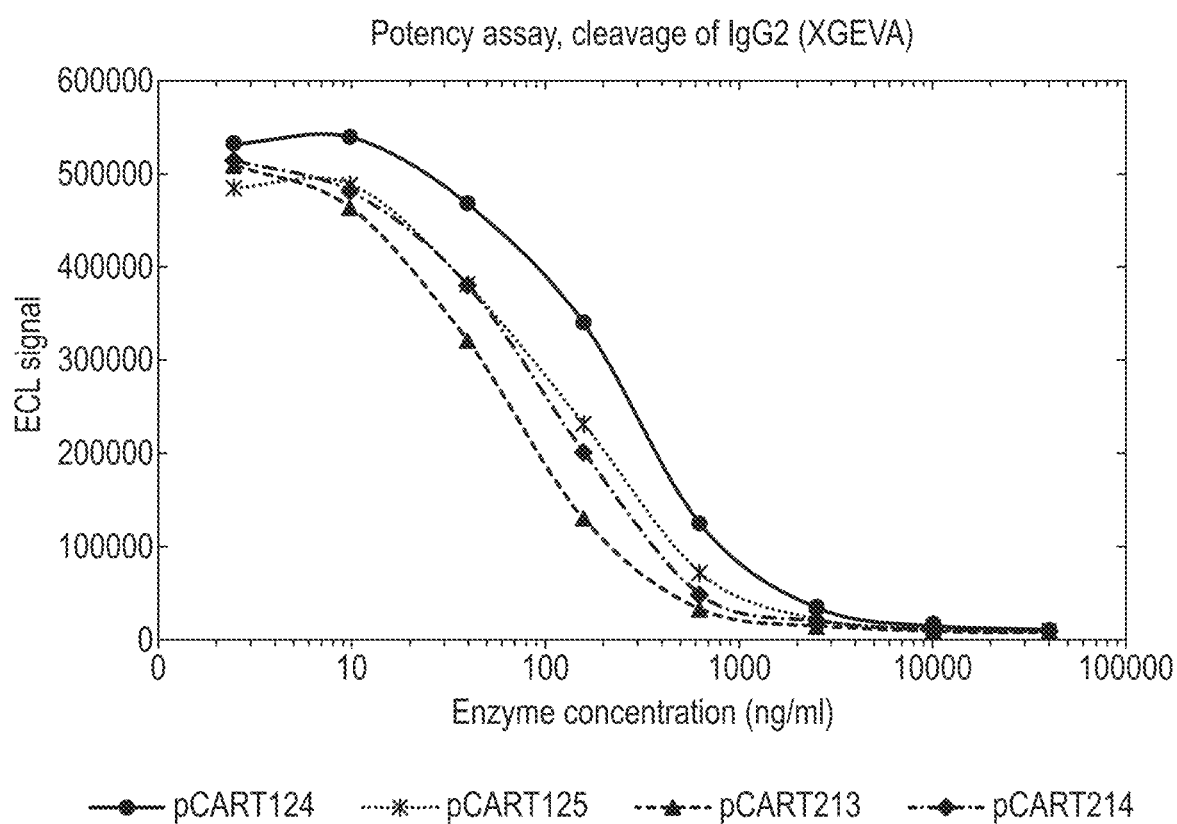
FIG. 8 shows representative titration curves for cleavage of IgG2 by different IgG cysteine protease polypeptides.

The resulting dose-response curves for the tested IgG cysteine proteases in the potency assays are shown in FIG. 7 (IgG1 cleavage) and FIG. 8 (IgG2 cleavage). pCART125, 213 and 214 of the exemplary polypeptides of the invention tested here have improved potency with decreased EC50 values (table 1) in cleaving both heavy chains of IgG1 (FIG. 7) and IgG2 (FIG. 8) compared to the IdeS control pCART124, with a fold improvement in potency in cutting IgG1 of 1.5 for pCART125, 2.2 for pCART214 and as much as 3.0 for pCART213. For cleavage of IgG2 (FIG. 8) the fold improvement compared to pCART124 (IdeS) was 1.6 for pCART125, 2.1 for pCART214 and 3.5 for pCART213.

Efficacy Assays Visualised on Gel

Figure 9:
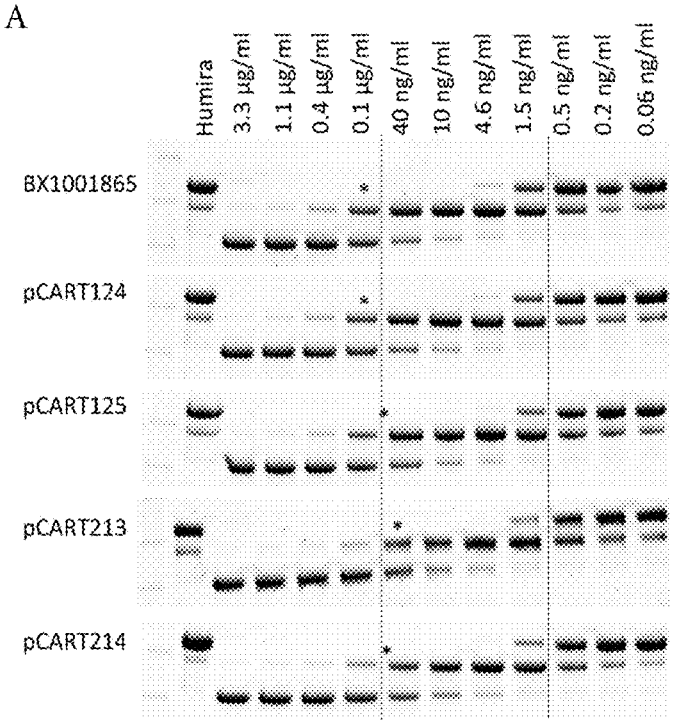
FIG. 9 shows the results of a representative SDS-PAGE used to visualize the cleavage products produced by incubation of IgG with polypeptides of the invention or controls.
Figure 9:
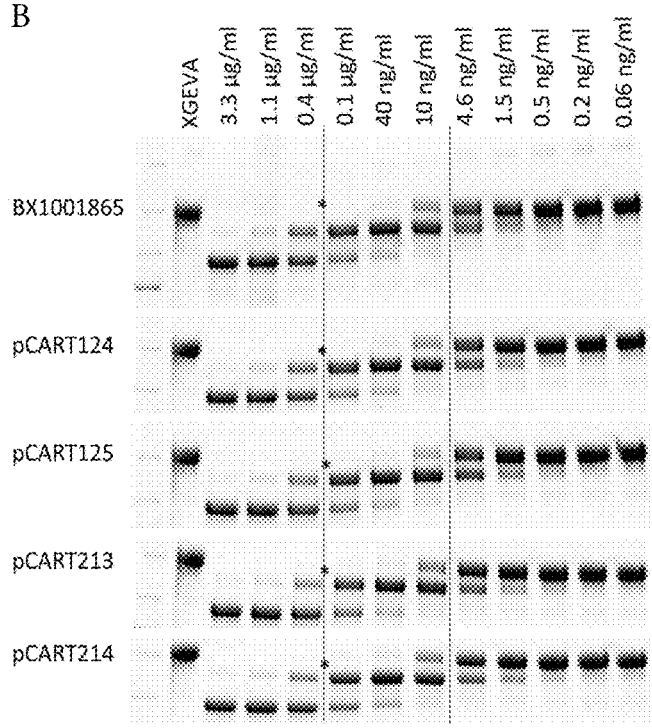

The cleavage of IgG1 (FIG. 9A) and IgG2 (FIG. 9B) visualised on gel clearly show the first and second heavy chain cleavage (the vertical lines in the figures mark the $1^{st}$ and $2^{nd}$ IgG heavy chain cleavage by BX1001865 and pCART124 cleavage). The * in the figures illustrate the approximate EC50 value i.e. the concentration where 50% of the IgG is single cleaved (scIgG) and 50% is fully cleaved (F(ab')$_2$). The data from the gels are summarised in table 2 (IgG1 cleavage) and table 3 (IgG2 cleavage). The concentration of IgG cysteine protease needed for cleavage of the $1^{st}$ heavy chain of IgG1 (Humira) is about the same for all polypeptides tested, 1.5 ng/ml for BX1001865 and pCART124 (IdeS controls), pCART125, 213 and 214 (FIG. 9A). For the $2^{nd}$ heavy chain cleavage of IgG1 IdeS, pCART125 and 214 approximately 120 ng/ml is needed do get a dominant F(ab')$_2$ band on the gels and about one titration step less, 40 ng/ml, for pCART213 (FIG. 9A). The IgG2 (XGEVA) cleavage visualised in FIG. 9B show that all the polypeptides tested, BX1001865, pCART124, 125, 213 and 214, demonstrate about the same efficacy with 14 ng/ml needed for cutting the $1^{st}$ IgG heavy chain and generate scIgG2 and about 370 ng/ml to generate F(ab')$_2$ fragments (table 3). In another set of efficacy experiment pCART228 was tested against Humira (IgG1) and XGEVA (IgG2) with BX1001865 and pCART124 as IdeS controls (FIGS. 10A and 10B, table 4). Approximately one titration step higher concentration is needed for the controls (BX1001865 and pCART124) in these experiments compared to FIG. 9 and table 3, small differences between experiments can be observed due to sample handling and laboratory precision in the titration dilutions of the samples. To get a reliable comparison pCART228 must be compared to the cleavage of IdeS controls in the same experiment. Very similar IgG cleavage patterns are seen for pCART228 and the IdeS controls in both the IgG1 and IgG2 cleavage (FIGS. 10A and B), but with approximately 3× (one titration step) more efficient cleavage of the $2^{nd}$ IgG heavy chain of IgG1 by pCART228 (FIG. 10A) with 120 ng/ml needed compared to 370 ng/ml for IdeS (table 4).

Figure 11:
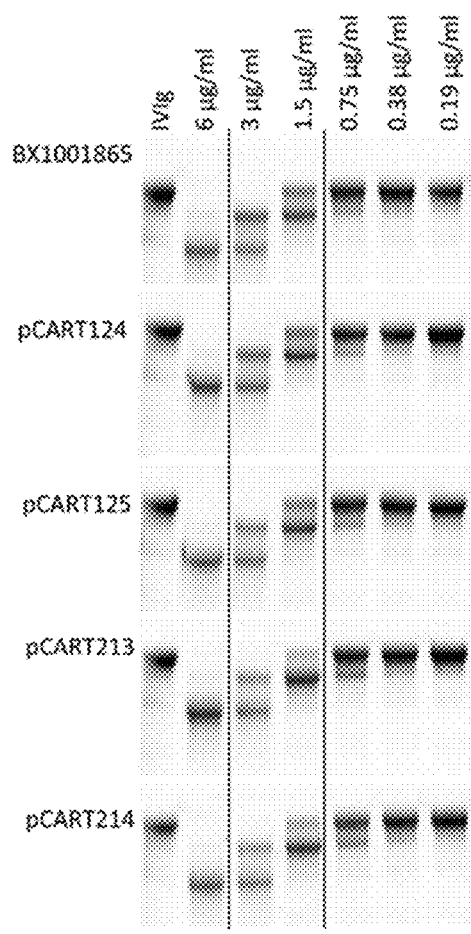
FIG. 11 shows the results of a representative SDS-PAGE used to visualize the cleavage products produced by incubation of IVIg with polypeptides of the invention or controls.

The IgG cysteine protease polypeptides pCART125, 213, and 214 were also titrated in the human IgG pool, IVIg (Octagam) with IdeS (BX1001865 and pCART124) as controls (FIG. 11). All tested polypeptides needed 1.5 µg/ml for the first IgG heavy chain cleavage and about 6 µg/ml for the second (FIG. 11 and table 5). The cleavage of IVIg by pCART228 was analysed in a broader titration spectra with 1:2 dilutions from 30 µg/ml (FIG. 12) compared to the tested variants in FIG. 11. The same efficacy is seen for IdeS (BX1001865 and pCART124) and pCART228 (FIG. 12) with a concentration of 1.9 µg/ml to generate scIgG and 7.5 µg/ml to give F(ab')$_2$ fragments (table 6) these represents the same titration steps as for pCART125, 213 and 214 (FIG. 11 and table 5).

Summary of Figures for Example 4

FIG. 7 Titration curves for cleavage of IgG1 (Humira) by different IgG cysteine protease polypeptides.

FIG. 8 Titration curves for cleavage of IgG2 (XGEVA) by different IgG cysteine protease polypeptides.

FIG. 9 IgG cleavage analyzed by SDS-PAGE using titrated (1:3 dilution from 3300 ng/ml) amounts of pCART125, 213 and 214, with BX1001865 and pCART124 (original IdeS) as controls in the same cleavage experiment. A: cleavage of humira (IgG1) and B: cleavage of XGEVA (IgG2). Vertical lines mark the IdeS (BX1001865 and pCART124) concentrations needed to give the $1^{st}$ and $2^{nd}$ IgG heavy chain cleavage (where the amount of the cleaved product dominates over the uncleaved product). The * in the figures represent the approximate EC50 value in this experiment.

Figure 10:
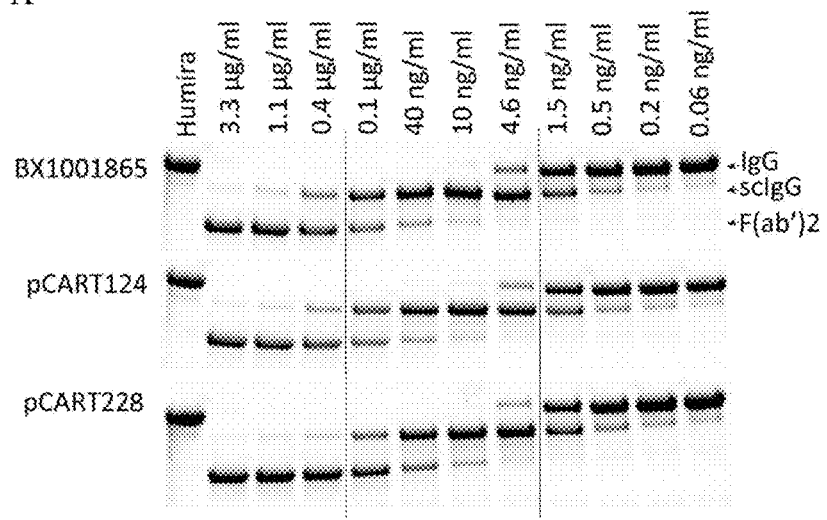
FIG. 10 shows the results of a representative SDS-PAGE used to visualize the cleavage products produced by incubation of IgG with polypeptides of the invention or controls.
Figure 10:
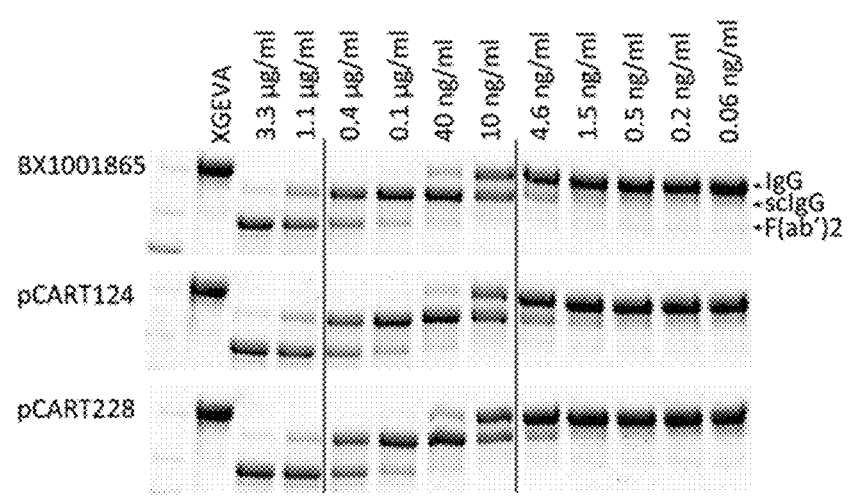

FIG. 10 IgG cleavage analyzed by SDS-PAGE using titrated (1:3 dilution from 3300 ng/ml) amounts of pCART228 with BX1001865 and pCART124 (original IdeS) as controls in the same cleavage experiment. A: cleavage of humira (IgG1) and B: cleavage of XGEVA (IgG2). Vertical lines mark the IdeS (BX1001865 and pCART124) concentrations needed to give the $1^{st}$ and $2^{nd}$ IgG heavy chain cleavage (where the amount of the cleaved product dominates over the uncleaved product).

FIG. 11 IVIg cleavage analyzed by SDS-PAGE using titrated (1:2 dilution from 6 µg/ml) amounts of the tested IgG cysteine protease polypeptides and IdeS (BX1001865 and pCART124) as control in the same cleavage experiment.

Figure 12:
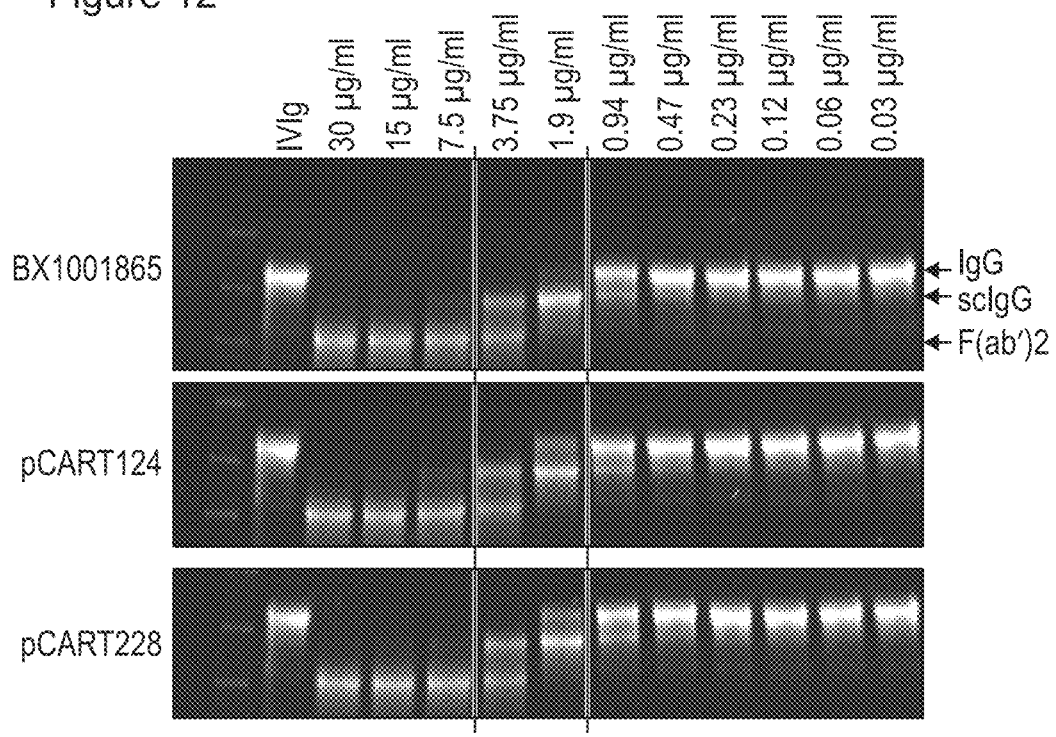
FIG. 12 shows the results of a representative SDS-PAGE used to visualize the cleavage products produced by incubation of IVIg with polypeptides of the invention or controls.

FIG. 12 IVIg cleavage analyzed by SDS-PAGE using titrated amounts (1:2 dilution from 30 µg/ml) of pCART228 with IdeS (BX1001865 and pCART124) as controls in the same cleavage experiment.

FIG. 13 Schematic representation of the cleavage of immunoglobulins by polypeptides of the invention. The enzymatic cleavage of the IgG is performed in two steps. First, one heavy chain of intact IgG is cleaved and single cleaved IgG (scIgG) is generated. Secondly, the next IgG heavy chain is cut and the Fc-part is released. The Fc-part is still attached to the Fab-part in the scIgG molecule and since the detector antibody in the potency ELISA is recognizing the Fc-part of the IgG molecule the assay will not differentiate between complete IgG from scIgG.

Discussion and Conclusion

The lower EC50 values for pCART125, 213 and 214 in the potency ELISA indicate that these polypeptides have an improved potency in the $2^{nd}$ heavy chain cleavage (from scIgG to F(ab')$_2$) of both IgG1 and IgG2 compared to pCART124 (original IdeS). Visualising the IgG cleavage on gel shows the cutting of the $1^{st}$ heavy chain (from IgG to scIgG) which is not measurable in the potency ELISA using an Fc-specific detector antibody. Most Fc-mediated actions of IgG are lost in a single cleaved molecule (data not shown), which is central in a clinical situation where the main focus is to incapacitate pathogenic IgG molecules. pCART228 is as effective in both IgG1 and IgG2 cleavage as original IdeS. This is important when an IgG cysteine protease of the same molecular size as IdeS is needed having the desirable lower recognition of IdeS specific antibodies. IVIg is a pool of human IgG containing approximately 65-70% IgG1, 35-30% IgG2 and IgG3/IgG4 sharing about 1%. Human IVIg also naturally contains anti-IdeS antibodies, from the IgG donor's earlier exposure to S. pyogenes. The anti-IdeS antibodies in human IVIg are neutralizing insofar as their binding to IdeS may diminish or completely demolish the IdeS IgG protease activity. The results of IVIg cleavage show the overall cleavage of all different IgG subclasses, with a dominance of IgG1 and IgG2, and with the presence of neutralizing anti-IdeS antibodies. Generally, all IgG cysteine protease polypeptides tested have lower efficacy in IgG2 cleavage compared to IgG1.

TABLE 1

EC50 (ng/ml) measured by potency ELISA and fold difference in potency compared to original IdeS (pCART124).

| | EC50 (ng/ml) in cleavage of IgG1 (Humira) | Fold improvement in potency | EC50 (ng/ml) in cleavage of IgG2 (XGEVA) | Fold improvement in potency |
|---|---|---|---|---|
| pCART124 | 243 | 1 | 199 | 1 |
| pCART125 | 165 | 1.5 | 125 | 1.6 |
| pCART213 | 80 | 3.0 | 57 | 3.5 |
| pCART214 | 111 | 2.2 | 95 | 2.1 |

TABLE 2

Data for IgG1 (Humira) cleavage shown on gel (FIG. 9A). Concentration (ng/ml) of polypeptide needed to achieve $1^{st}$ and $2^{nd}$ IgG cleavage, where the cleaved product dominates in amounts over the uncleaved. Approximate EC50 value (* in FIG. 9A).

| ID | $1^{st}$ IgG heavy chain IgG to scIgG Conc. of enzyme (ng/ml) | $2^{nd}$ IgG heavy chain scIgG to F(ab')2 Conc. of enzyme (ng/ml) | Approximate EC50 value, i.e. equal amounts of scIgG and F(ab')2 (*) Conc. of enzyme (ng/ml) |
|---|---|---|---|
| BX1001865 | 1.5 | 120 | 100 |
| pCART124 | 1.5 | 120 | 100 |
| pCART125 | 1.5 | 120 | 40-100 |
| pCART213 | 1.5 | 40 | 40 |
| pCART214 | 1.5 | 120 | 40-100 |

TABLE 3

Data for IgG2 (XGEVA) cleavage shown on gel (FIG. 9B). Concentration (ng/ml) of polypeptide needed to achieve $1^{st}$ and $2^{nd}$ IgG cleavage, where the cleaved product dominates in amounts over the uncleaved. Approximate EC50 value (* in FIG. 9B).

| ID | $1^{st}$ IgG heavy chain IgG to scIgG Conc. of enzyme (ng/ml) | $2^{nd}$ IgG heavy chain scIgG to F(ab')2 Conc. of enzyme (ng/ml) | Approximate EC50 value, i.e. equal amounts of scIgG and F(ab')2 (*) Conc. of enzyme (ng/ml) |
|---|---|---|---|
| BX1001865 | 14 | 370 | 100-400 |
| pCART124 | 14 | 370 | 100-400 |
| pCART125 | 14 | 370 | 100-400 |
| pCART213 | 14 | 370 | 100-400 |
| pCART214 | 14 | 370 | 100-400 |

TABLE 4

Data for IgG1 (Humira) cleavage and IgG2 (XGEVA) by pCART228 shown on gel (FIG. 10). Concentration (ng/ml) of polypeptide needed to achieve $1^{st}$ and $2^{nd}$ IgG cleavage (where the cleaved product dominates in amounts over the uncleaved).

| ID | $1^{st}$ IgG1 (Humira) heavy chain IgG to scIgG Conc. of enzyme (ng/ml) | $2^{nd}$ IgG1 (Humira) heavy chain scIgG to F(ab')2 Conc. of enzyme (ng/ml) | $1^{st}$ IgG2 (XGEVA) heavy chain IgG to scIgG Conc. of enzyme (ng/ml) | $2^{nd}$ IgG2 (XGEVA) heavy chain scIgG to F(ab')2 Conc. of enzyme (ng/ml) |
|---|---|---|---|---|
| BX1001865 | 4.6 | 370 | 14 | 1100 |
| pCART124 | 4.6 | 370 | 14 | 1100 |
| pCART228 | 4.6 | 120 | 40 | 1100 |

TABLE 5

Data for IVIg cleavage by pCART125, 213 and 214 shown on gel (FIG. 11). Concentration (ng/ml) of polypeptide needed to achieve $1^{st}$ and $2^{nd}$ IgG cleavage, where the cleaved product dominates in amounts over the uncleaved.

| ID | $1^{st}$ IgG heavy chain IgG to scIgG Conc. of enzyme (ng/ml) | $2^{nd}$ IgG heavy chain scIgG to F(ab')2 Conc. of enzyme (ng/ml) |
| --- | --- | --- |
| BX1001865 | 1500 | 6000 |
| pCART124 | 1500 | 6000 |
| pCART125 | 1500 | 6000 |
| pCART213 | 1500 | 6000 |
| pCART214 | 1500 | 6000 |

TABLE 6

Data for IVIg cleavage by pCART228 shown on gel (FIG. 12). Concentration (ng/ml) of polypeptide needed to achieve $1^{st}$ and $2^{nd}$ IgG heavy chain cleavage, where the cleaved product dominates in amounts over the uncleaved.

| ID | $1^{st}$ IgG heavy chain IgG to scIgG Conc. of enzyme (ng/ml) | $2^{nd}$ IgG heavy chain scIgG to F(ab')2 Conc. of enzyme (ng/ml) |
| --- | --- | --- |
| BX1001865 | 1900 | 7500 |
| pCART124 | 1900 | 7500 |
| pCART229 | 1900 | 7500 |

Example 5—ADA ELISA, a Competitive ELISA for ADA-IdeS Binding Sites

Anti-drug antibody (ADA) binding sites against IdeS was measured for "ADA" modified polypeptide of the invention (pCART125, 213 and 214), using an ELISA, Meso Scale Discovery (MSD), based assay. The principle of the ELISA was to coat wells of a multi titre plate with original his-tagged-IdeS (pCART124). Most humans have antibodies against IdeS in their serum due to earlier infections of group A *streptococcus*. Here, two different clinical human serum pools were used as standards for detection of ADA. The first pool is normal human serum from 100 individuals, called Human serum pool 1191807, and the second is a pool of serum from patients in the phase II study 13-HMedIdeS-02, called Phase II pool-2. These patients have been administered with IdeS once in a dose-range of 0.24-0.5 mg/kg body weight and thereby have induced levels (approximately 50 times) of anti-IdeS ADA in their serum.

The outline of this competitive ADA ELISA is that IdeS (pCART124) is coated in the bottom of a micro titre plate. Human serum pools are pre-incubated together with the polypeptides of the invention, to be tested for ADA recognition, or with the positive control IdeS (pCART124) in a molar ration of 1:100 with 100× excess of polypeptides of the invention. The concentration of the two different serum pools used for pre-incubation is estimated from the standard curve to give approximately 80% binding to original IdeS. If the ADA binding sites have been abolished in the polypeptides tested, these variants could not compete with the binding of ADA to the original IdeS at the bottom of the wells, i.e. a low signal demonstrates strong ADA-resemblance to the original IdeS (pCART124) and a high signal demonstrates weak ADA-resemblance to the original IdeS.

The concentration of both standards achieving approximately 80% binding at the linear section of the standard curve was about 200 ng ADA (IdeS)/ml. In the competitive pre-incubation this concentration of both standards were used separately and the concentration of the polypeptides of the invention were used in a concentration of 100 times the ADA concentration, including the molar weight difference between an antibody of 150 kDa and IdeS of approximately 35 kDa, 4.2 times, giving 100 times 200 ng/ml dividing with 4.2 giving approx. 5 μg/ml of the tested polypeptides. The standard serum containing 200 ng/ml ADA and the IdeS (pCART124) or polypeptides of the invention are pre-incubated together for 1 hour at room temperature (RT). As a control for maximum ADA binding, the same concentration of the standards were pre-incubated without IdeS (pCART124) or tested polypeptides and used as 80% binding max value. The lowest level of the standards curve, were used as lower limit values for the range of the calculation of the competition. The mean score for the standards pre-incubated with IdeS (pCART124) or tested polypeptides were subtracted with the 80% standard binding value divided with 80% standard binding value subtracted with the lower limit values giving % competition value. The tested polypeptides with the lowest % competition means that the most ADA binding epitopes have been abolished compared to original IdeS (pCART124).

Brief summary of the laboratory protocol: Wells of multi titre plates were coated overnight with pCART124 (1 μg/ml), washed 3 times with PBS-T and blocked for 1 hour with 0.45% fish skin gelatine and 2 mM of the cysteine protease inhibitor Iodoacetic acid (IHAc) in PBS.

Both standards were prepared as titration series in 1:3 dilution steps in 0.45% fish skin gelatine and 2 mM IHAc in PBS, from 5000 ng ADA (IdeS)/ml to 2.5 ng ADA (IdeS)/ml to allow plotting of a standard calibration curve for the assay, with measurements at both the linear part and the maximum and minimum part of the standard curve. At the same time as the blocking of the plate, the standards and the IdeS (pCART124) or tested polypeptides were pre-incubated together for 1 hour at RT, i.e. the samples in a competition step, using 200 ng/ml ADA (standards) and 5 μg/ml IdeS (pCART124) or polypeptides to be tested.

The pCART124 coated plate was washed 3 times and 50 μl pre-incubated samples or 50 μl standard were added to each well of the multi titre plate.

The plate was incubated at RT for 2 hours and then washed with PBS-T. Goat-anti-human F(ab) specific $F(ab)_2$ fragment-bio (Jackson #109-066-097, 0.65 mg/ml), (1000× diluted) was added as detector antibody and Streptavidin-Sulfo (MSD Cat. No: R32AD-1 or R32AD-5) (2000× diluted) in blocking buffer incubated for 1 hour at RT in the dark. The plate was washed 3 times and Read buffer T (MSD Read buffer T (4×) 4× diluted was added and the plate was analysed on a Plate reader, MSD (Meso Scale Discovery) QuickPlex SQ 120 Model 1300 directly.

Results and Conclusion

All tested IgG cysteine protease polypeptides, pCART125, 213 and 214 are less recognized by IdeS specific ADA in human serum compared to original IdeS (pCART124). Some of the ADA recognition epitopes are found in the N-terminal part of IdeS. All these polypeptides of the invention are N-terminally deleted compared to IdeS and the only sequential difference between pCART125 and the original IdeS is the N-terminal deletion.

Figure 14:
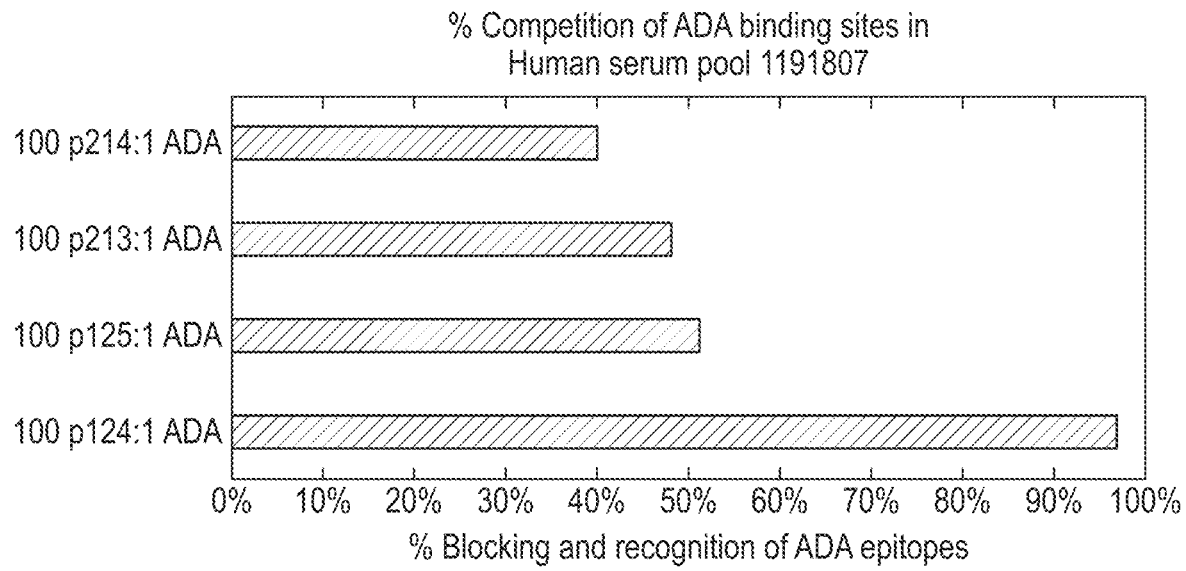
FIG. 14 shows the results of a representative % competition of ADA binding sites with polypeptides of the invention or controls.
Figure 15:
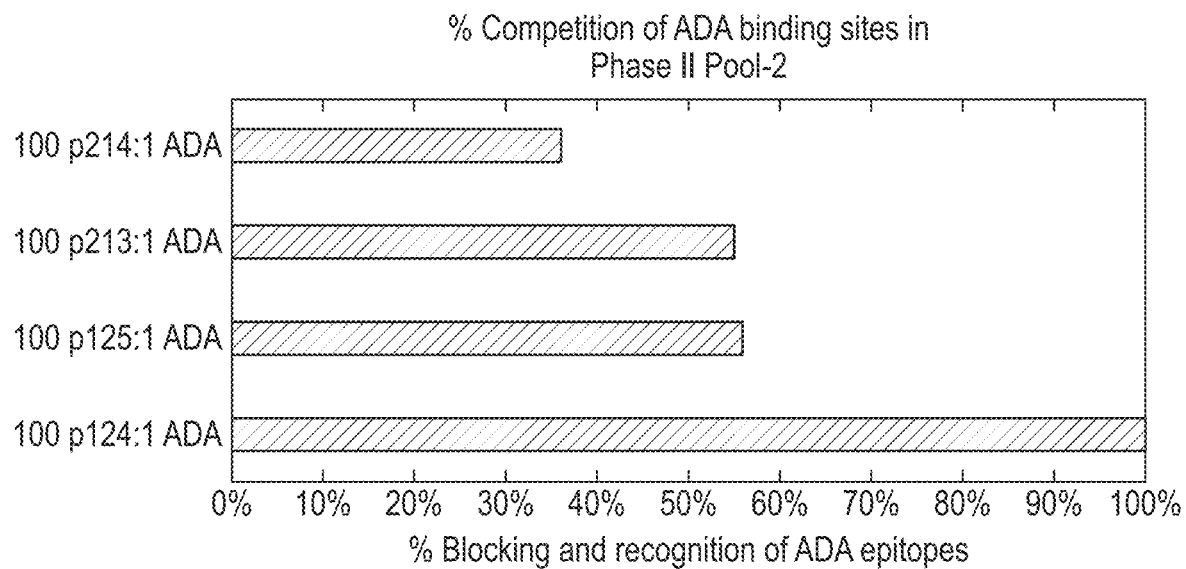
FIG. 15 shows the results of a further representative % competition of ADA binding sites with polypeptides of the invention or controls.

Percentage (%) blocking of IdeS-ADA binding sites for pCART125, 213 and 214 are shown in FIGS. 14 and 15 and the original IdeS pCART124 is used as positive control for 100% resemblance.

Example 6—Assessment of In Vivo Efficacy in an Octagam (Human IVIg) Mouse Model

In the present study BALB/c mice were injected intraperitoneally (i.p.) with human IVIg (Octagam). The concentration of human IVIg was administered at a dose of 900 mg/kg, to correlate to the human IgG plasma concentration (10 mg/ml). Human IVIg was injected i.p. day 0. Twenty four hours (day 1) after the injection of human IVIg, PBS, IdeS controls (BX1001865 and pCART124) or the IgG cysteine proteases to be tested, pCART125, pCART213 and pCART214, were administered intravenously (i.v.) at a dose of 1 mg/kg. Two hours later serum samples were collected and mice were sacrificed.

Efficacy ELISA

The principle of the assay was to coat wells of a multi titre plate with a F(ab')$_2$-fragment directed to human IgG antibodies with specificity to the Fab region. Then serum from mice treated with IVIg and IdeS controls (BX1001865 and pCART124) or the tested IgG cysteine protease polypeptide were added. The quantity of intact or single cleaved human IgG (IVIg) bound to the wells was measured using a detector antibody directed to human IgG (IVIg) with specificity against the Fc part of the antibody. The lower the detected concentration of intact human IgG antibody (IVIg) the more effective the IgG cysteine protease polypeptide is expected to be.

Brief summary of the laboratory protocol: Wells of a multi titre plate were coated overnight (+2-8° C.) with Goat-anti-human Fab-specific F(ab)$_2$-fragment (0.5 µg/ml) (Jackson #109-006-097), then washed with PBS+0.05% Tween 20 (PBS-T) and blocked in 2% BSA in PBS-T (block buffer) for 45-120 min at RT (room temperature). The Human Serum Protein Calibrator (DAKO #X0908) was used as a standard and added in a range from 0.5-300 ng/ml. The serum samples taken from mice treated with IVIg and different IgG cysteine protease polypeptides were thawed and diluted in block buffer 100 000 times before addition to the assay multi titre plate. The plate was incubated 2 hours with shaking at RT and then washed with PBS-T. Biotinylated mouse anti-human IgG Fc-specific (600 ng/ml) (Jackson #109-066-098) antibody was mixed with Strep-sulfo (200 ng/ml) (MSD #R32AD-1) and added to the multi titre plate. The plate was sealed with aluminum tape and incubated at RT for 1 hour with shaking. The plate was then washed in PBS-T and 150 µl of 2× diluted Read buffer T (MSD #R92TC-2) was added to each well. The plate was immediately analysed on a plate reader, MSD (Meso Scale Discovery) QuickPlex SQ 120 Model 1300 directly.

Efficacy Visualized on Gel

10 µl mice serum was diluted in 1:10 in 90 µl PBS. Thereafter 10 µl diluted serum was mixed with 30 µl 4×SDS-PAGE loading buffer. 5 µl of IgG in-house marker was used to show the different IgG fragments (IgG, scIgG and F(ab')$_2$). Samples were heated at 92° C. for 3 min (Thermo mixer compact, eppendorf) and briefly centrifuged before loading 10 µl on 4-20% Mini-Protean® TGX, Stain-free™ gel (Cat. #456-8096, Biorad). Gels were run at 200 V for 40 min.

Results and Conclusion

In vivo cleavage of human IVIg (Octagam) by IdeS controls (BX1001865 and pCART124) and pCART125, 213 and 214 were compared by studying the level of human IgG in serum by efficacy ELISA and by analysing the degradation of IgG by SDS-PAGE. Treatment with the IdeS controls (BX1001865 and pCART124) and the different IgG cysteine proteases pCART125, pCART213 and pCART214 in mice showed a clear effect on cleaving human IgG in vivo (Table 7 and FIG. 16).

Figure 16:
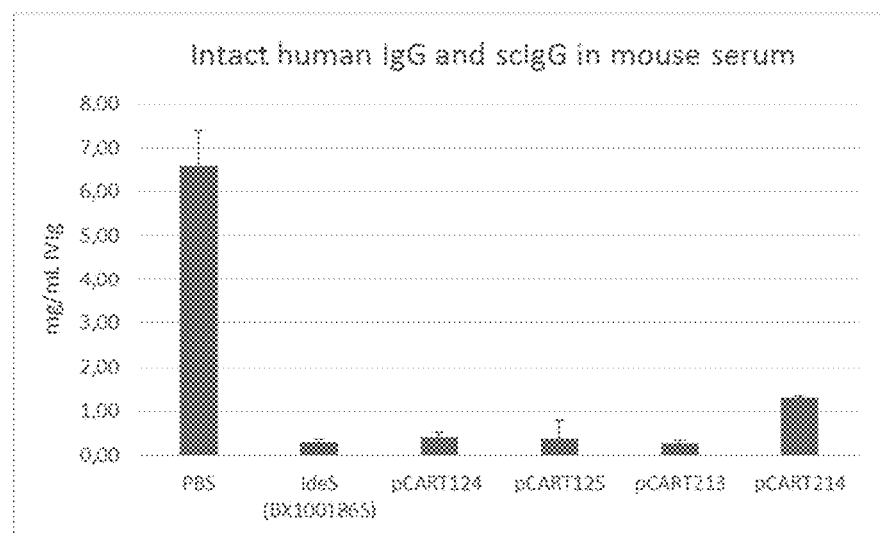
FIG. 16 shows the results of a representative efficacy ELISA used to determine the efficacy of the polypeptides of the invention in cleaving human IgG in vivo.
Figure 17:
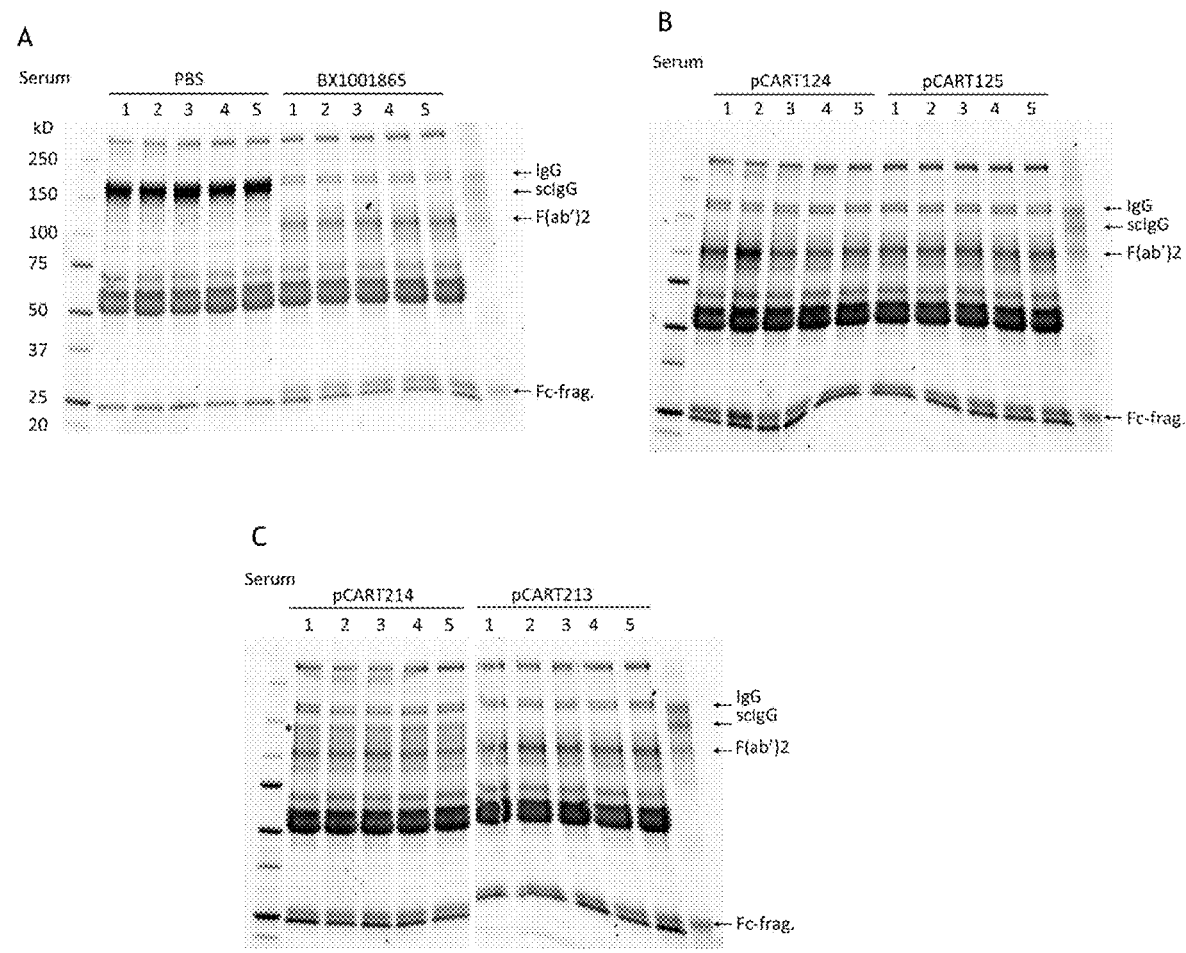
FIG. 17 shows the results of a representative SDS-PAGE use to visualize the IgG cleavage products produced in vivo by polypeptides of the invention.

Complete cleavage were shown for the IdeS controls (BX100186 and pCART124), pCART125 and pCART213, with no scIgG bands visible and significant F(ab')$_2$ bands on the gels (FIG. 17). pCART214 showed a lower efficacy in this mouse model with scIgG molecules present in the serum after two hours (* in FIG. 17C). However, no intact IVIg could be detected on the gel meaning that the higher bar for pCART214 in FIG. 16 represents scIgG and not intact IgG. This shows that polypeptides of the invention cleave IgG in an in vivo model.

TABLE 7

Analysis of in vivo cleavage of human IgG in serum from mice treated with IdeS (BX1001865 and pCART124)/IdeS variants by the efficacy ELISA (average ± Stdev).

| | Average (mg/mL) | Stdev |
|---|---|---|
| Control (PBS) | 6.58 | 0.80 |
| BX1001865 | 0.30 | 0.05 |
| pCART124 | 0.39 | 0.12 |
| pCART125 | 0.38 | 0.39 |
| pCART213 | 0.26 | 0.06 |
| pCART214 | 1.29 | 0.05 |

The invention claimed is:

1. A polypeptide having IgG cysteine protease activity and comprising a variant of the sequence of SEQ ID NO:2, which variant:
   (a) is at least 80% identical to SEQ ID NO: 7;
   (b) has a cysteine (C) at the position in said variant sequence which corresponds to position 94 of SEQ ID NO: 1; and
   (c) has, at the positions in said variant sequence which correspond to positions 84, 262, 284 and 286 of SEQ ID NO: 1, a lysine (K), a histidine (H), an aspartic acid (D) and an aspartic acid (D), respectively;
   wherein said polypeptide is more effective at cleaving IgG than IdeS and/or is less immunogenic than IdeS, and wherein said variant of the sequence of SEQ ID NO: 2 comprises a substitution made at one or more of the positions corresponding to positions 115, 119, 139, 142, 198, 216, 226, 241, 245, 302, 316, and 333 of SEQ ID NO: 1.

2. The polypeptide according to claim 1, wherein said variant of the sequence of SEQ ID NO: 2 is at least 90%, 95% or 99% identical to SEQ ID NO: 7.

3. The polypeptide according to claim 1, wherein said sequence includes an additional methionine at the N terminus and/or a histidine tag at the C terminus.

4. The polypeptide according to claim 1, wherein said polypeptide is at least 1.5 fold, 2.0 fold, 2.5 fold, 3.0 fold, 4.0 fold, 4.5 fold, 5.0 fold, 6.0 fold, 7.0 fold or 7.5 fold greater more effective than IdeS at cleaving IgG, when measured in the same assay.

5. The polypeptide according to claim 1 which is less immunogenic than IdeS, wherein preferably the immunogenicity of said polypeptide is no more than 85% of the immunogenicity of IdeS when measured in the same assay.

* * * * *